(12) United States Patent
Akopov et al.

(10) Patent No.: US 12,268,569 B2
(45) Date of Patent: Apr. 8, 2025

(54) TREATMENT PLANNING FOR ALIGNING A PATIENT'S TEETH

(71) Applicant: Align Technology, Inc., San Jose, CA (US)

(72) Inventors: Igor Akopov, Moscow (RU); Evgeniy Morozov, Ulyanovsk (RU); Alexander Belous, Moscow (RU); Alexander Kulinich, Nizhegorodskaya (RU); Irina Ivanova, Moscow (RU); Mikhail Nyukhtikov, Zhukovsky (RU); Maria Shirshova, Krasnodar (RU); Olga Matusevich, Moscow (RU); Olga Likhacheva, Moscow (RU)

(73) Assignee: Align Technology, Inc., San Jose, CA (US)

( * ) Notice: Subject to any disclaimer, the term of this patent is extended or adjusted under 35 U.S.C. 154(b) by 522 days.

(21) Appl. No.: 17/410,760

(22) Filed: Aug. 24, 2021

(65) Prior Publication Data

US 2022/0039918 A1    Feb. 10, 2022

Related U.S. Application Data

(63) Continuation of application No. 17/406,071, filed on Aug. 18, 2021, which is a continuation of application No. 16/178,491, filed on Nov. 1, 2018, now Pat. No. 11,096,763.

(60) Provisional application No. 62/580,432, filed on Nov. 1, 2017, provisional application No. 62/580,427, filed on Nov. 1, 2017, provisional application No. 62/692,551, filed on Jun. 29, 2018.

(51) Int. Cl.
| | |
|---|---|
| A61C 7/00 | (2006.01) |
| A61C 7/08 | (2006.01) |
| A61C 9/00 | (2006.01) |
| G16H 50/50 | (2018.01) |

(52) U.S. Cl.
CPC ............ *A61C 7/002* (2013.01); *A61C 7/08* (2013.01); *A61C 9/0053* (2013.01); *G16H 50/50* (2018.01)

(58) Field of Classification Search
CPC ............................. A61C 7/002; G06F 3/00
See application file for complete search history.

(56) References Cited

U.S. PATENT DOCUMENTS

| | | | |
|---|---|---|---|
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,457,972 B1 | 10/2002 | Chishti et al. |
| 6,488,499 B1 | 12/2002 | Miller |
| 6,554,611 B2 | 4/2003 | Chishti et al. |
| 6,582,229 B1 | 6/2003 | Miller et al. |

(Continued)

FOREIGN PATENT DOCUMENTS

CN    101616637 A    12/2009

*Primary Examiner* — Ralph A Lewis
(74) *Attorney, Agent, or Firm* — Shay Glenn LLP

(57) ABSTRACT

Methods and systems (including software) for creating a treatment plan to align a patient's teeth using a plurality of removable aligners to be worn in sequential stages. These methods and systems may generate a plurality of potential treatment plan variations. Each variation may be optimized to best address the user's treatment goals, as well as approximating as closely as possible an ideal or target final position.

27 Claims, 65 Drawing Sheets

(56) References Cited

U.S. PATENT DOCUMENTS

| | | | |
|---|---|---|---|
| 6,602,070 B2 * | 8/2003 | Miller | G16H 50/50 433/213 |
| 6,688,886 B2 | 2/2004 | Hughes et al. | |
| 6,726,478 B1 | 4/2004 | Isiderio et al. | |
| 6,767,208 B2 | 7/2004 | Kaza | |
| 6,783,360 B2 | 8/2004 | Chishti | |
| 7,063,532 B1 | 6/2006 | Jones et al. | |
| 7,074,038 B1 | 7/2006 | Miller | |
| 7,108,508 B2 | 9/2006 | Hedge et al. | |
| 7,160,107 B2 | 1/2007 | Kopelman et al. | |
| 7,293,988 B2 | 11/2007 | Wen | |
| 7,309,230 B2 | 12/2007 | Wen | |
| 7,357,634 B2 | 4/2008 | Knopp | |
| 7,555,403 B2 | 6/2009 | Kopelman et al. | |
| 7,736,147 B2 | 6/2010 | Kaza et al. | |
| 7,844,356 B2 | 11/2010 | Matov et al. | |
| 7,878,804 B2 | 2/2011 | Korytov et al. | |
| 7,942,672 B2 | 5/2011 | Kuo | |
| 8,044,954 B2 | 10/2011 | Kitching et al. | |
| 8,260,591 B2 | 9/2012 | Kass et al. | |
| 8,562,338 B2 | 10/2013 | Kitching et al. | |
| 8,591,225 B2 | 11/2013 | Wu et al. | |
| 8,788,285 B2 | 7/2014 | Kuo | |
| 8,930,219 B2 | 1/2015 | Trosien et al. | |
| 9,037,439 B2 | 5/2015 | Kuo et al. | |
| 9,060,829 B2 | 6/2015 | Sterental et al. | |
| 9,125,709 B2 | 9/2015 | Matty | |
| 9,364,296 B2 | 6/2016 | Kuo | |
| 10,342,638 B2 | 7/2019 | Kitching et al. | |
| 10,463,452 B2 | 11/2019 | Matov et al. | |
| 10,617,489 B2 | 4/2020 | Grove et al. | |
| 10,631,954 B1 * | 4/2020 | Raslambekov | A61C 7/002 |
| 10,722,328 B2 | 7/2020 | Velazquez et al. | |
| 10,758,322 B2 | 9/2020 | Pokotilov et al. | |
| 10,792,127 B2 | 10/2020 | Kopelman et al. | |
| 10,828,130 B2 | 11/2020 | Pokotilov et al. | |
| 10,835,349 B2 | 11/2020 | Cramer et al. | |
| 10,973,611 B2 | 4/2021 | Pokotilov et al. | |
| 10,996,813 B2 | 5/2021 | Makarenkova et al. | |
| 10,997,727 B2 | 5/2021 | Xue et al. | |
| 11,020,205 B2 | 6/2021 | Li et al. | |
| 11,020,206 B2 | 6/2021 | Shi et al. | |
| 11,026,766 B2 | 6/2021 | Chekh et al. | |
| 11,033,359 B2 | 6/2021 | Velazquez et al. | |
| 11,071,608 B2 | 7/2021 | Derakhshan et al. | |
| 11,096,763 B2 * | 8/2021 | Akopov | A61C 7/002 |
| 11,116,605 B2 | 9/2021 | Nyukhtikov et al. | |
| 11,151,753 B2 | 10/2021 | Gao et al. | |
| 2003/0008259 A1 | 1/2003 | Kuo et al. | |
| 2003/0143509 A1 | 7/2003 | Kopelman et al. | |
| 2003/0207227 A1 | 11/2003 | Abolfathi | |
| 2005/0182654 A1 | 8/2005 | Abolfathi et al. | |
| 2006/0127836 A1 | 6/2006 | Wen | |
| 2006/0127852 A1 | 6/2006 | Wen | |
| 2006/0127854 A1 | 6/2006 | Wen | |
| 2009/0191503 A1 * | 7/2009 | Matov | A61C 7/16 433/2 |
| 2010/0009308 A1 | 1/2010 | Wen et al. | |
| 2010/0068672 A1 | 3/2010 | Arjomand et al. | |
| 2010/0092907 A1 | 4/2010 | Knopp | |
| 2010/0167243 A1 | 7/2010 | Spiridonov et al. | |
| 2010/0324875 A1 | 12/2010 | Kalili | |
| 2016/0135925 A1 * | 5/2016 | Mason | A61C 7/002 703/2 |
| 2016/0242870 A1 | 8/2016 | Matov et al. | |
| 2017/0273760 A1 | 9/2017 | Morton et al. | |
| 2019/0029784 A1 | 1/2019 | Moalem et al. | |
| 2019/0053876 A1 | 2/2019 | Sterental et al. | |
| 2019/0192259 A1 | 6/2019 | Kopelman et al. | |
| 2019/0328487 A1 | 10/2019 | Levin et al. | |
| 2019/0328488 A1 | 10/2019 | Levin et al. | |
| 2019/0333622 A1 | 10/2019 | Levin et al. | |
| 2019/0343601 A1 | 11/2019 | Roschin et al. | |
| 2020/0000552 A1 | 1/2020 | Mednikov et al. | |
| 2020/0000554 A1 | 1/2020 | Makarenkova et al. | |
| 2020/0000555 A1 | 1/2020 | Yuryev et al. | |
| 2020/0085546 A1 | 3/2020 | Li et al. | |
| 2020/0107915 A1 | 4/2020 | Roschin et al. | |
| 2020/0155274 A1 | 5/2020 | Pimenov et al. | |
| 2020/0214800 A1 | 7/2020 | Matov et al. | |
| 2020/0297458 A1 | 9/2020 | Roschin et al. | |
| 2020/0306011 A1 | 10/2020 | Chekhonin et al. | |
| 2020/0306012 A1 | 10/2020 | Roschin et al. | |
| 2020/0315744 A1 | 10/2020 | Cramer | |
| 2020/0360109 A1 | 11/2020 | Gao et al. | |
| 2021/0073998 A1 | 3/2021 | Brown et al. | |
| 2021/0134436 A1 | 5/2021 | Meyer et al. | |
| 2021/0174477 A1 | 6/2021 | Shi et al. | |

\* cited by examiner (CONT. TO FIG. 6B)

Gather (e.g., from a remote site) an array of treatment plans specific to the patient's teeth, wherein each treatment plan in the array describes a set of sequential stages for orthodontic movement of the patient's teeth including a final stage. The treatment plans (e.g., 3 or more) may have different numbers of sequential stages. The array of treatment plans may include two or more treatment plans having different treatment properties.
721

Display on a screen, images of the final stage for each treatment plan of all or a subset of the treatment plans from the array of treatment plans.
723

Switch, in real time, between the images of the patient's teeth in the final stages for the different treatment plans within the array of treatment plans based on one or more user-selected controls on the screen.
725

Transmit a selected one of the treatment plans for fabrication after the user has chosen the selected one of the treatment plans displayed on the screen.
727

FIG. 7D

*invisalign*  Home page for Dr. Cimini    Dr. Profile | Logout  ?

Patients | Studies | Account | Store | Education | Support | Collaboration
                                                                    Promotions →
                                                           Invisalign Marketing Site →

Patient List > Patient File                                    Clinical Preferences →

📁 FULLX5242032, AUTOX5566                          Edit Patient Data | Archive Patient Date of Birth       Invisalign Option: Invisalign Full, Upper Arch
11/12/1978          Treatment Expiration Date: TBD
Patient #           Prior to this date, Additional Aligners are included in the
5522649             price, See Pricing, Terms and Conditions for Details.
Ship to Office      Clinical Conditions.
3397 Scranton-Carbondale
Highway
Suite 3

Additional Aligners →
                                                                     Replacement →
03/24/2017  ⓘ Action Required          ClinCheck     ?          Attachment Template →
Review ClinCheck treatment plan (03/24/2017)                             Warranty →
                                       ClinCheck Web
                                                                   Vivera Retainers →
03/24/2017                                                      Invisalign Retainers →
All materials received                                            Start New Treatment →

03/24/2017                                                      Latest Documents
Order received / Submission box received
                                                                ℞ Prescription Form
03/24/2017                              View Prescription ⇦     🔊 ClinCheck Plan
Prescription submitted
                                                                🖼 Treatment Overview ▷
invisalign Full
                                                                📷 Photos
                                                                ☐ X-Rays Print Molding Label →
                                                              Print Commercial Invoice →
                                                                        Print Forms →
                                                              Generate aligner schedule →

FIG. 8A invisalign  Prescription form N00100000 ∨

Prescription form                                                                    Assets                                              John T. ∨

[Edit]

& Patient type
  Teen

⊙ Tooth movement restrictions
  Teen                                    ⦿ PVS
                                            Treatment will be generated after PVS receiving.
☐ Eruption compensation                 Photos are mandatory.
  None
                                          ○ Intraoral Scan
∑ Protocol                              Treatment will be generated within 5 minutes after Rx submission
  Align default ☐ Impressions
  PVS ✓ All changes are saved automatically     Delete Rx form        [Back] [Generate treatment plans]

FIG. 8B

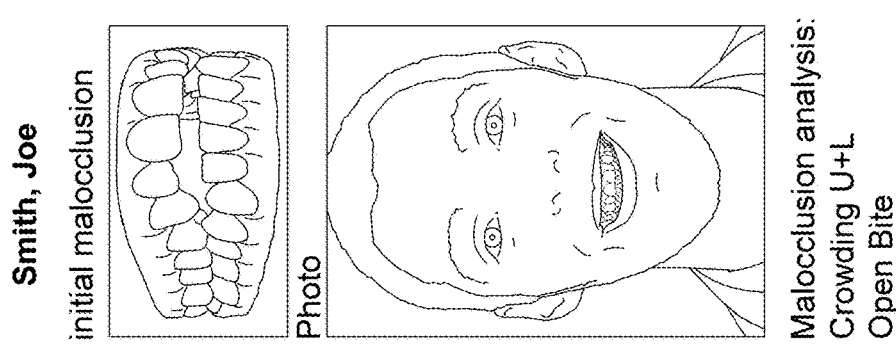
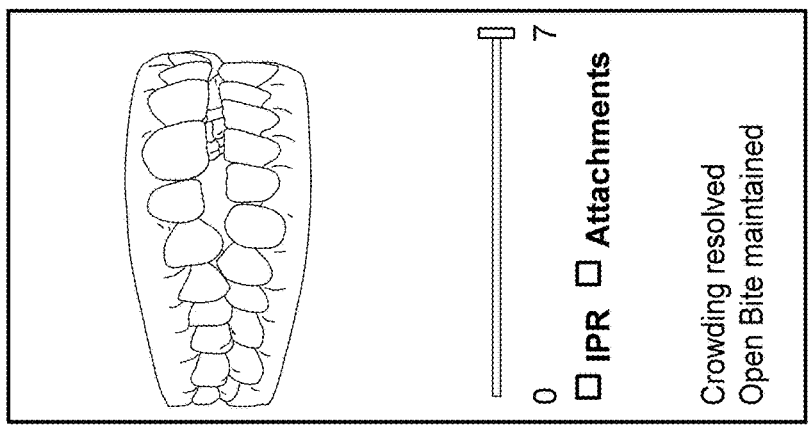
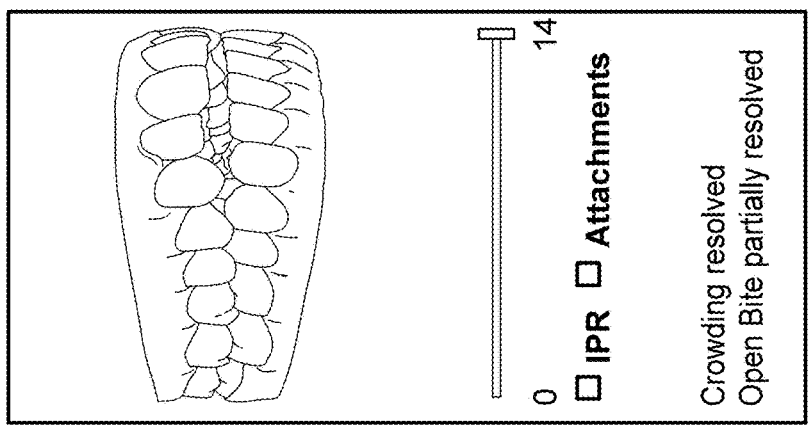
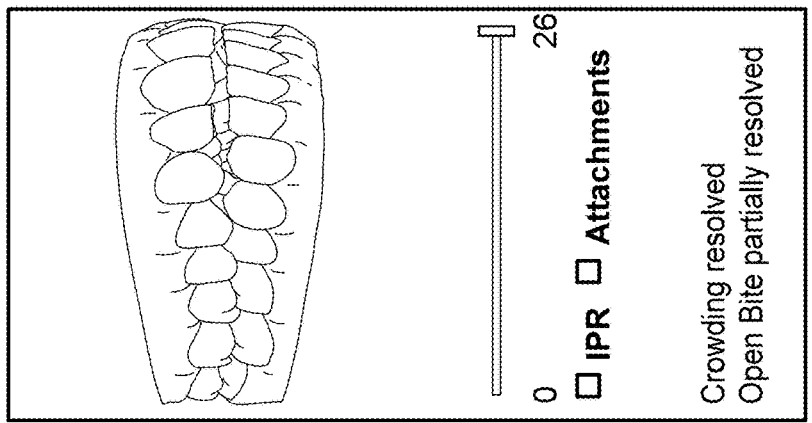
FIG. 9A

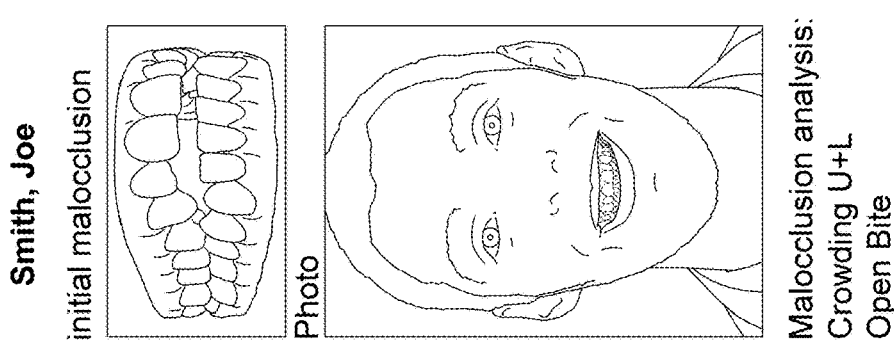
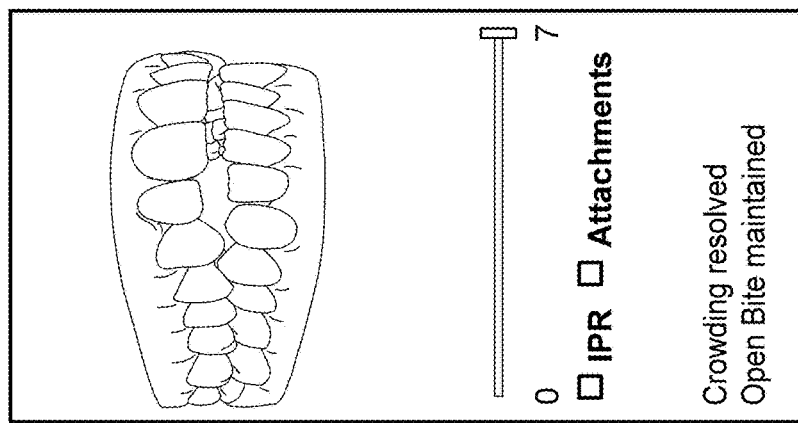
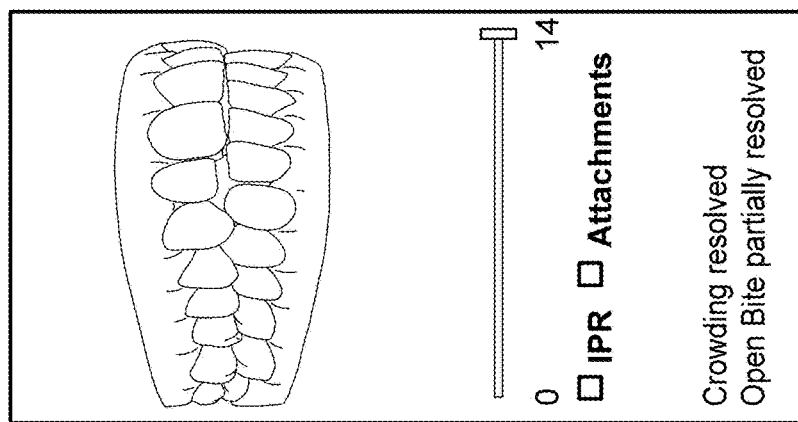
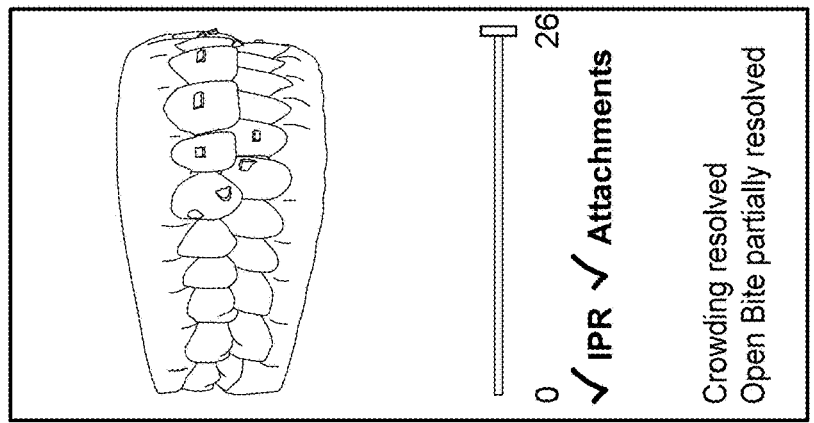
FIG. 9B

FIG. 9C

Submit modification - comments

← Back

ATTACH  IPR  SMILE  NUM

Go to consult mode

Product Name
Invisalign Go

Your preferences
✓ IPR
✓ Attachments

Instructions:
Do not move upper and lower 3rd molars
Do not retract upper teeth — 1105

Submit — 1107

Discard comments — 1109

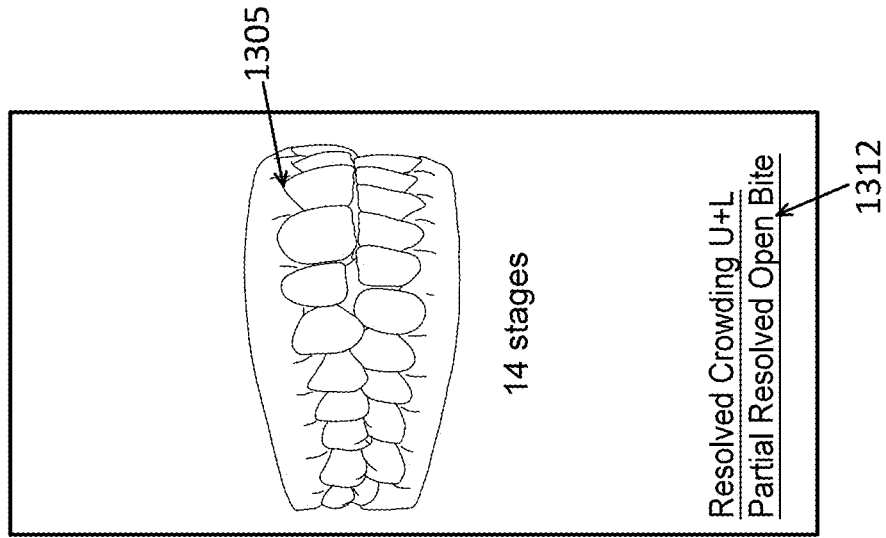
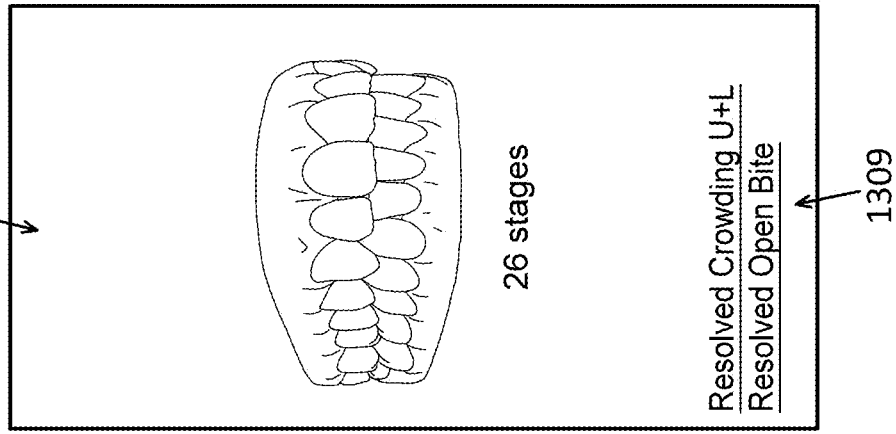
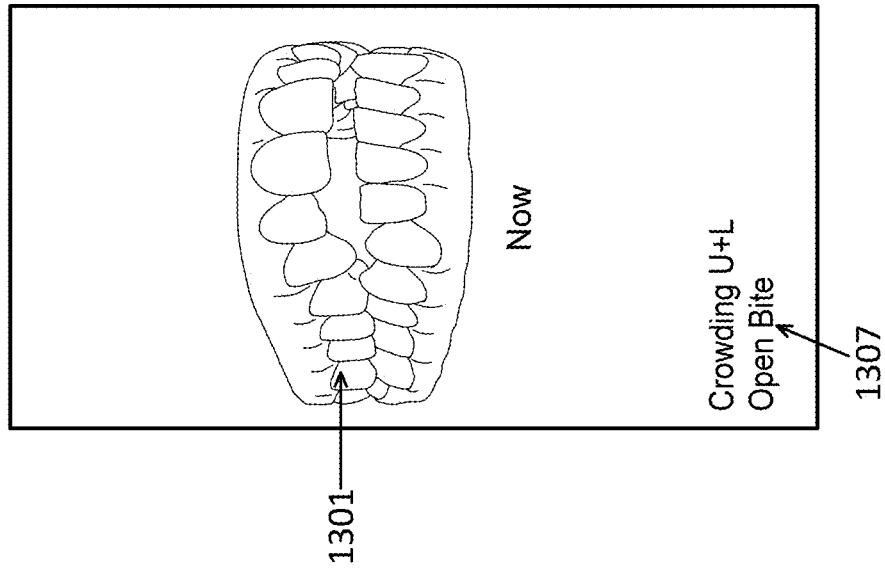
FIG. 13

Zoom in – 3d model
← Back
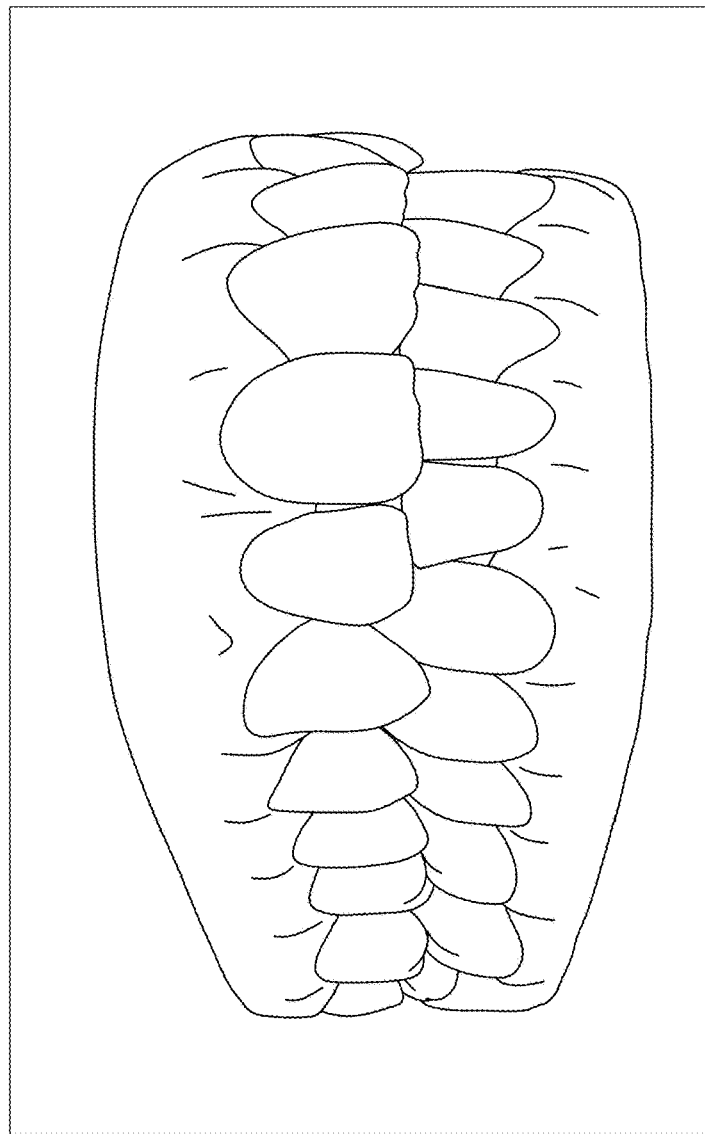
FIG. 14

**PROGRESSION OF MALOCCLUSION OVER TIME
SLIPPED CONTACT
MESIAL DRIFT**

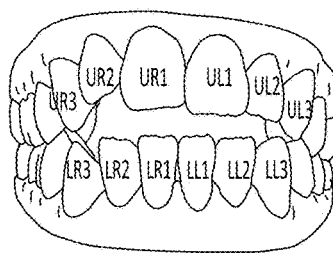
FIG. 16A
26 STAGES　　　　14 STAGES　　　　7 STAGES
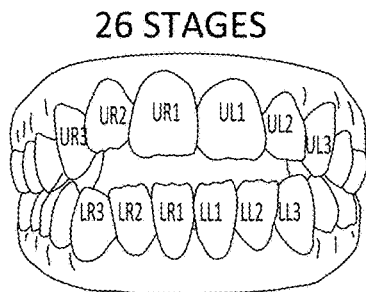 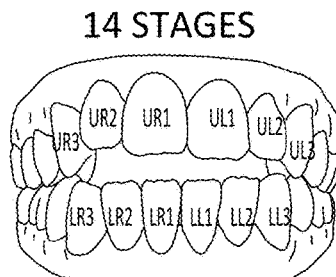 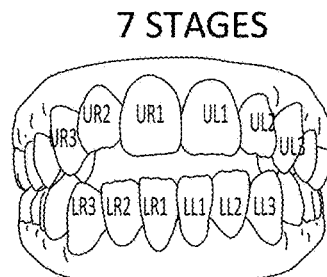
FIG. 16B　　　　FIG. 16C　　　　FIG. 16D
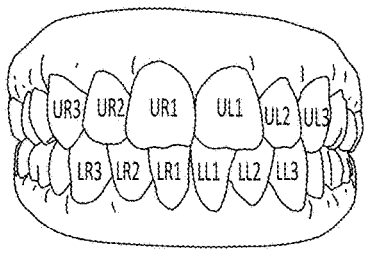 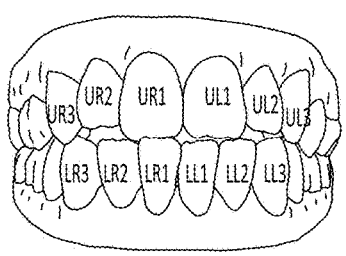 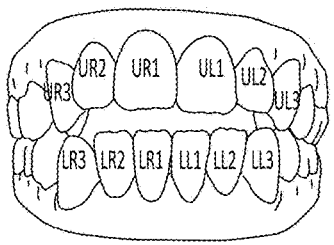
FIG. 16E　　　　FIG. 16F　　　　FIG. 16G
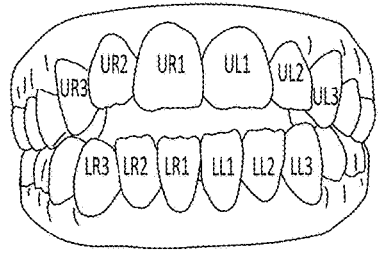 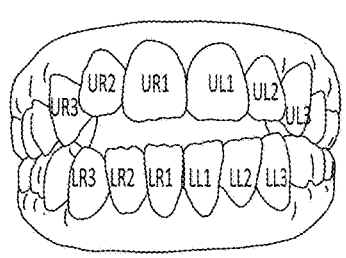 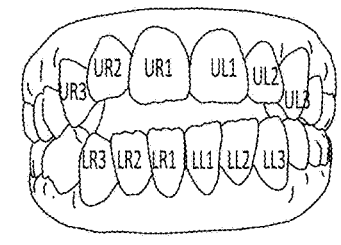
FIG. 16H　　　　FIG. 16I　　　　FIG. 16J
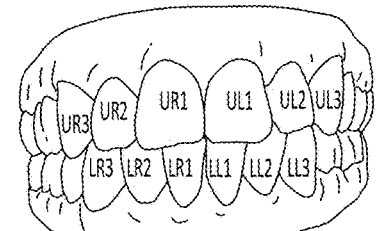 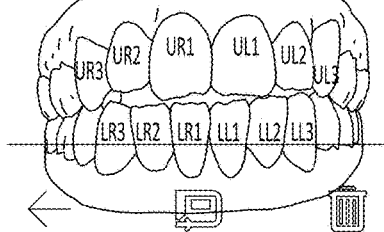 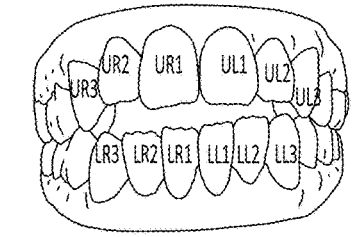
FIG. 16K　　　　FIG. 16L　　　　FIG. 16M

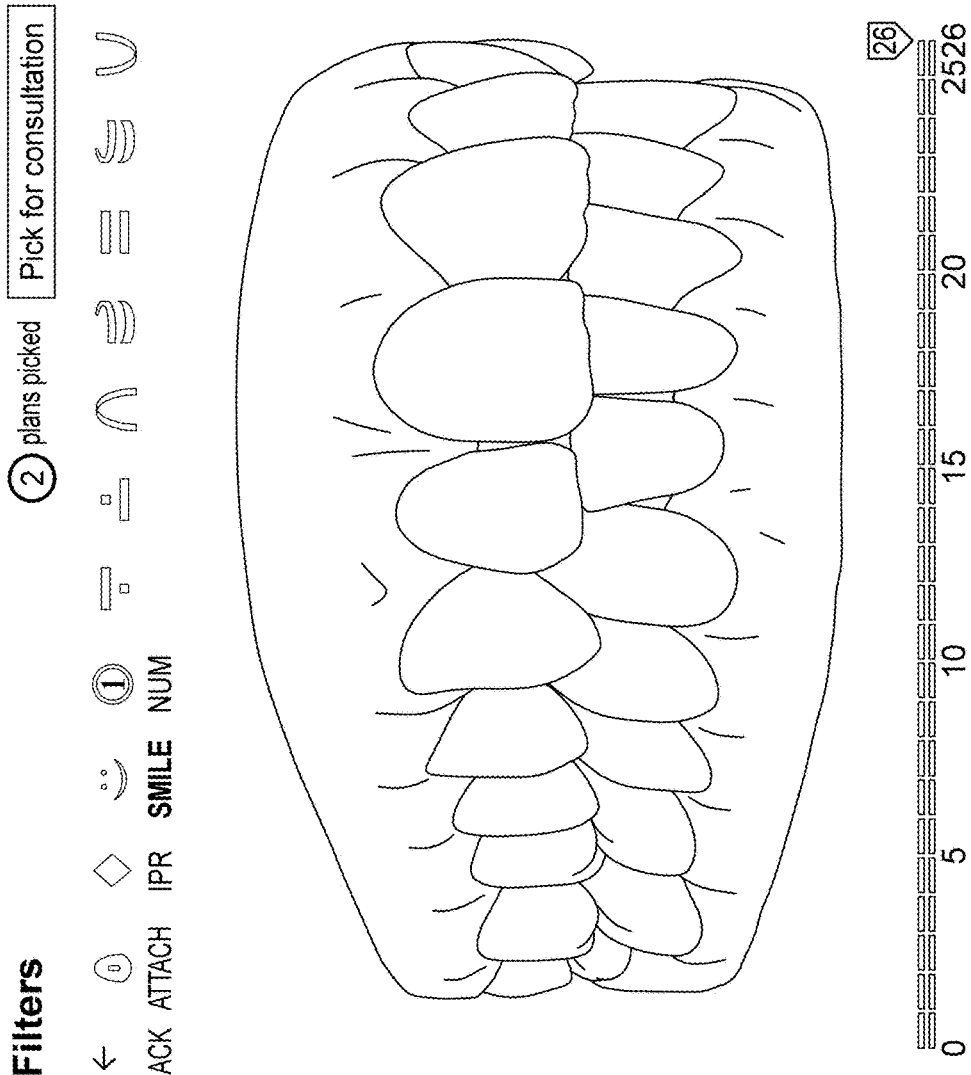
FIG. 17

Partial optimized setup

Comprehensive FiPos

Initial

| STG | 4.7 | 4.6 | 4.5 | 4.3 | 4.2 | 4.1 | 3.1 | 3.2 | 3.3 | 3.5 | 3.6 | 3.7 |
|---|---|---|---|---|---|---|---|---|---|---|---|---|
| 0 | .00 | .12 | 8.22 | .17 | .22 | .09 | .06 | .46 | 7.59 | .05 | .05 | |
| 1 | .00 | .12 | 8.08 | .38 | .22 | .09 | .06 | .46 | 7.59 | .05 | .05 | |
| 2 | .00 | .12 | 7.94 | .58 | .22 | .09 | .06 | .46 | 7.59 | .05 | .05 | |
| 3 | .00 | .12 | 7.80 | .79 | .22 | .09 | .06 | .46 | 7.59 | .05 | .05 | |
| 4 | .00 | .12 | 7.66 | .99 | .22 | .09 | .06 | .46 | 7.59 | .05 | .05 | |
| 5 | .00 | .12 | 7.53 | 1.20 | .22 | .09 | .06 | .46 | 7.59 | .05 | .05 | |
| 6 | .00 | .12 | 7.39 | 1.40 | .22 | .09 | .06 | .46 | 7.59 | .05 | .05 | |
| 7 | .00 | .12 | 7.26 | 1.60 | .22 | .09 | .06 | .46 | 7.59 | .05 | .05 | |
| 8 | .00 | .12 | 7.13 | 1.81 | .22 | .09 | .06 | .46 | 7.59 | .05 | .05 | |
| 9 | .00 | .12 | 7.00 | 2.02 | .22 | .09 | .06 | .46 | 7.59 | .05 | .05 | |
| 10 | .00 | .12 | 6.88 | 2.23 | .22 | .09 | .06 | .46 | 7.59 | .05 | .05 | |
| 11 | .00 | .12 | 6.76 | 2.43 | .22 | .09 | .06 | .46 | 7.59 | .05 | .05 | |
| 12 | .00 | .12 | 6.64 | 2.64 | .22 | .09 | .06 | .46 | 7.59 | .05 | .05 | |
| 13 | .00 | .12 | 6.52 | 2.85 | .22 | .09 | .06 | .46 | 7.59 | .05 | .05 | |
| 14 | .00 | .12 | 6.40 | 3.06 | .22 | .09 | .06 | .46 | 7.59 | .05 | .05 | |
| 15 | .00 | .12 | 6.28 | 3.27 | .22 | .09 | .06 | .46 | 7.59 | .05 | .05 | |
| 16 | .00 | .12 | 6.05 | 3.37 | .22 | .09 | .06 | .46 | 7.59 | .05 | .05 | |
| 17 | .00 | .12 | 5.82 | 3.47 | .22 | .09 | .06 | .46 | 7.59 | .05 | .05 | |
| 18 | .00 | .12 | 5.59 | 3.58 | .22 | .09 | .06 | .46 | 7.59 | .05 | .05 | |
| 19 | .00 | .12 | 5.36 | 3.69 | .22 | .09 | .06 | .46 | 7.59 | .05 | .05 | |
| 20 | .00 | .12 | 5.13 | 3.82 | .22 | .09 | .06 | .46 | 7.59 | .05 | .05 | |
| 21 | .00 | .12 | 4.90 | 3.94 | .22 | .09 | .06 | .46 | 7.59 | .05 | .05 | |
| 22 | .00 | .12 | 4.67 | 4.07 | .22 | .09 | .06 | .46 | 7.59 | .05 | .05 | |
| 23 | .00 | .12 | 4.44 | 4.20 | .22 | .09 | .06 | .46 | 7.59 | .05 | .05 | |
| 24 | .00 | .12 | 4.22 | 4.34 | .22 | .09 | .06 | .46 | 7.59 | .05 | .05 | |
| 25 | .00 | .12 | 3.99 | 4.48 | .22 | .09 | .06 | .46 | 7.59 | .05 | .05 | |
| 26 | .00 | .12 | 3.76 | 4.63 | .22 | .09 | .06 | .46 | 7.59 | .05 | .05 | |
| 27 | .00 | .12 | 3.54 | 4.78 | .22 | .09 | .06 | .46 | 7.59 | .05 | .05 | |
| 28 | .00 | .12 | 3.32 | 4.93 | .22 | .09 | .06 | .46 | 7.59 | .05 | .05 | |
| 29 | .00 | .12 | 3.10 | 5.08 | .22 | .09 | .06 | .46 | 7.59 | .05 | .05 | |
| 30 | .00 | .12 | 2.88 | 5.24 | .22 | .09 | .06 | .46 | 7.59 | .05 | .05 | |
| 31 | .00 | .12 | 2.66 | 5.40 | .22 | .09 | .06 | .46 | 7.59 | .05 | .05 | |
| 32 | .00 | .12 | 2.44 | 5.57 | .22 | .09 | .06 | .46 | 7.59 | .05 | .05 | |
| 33 | .00 | .12 | 2.22 | 5.73 | .22 | .09 | .06 | .46 | 7.59 | .05 | .05 | |
| 34 | .00 | .12 | 2.01 | 5.90 | .22 | .09 | .06 | .46 | 7.59 | .05 | .05 | |
| 35 | .00 | .12 | 1.79 | 6.07 | .22 | .09 | .06 | .46 | 7.59 | .05 | .05 | |
| 36 | .00 | .12 | 1.66 | 6.24 | .22 | .09 | .06 | .46 | 7.59 | .05 | .05 | |
| 37 | .00 | .12 | 1.52 | 6.41 | .22 | .09 | .06 | .46 | 7.59 | .05 | .05 | |
| 38 | .00 | .12 | 1.39 | 6.59 | .22 | .09 | .06 | .46 | 7.59 | .05 | .05 | |
| 39 | .00 | .12 | 1.26 | 6.76 | .22 | .09 | .06 | .46 | 7.59 | .05 | .05 | |
| 40 | .00 | .12 | 1.13 | 6.94 | .22 | .09 | .06 | .46 | 7.59 | .05 | .05 | |
| 41 | .00 | .12 | 1.00 | 7.12 | .22 | .09 | .06 | .46 | 7.59 | .05 | .05 | |
| 42 | .00 | .12 | .88 | 7.29 | .22 | .09 | .06 | .46 | 7.59 | .05 | .05 | |
| 43 | .00 | .12 | .77 | 7.47 | .22 | .09 | .06 | .46 | 7.59 | .05 | .05 | |
| 44 | .00 | .12 | .66 | 7.65 | .22 | .09 | .06 | .46 | 7.59 | .05 | .05 | |
| 45 | .00 | .12 | .53 | 7.82 | .22 | .09 | .06 | .46 | 7.59 | .05 | .05 | |
| 46 | | | | | | | | | | | | |

TRIANGULAR MESH

CAPSULES

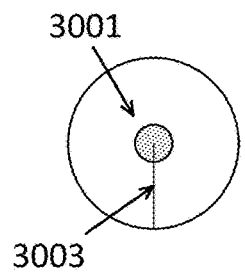
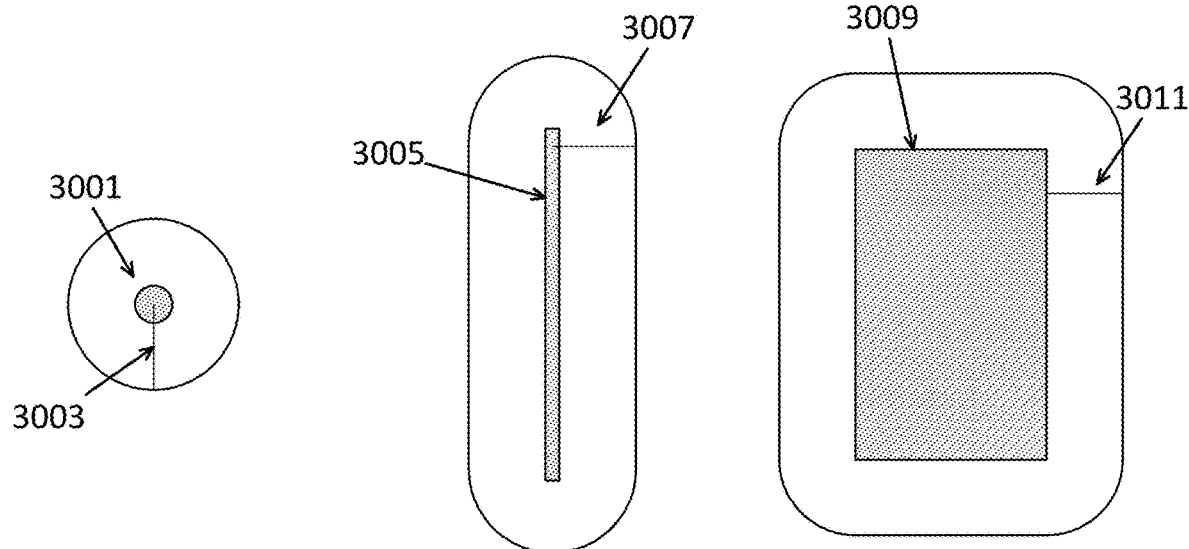
FIG. 30A          FIG. 30B          FIG. 30C
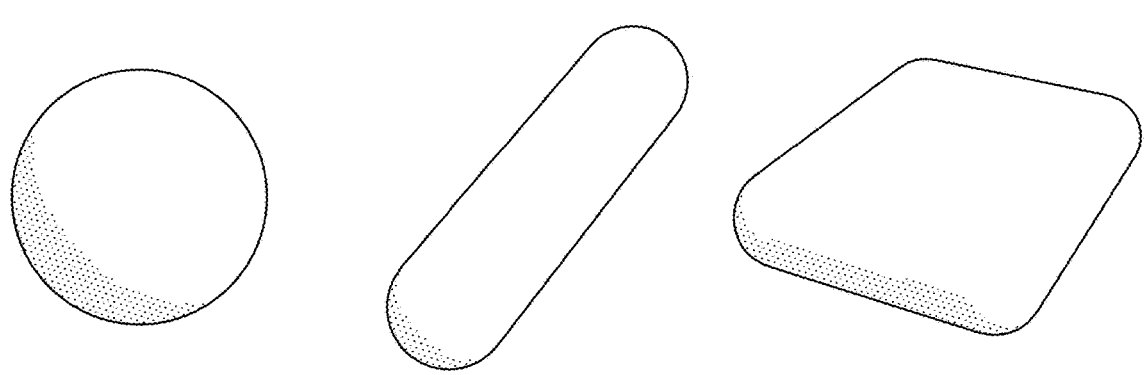
FIG. 31A          FIG. 31B          FIG. 31C

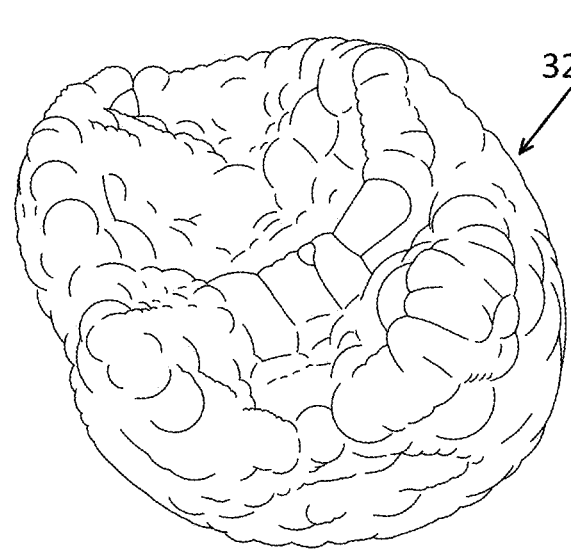
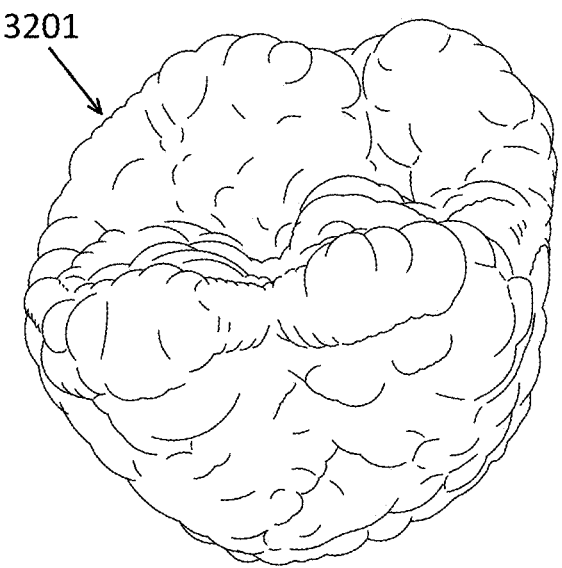
FIG. 32A   FIG. 32B
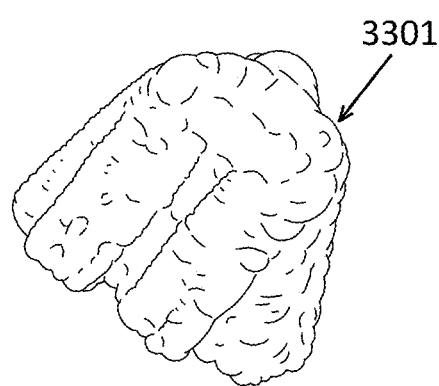
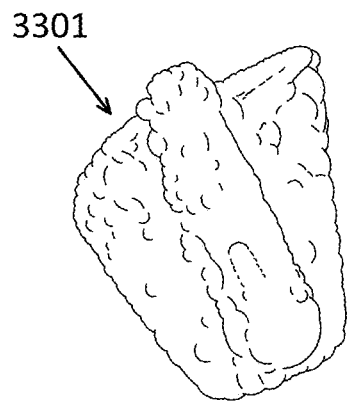
FIG. 33A   FIG. 33B

```
Procedure Distance(BoxA, BoxB, MinDist):
{
        // Boxes are too far from each other and cannot affect the value of MinDist
// skip tests for all pairs of capsules that belong to subtrees of BoxA and BoxB
If Distance(BoxA, BoxB) > MinDist
   return
If BoxA.IsLeaf And BoxB.IsLeaf
{
// Boxes cannot be skipped, find actual distance between capsules
// and update current value of MinDist
MinDist = min (MinDist, Distance (CapsuleA, Capsule B)
return
}
Foreach  BoxC: Child(BoxA)
{
  Foreach Box D: Child(BoxD)
  {
    // recursively check child subtrees
    Distance (BoxC, BoxD, MinDistance)
  }
}
}
```

FIG. 36

```
Procedure Distance(ShapeA, ShapeB, MinDist):
{
            Foreach CapsuleA: ShapeA
{
  Foreach CapsuleB: ShapeB
  {
    D = distance between CapsuleA and CapsuleB
    MinDist = min (MinDist, D)
  }
 }
}
```

|  | ATTACHMENTS: YES | ATTACHMENTS: POSTERIORS ONLY | ATTACHMENTS: NO |
|---|---|---|---|
| IPR USED | 1 | 5 | 9 |
| IPR NOT USED | 3 | 7 | 11 |

FIG. 43A

|  | ATTACHMENTS: YES | ATTACHMENTS: POSTERIORS ONLY | ATTACHMENTS: NO |
|---|---|---|---|
| IPR USED | 2 | 6 | 10 |
| IPR NOT USED | 4 | 8 | 12 |

FIG. 43B

TREATMENT PLANNING FOR ALIGNING A PATIENT'S TEETH

CROSS REFERENCE TO RELATED APPLICATIONS

This patent application is a continuation of U.S. patent application Ser. No. 17/406,071, filed Aug. 18, 2021, titled "METHODS OF MANUFACTURING DENTAL ALIGNERS," now U.S. Pat. No. 12,312,855, which is a continuation of U.S. patent application Ser. No. 16/178,491, filed Nov. 1, 2018, titled "AUTOMATIC TREATMENT PLANNING," now U.S. Pat. No. 11,096,763, which claims priority to U.S. Provisional Patent Application No. 62/580,432, filed on Nov. 1, 2017, titled "REAL-TIME, INTERACTIVE DENTAL TREATMENT PLANNING;" U.S. Provisional Patent Application No. 62/580,427, filed on Nov. 1, 2017, titled "AUTOMATIC TREATMENT PLANNING;" and U.S. Provisional Patent Application No. 62/692,551, filed on Jun. 29, 2018, titled "AUTOMATIC TREATMENT PLANNING;" each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Treatment planning for orthodontic treatment using a series of patient-removable appliances to reposition the teeth.

BACKGROUND

Orthodontic and dental treatments using a series of patient-removable appliances (e.g., "aligners") are very useful for treating patients, and in particular for treating malocclusions. Treatment planning is typically performed in conjunction with the dental professional (e.g., dentist, orthodontist, dental technician, etc.), by generating a model of the patient's teeth in a final configuration and then breaking the treatment plan into a number of intermediate stages (steps) corresponding to individual appliances that are worn sequentially. This process may be interactive, adjusting the staging and in some cases the final target position, based on constraints on the movement of the teeth and the dental professional's preferences. Once the final treatment plan is finalized, the series of aligners may be manufactured corresponding to the treatment planning.

This treatment planning process may include many manual steps that are complex and may require a high level of knowledge of orthodontic norms. Further, because the steps are performed in series, the process may require a substantial amount of time. Manual steps may include preparation of the model for digital planning, reviewing and modifying proposed treatment plans (including staging) and aligner features placement (which includes features placed either on a tooth or on an aligner itself). These steps may be performed before providing an initial treatment plan to a dental professional, who may then modify the plan further and send it back for additional processing to adjust the treatment plan, repeating (iterating) this process until a final treatment plan is completed and then provided to the patient.

The methods and apparatuses described herein may improve treatment planning, including potentially increasing the speed at which treatment plans may be completed, as well as providing greater choices and control to the dental professional, and allowing improved patient involvement in the treatment planning process.

SUMMARY OF THE DISCLOSURE

Described herein are orthodontic and/or dental treatment planning methods and apparatuses. In particular, described herein are methods of planning a dental and/or orthodontic treatment. Any of the methods and apparatuses described herein may pre-calculate a plurality of potential treatment plan variations including all of the staging and various, potentially alternative, final configurations and display them in parallel. A very large number of such plans may be generated at once (e.g., as a large set or array) quickly and reviewed in real time or near real-time. A treatment plan may include a plurality of different stages during which the patient's teeth are moved from an initial position to a final position; a dental aligner (e.g., a shell aligner) or other orthodontic device may be made to correspond to each stage, and worn in the sequence defined by the treatment plan to move the patients teeth from their initial position to a final position.

The methods and apparatuses described herein allow for the concurrent generation of a large number of treatment plan variations in which each variation is optimized to best address the dental professional's (and in some cases, the patient's) treatment goals, as well as approximating as closely as possible an ideal or target final position. Also described herein are orthodontic and/or dental treatment planning methods and apparatuses that allow a dental professional (e.g., a "user") and/or a patient to form, modify, and select a treatment plan from a plurality of different treatment plans, in real time.

For example, a dental professional may make a model (e.g., a digital model or scan, and/or a physical model, which may subsequently be digitized) and send it to a remote site (e.g., a laboratory) where multiple options for treatment plans may be generated. The model may be transmitted along with one or more of: treatment preferences from the dental professional specific to the patient, treatment preferences specific for the particular dental professional that may be applied to all patient's associated with that dental professional, and/or an indication of what clinical product(s) (e.g., orthodontic product) should be used to move the patient's teeth. This data may be used as inputs to generate the plurality of optional treatment plans, will be described in greater detail below. The resulting multiple treatment plans (which may collectively be referred to as an array of treatment plans, a set of treatment plans, or a collection of treatment plans or treatment plan variations) may then be transmitted back to the dental professional for interactive display, selection and/or modification by the dental professional and/or patient. Note that each treatment plan may have multiple stages, wherein at each stage of that treatment plan an aligner may be worn for a predetermined period of time; alternatively or additionally in some variations one or more stage may include orthodontic/dental manipulations (e.g., tooth removal, interproximal reduction, etc.) on the patient's teeth.

The methods and apparatuses described herein allow the rapid and creation of a large number of full treatment plans specific and customized to a patient setting froth an orthodontic and/or dental plan for beneficially modifying the subject's dentition, including in particular, moving (e.g., aligning, straightening, etc.) the patients teeth and/or resolving orthodontic issues specific to the patient. Traditionally, only a single orthodontic treatment plan was provided to a user and/or patient, in which the patient's dentition was modified from the patients initial dental position to a final dental position, often a comprehensive final position of the patient's teeth. In general a treatment plan may include a series of patient-removable appliances to reposition the teeth, and some indication of the duration of time each appliance ("aligner") is to be worn. At each stage of the treatment plan, one or more (or all) of the patient's teeth maybe moved relative to the prior stage, until the teeth are in a target configuration; once in the target configuration, the final stage(s) may optionally be a retainer (or multiple retainers) to maintain the target configuration for some retaining duration. Any number of stages may be used. In some variations the treatment plan may also indicate one or more dental/orthodontic procedures to be performed at that stage (e.g., interproximal reduction, tooth extraction, etc.).

The apparatuses (e.g., systems, devices, etc. including software, firmware and hardware), which may include treatment plan solvers, and methods described herein may rapidly generate a plurality of different treatment plans, each customized to the patient. These method and apparatuses may take into account the treatment preferences of the dental professional and/or patient, and/or the types and constraints of available appliances (aligners) when generating these treatment plans. Alternatively plans in which one or more of these parameters are different may be generated, allowing direct comparison between a large number of alternative plans. Typically generating even a single treatment plan has proven complex and time intensive. Manual techniques have been used for treatment planning and may require many hours or days to complete. Automation has also proven difficult, particularly when estimating or preventing collisions between teeth during the treatment. The methods and apparatuses described herein may provide an extremely fast and effective way to generate (and in some cases generate concurrently or nearly concurrently) a large number of different and therapeutically viable treatment plans. Treatment plans may be generated with no or minimal technician or dental professional oversight required. In some variations of the methods and apparatuses described herein more than 3 (e.g., more than 4, 5, 6, 7, 8, 9, 10, 12, 14, 16, 18, 20, 25, 30, 35, 40, 45, 50, 60, 70, 80, 90, 100, 125, 150, 175, 200, 250, 300, 350, 400, 500, etc.) complete treatment plans, each including a variety of stages and corresponding tooth position and/or appliance (e.g., aligner) configuration (in some variations the tooth position at each stage may be used to generate a dental appliance).

For example, described herein are automated methods of creating a plurality of dental/orthodontic treatment plans, as well as devices for performing them (e.g., treatment plan solvers). An automated method of creating a plurality of variations of treatment plans to align a patient's teeth using a plurality of removable aligners to be worn in sequential stages may include: (a) specifying a set of treatment preferences and a set of treatment details (the treatment preferences and treatment details may be automatically or manually specified); (b) automatically determining a treatment plan based on the specified treatment preferences and treatment details, by: collecting (e.g., receiving, forming, gathering, downloading, and/or accessing), in a processor: a digital model of a patient's teeth, and accessing, by the processor, the set of treatment preferences, a comprehensive final position of the patient's teeth, and the set of treatment details; selecting a plurality of numerically expressed treatment targets from a memory accessible to the processor, based on the set of treatment details, the set of treatment preferences and the comprehensive final position of the patient's teeth; combining the plurality of numerically expressed treatment targets to form a single numerical function; selecting a plurality of numeric limits on the single numerical function based on the set treatment preferences; minimizing the single numerical function subject to the plurality of numeric limits to get a solution vector including all stages forming the treatment plan; and mapping the solution vector to a treatment plan, wherein the treatment plan includes a final tooth position that is different from the comprehensive final position of the patient's teeth (c) adding the treatment plan to an array of treatment plans; and (d) modifying one or more of the treatment details or treatment preferences and repeating steps (b)-(d) at least once. The method may also include adding metadata identifying the treatment details or treatment preferences to each treatment plan so that the array of treatment plans includes the identifying metadata. The metadata does not need to indicate all of the treatment details or treatment preference information, but may include just a subset of it, such as just those parameters that are different from the other treatment plans (e.g., number of stages, use of IPR, etc.).

In any of the methods and apparatuses described herein, minimizing the single numerical function subject to the plurality of numeric limits to get a solution vector including all stages forming the treatment plan may include estimating collisions between adjacent teeth. Thus, any of these apparatuses may include a collision detector, and particular a collision detector that determines the magnitude and/or velocity of collisions (or separation, which is negative collision) between teeth. The use of very rapid collision detection/detectors may enhance the rate and efficiency of the methods and apparatuses for treatment planning described herein; automated collision detection methods and systems (collision detectors) are also described in greater detail herein.

In some variations the method may also include an automated analysis of the final stage tooth position to determine the amount or level of correction of the patient's malocclusions achieved. This treatment outcome information may be added, e.g., as metadata, to the array of treatment plans.

Also described herein are methods and apparatuses for generating or translating user-specific treatment preferences. Dental professionals (e.g., users) may provide comments, requests and feedback on treatment plans across many cases. The methods and apparatuses described herein may interpret these comments, request and feedback, as treatment preferences. For example, these treatment preferences may include preferences with respect to modifying the patient's teeth (e.g., IPR, including which teeth to perform IPR on, what stage of treatment to perform IPR, etc.), the use of attachments (to use/not to use, where to place them, when to use them), and the like. The methods and apparatuses described herein may build and use a database of such user-specific treatment preferences. This database may be updated and modified as the user performs additional cases. Further, this database may be accessed to generate a treatment plan (or an array of treatment plans), as described herein.

For example, an automated and customized method for creating an orthodontic treatment plan of a patient's teeth for a specified dental professional may include: collecting (e.g., receiving, forming, gathering, downloading, and/or accessing), in a treatment plan optimizing engine (e.g., a processor), a set of combined treatment preferences specific to the specified dental professional, wherein the set of combined treatment preferences comprises a first set of rules converted from a set of textual instructions from the specified dental professional into a domain-specific language specific to the specified dental professional, further wherein the textual instructions comprise unscripted instructions, and a second set of rules converted from a set of scripted instructions from the specified dental professional, wherein the scripted instructions comprise responses from a script of predefined choices; receiving, in the treatment plan optimizing engine, a digital model of the patient's teeth; and generating, with the treatment plan optimizing engine, a treatment plan for the patient's teeth using the set of combined treatment preferences and the digital model of the patient's teeth. The different treatment properties may comprise one or more of: interproximal reduction (IRR), extraction, and aligner attachments.

The scripted instructions from the specified dental professional may be specific to the patient's teeth. The textual instructions may be specific to the patient's teeth, and/or the textual instructions may be extracted from a plurality of different prior cases by the specified dental professional.

The textual instructions may comprise instructions on one or more of, for example, staging of interproximal reduction and positions of attachments. Any other treatment preference may be included as a textural instruction.

In general, any of the methods may include updating the domain-specific language specific to the specified dental professional, and/or storing the domain-specific language specific to the specified dental professional in a remote database accessible by the treatment plan optimizing engine. Any of these methods may include automatically generating the domain-specific language specific to the specified dental professional, or manually converting textual instructions into the domain-specific language specific to the specified dental professional.

Any of these methods may include identifying the specified dental professional to the treatment plan optimizing engine; for example, the dental professional may be identified by an identifier (dental professional identifier) such as name (last, first, etc.), practice name, number, etc. The identifiers described herein may uniquely identify the dental professional.

As described in greater detail herein, typically generating the treatment plan comprises determining a final position of the patient's teeth, and determining each of a plurality of stages of tooth movement based on the combined treatment preferences, wherein each stage comprises a dental aligner.

For example, described herein are automated and customized method for creating an orthodontic treatment plan of a patient's teeth for a specified dental professional, the method comprising: receiving, in a processor, a set of scripted instructions from a specified dental professional, wherein the scripted instructions comprise responses from a script of predefined choices; receiving in the processor, a set of textual instructions from the specified dental professional, wherein the textual instructions comprise unscripted instructions; converting the set of textual instructions into a domain-specific language specific to the specified dental professional, wherein the domain-specific language comprises a first set of rules; converting the set of scripted instructions into a second set of rules; combining the first set or rules and the second set of rules into a set of combined treatment preferences; and passing the set of combined treatment preferences to a treatment plan optimizing engine, wherein the treatment plan optimizing engine generates a treatment plan using the combined treatment preferences.

Any of these methods may also include accessing, by the processor, a database of the domain-specific language corresponding to the specified dental professional.

Any of the methods described herein may be performed by an apparatus configured and/or adapted to perform them. For example, also described herein are non-transitory computer-readable storage media having stored thereon, computer-executable instructions that, when executed by a computer, cause the computer to automatically create an orthodontic treatment plan of a patient's teeth customized for a specified dental professional by: receiving, in a treatment plan optimizing engine, a set of combined treatment preferences specific to the specified dental professional, wherein the set of combined treatment preferences comprises a first set of rules converted from a set of textual instructions from the specified dental professional into a domain-specific language specific to the specified dental professional, further wherein the textual instructions comprise unscripted instructions, and a second set of rules converted from a set of scripted instructions from the specified dental professional, wherein the scripted instructions comprise responses from a script of predefined choices; receiving, in the treatment plan optimizing engine, a digital model of the patient's teeth; and generating, with the treatment plan optimizing engine, a treatment plan for the patient's teeth using the set of combined treatment preferences and the digital model of the patient's teeth.

As mentioned above, also described herein are methods and apparatuses (e.g., systems, devices, etc., including software) for automatically detecting and/or estimating collisions between teeth. These methods and apparatuses may provide an approximation of the magnitude and/or velocity of collisions between teeth. The magnitude and velocity of a collision may be expressed as a vector or a scalar value or values. The velocity may be velocity in each of a plurality of axes, such as three translational axes (x, y, z) and three rotational axes (pitch, roll, yaw). In some variations the magnitude and velocity of collisions may be determined between all adjacent pairs of teeth. The magnitude of a collision may be positive (e.g., indicating the depth of collision) or negative (indicating separation or spacing between teeth).

Although the automated collision detection systems and methods described herein may be particularly useful as part of automated method for generating treatment plans (e.g., as part of a treatment plan solver), they are not limited to this. It should be understood that the methods and apparatuses described herein may also be used independently, or as part of any other method or apparatus that may benefit from automatic and rapid detection of collision between two or more teeth.

For example, a method of automatically determining collisions between adjacent teeth may include: forming a digital model of a surface for each tooth of a plurality of a patient's teeth by automatically packing a plurality of 3D shapes to approximate the surface for each tooth, wherein the 3D shapes each have a core that is a line segment or a closed plane figure and an outer surface that is a constant radius from the core; forming, for the digital model of the surface for each tooth, a hierarchy of bounding boxes enclosing the plurality of 3D shapes; measuring, in the collisions detector, a magnitude and a velocity of a collision between adjacent teeth when the plurality of the patient's teeth are in a set of tooth positions by identifying colliding bounding boxes and determining the spacing or overlap between the 3D shapes bound by the colliding bounding boxes; and outputting the magnitude and velocity of the collision between adjacent teeth corresponding to the set of tooth positions.

Any of the methods for automatically determining collisions may also include collection (e.g., receiving, downloading, accessing, etc.) a set of tooth positions. The tooth positions may correspond to the positions of the teeth in space. In some variations the teeth may be arranged in a coordinate system (e.g., x, y, z) allowing relative positions of the teeth to be understood.

In general, in any of the methods and apparatuses for automatically determining collisions (e.g., collision detectors) described herein, one or more surfaces of the patient's teeth may be filled with the 3D shapes. As used herein a 3D shape may refer to a shape having a core that is a line or planar (including closed planar) figure, and an outer 3D surface surrounding and extending from the core by a set radius, r. In some variations the 3D shapes are capsules, which have a core that is a line segment extending some length, L. The body of the 3D shape (capsule body) is elongated but rounded at the end, having semi-spherical ends. Any appropriate 3D shape, or combination of 3D shapes may be used. These 3D shapes may exclude spheres, which typically have a point at the core, surrounded by a surface at an outer radius. 3D shapes having a core that is a line or a plane figure, and particularly closed plane figures (such as rectangles, circles, etc.) that form shapes having both linear and convex outer surfaces may work much better than simple spheres when filling tooth surfaces, which may be concave, convex, as well as flat in some regions.

In general, when automatically determining collision between two teeth, each of the two teeth being processed may be divided into portions, so that just those surfaces of the portions of the teeth that face each other need to be filled/modeled with the 3D shapes (e.g., capsules). In some variations the teeth may be first divided in half, into a left half and a right half, and only the sides of the teeth that face each other need to be processed. Thus, forming the digital model of the surface for each tooth may include separately forming a left side and a right side of each tooth. Thus, measuring the magnitude and velocity of the collision between adjacent teeth may comprise identifying collisions between adjacent left sides and right sides of the adjacent teeth.

In any of the collision detection methods and apparatuses described herein, forming the digital surface of the surface for each tooth may include automatically packing the plurality of 3D shapes to approximate the surface. In some the surface (and/or the entire tooth volume, or a portion of the tooth volume, such as the left side/right side) may be modeled by packing with a plurality of 3D shapes (e.g., capsules) that are all the same shape and size, or different shapes and/or different size 3D shapes may be used. In processing to determine collisions (and/or spacing) between adjacent teeth, the closet capsules between each of the two teeth may be determined by bounding boxes and one or more numeric methods may be used to solve for the collision magnitude (which may be overlap/collision and be a positive magnitude value or may be spacing and be a negative collision magnitude).

Thus, and of the methods and apparatuses for collision detection described herein may also include forming a hierarchy of bounding boxes around the 3D shapes (e.g., capsules) forming the surface of the first tooth and a second hierarchy of bounding boxes may be determined around the 3D shapes (e.g., capsules) forming the surface of the second tooth that is adjacent to the first tooth. The use of a tiered hierarchy of bounding boxes around the 3D shapes forming the surfaces allows for a computationally rapid determination of which of the bounding boxes in the hierarchy do and do not overlap/collide. At the lowest tier of the hierarchy each bounding box encloses a single 3D shape; each subsequent tier bound two adjacent bounding boxes, until the highest tier, which bounds all of the bounding boxes around all of the 3D shapes. Forming the hierarchy of bounding boxes may comprises, for example, forming a hierarchy in which bounding boxes of a lowest tier of the hierarchy each enclose a single 3D shape, subsequent tiers of the hierarchy each enclose adjacent bounding boxes or groups of bounding boxes, and a highest tier of the hierarchy encloses all of the bounding boxes around the 3D shapes forming the surface. When comparing the hierarchy of bounding boxes, the comparison may start at the top of the hierarchy; if the top-tier hierarchy for each adjacent tooth surface does not collide, then none of the bounding boxes in the hierarchy will collide. Each branch of the first hierarchy (e.g., corresponding to the first tooth surface) may be compared with each branch of the second hierarchy (e.g., corresponding to the second tooth surface) starting from the top tier and working down the hierarchy tiers; at any tier that there is no overlap (e.g., collision, which may be detected by measuring the shortest distance between the bounding boxes at that tier) between two branches, no further lower-tiered branches need to be examined. Once the lowest tier has been reached, the 3D shapes in the colliding bounding boxes may then be used to determine the collision magnitude and velocity.

The magnitude of the collision between adjacent teeth may be measured by, for example, determining the spacing or overlap between the 3D shapes bound by the colliding bounding boxes to get the magnitude of the collision. As just mentioned, measuring the magnitude and velocity of the collision between adjacent teeth may include starting from a top tier of the hierarchy of bounding boxes and proceeding down the tiers to the lowest tier of the hierarchy of bounding boxes corresponding to each adjacent tooth, comparing the branches at each tier between the two adjacent teeth in order to identify colliding bounding boxes at the lowest tier of the hierarchy of bounding boxes. Once the colliding bounding boxes are determined, the shortest distance (the maximum overlap) between the two 3D shapes (e.g., capsules) may be computationally determined.

The velocity of the collision between adjacent teeth may be measured by 'jittering' one or both of the colliding teeth relative to the other; for example, one of the 3D shape-filled teeth (or portion of the tooth) may be moved very slightly (e.g., between 0.001-0.0001 inch) in each of one of the spatial axes (e.g., x, y, z, pitch, roll, yaw) and determining the change in the collision after each sequential movement. For example, by sequentially adjusting a position of a first 3D shape of the adjacent teeth by a small predetermined amount in each of a plurality of axes of the first tooth and determining the change in spacing or overlap between the 3D shapes bound by the bounding boxes to get the velocity of the collision for each of the corresponding axes. The change in collision/spacing magnitude following each change may be expressed for that axes as the velocity (the time to achieve the change may be assumed to be a set value, e.g., 1).

The velocity may be expressed as a single vector (e.g., the x, y, z direction) and/or rotation; in some variations the velocity may be expressed in each of the axes (three spatial and 3 rotational). Alternatively, in some variations, only the three spatial (or three rotational) axes are examined. The resulting collision magnitude and velocity may be output, e.g., by outputting the magnitude and the velocity for each of three spatial and three rotational axes. The output (magnitude, velocity or both magnitude and velocity) may be passed to the treatment planning solver, or to any other system that the collision detector is part of, and/or it may be output (e.g., displayed, stored, transmitted, etc.) for independent use.

Also described herein are systems for automatically detecting collisions between teeth. These systems may be referred to as collision detectors and may include, for example: one or more processors; and a memory coupled to the one or more processors, the memory configured to store computer-program instructions, that, when executed by the one or more processors, perform a computer-implemented method comprising: forming a digital model of a surface for each tooth of a plurality of a patient's teeth by automatically packing a plurality of 3D shapes to approximate the surface for each tooth, wherein the 3D shapes each have a core that is a line segment or a closed plane figure and an outer surface that is a constant radius from the core; forming, for the digital model of the surface for each tooth, a hierarchy of bounding boxes enclosing the plurality of 3D shapes; measuring, in the collisions detector, a magnitude and a velocity of a collision between adjacent teeth when the plurality of the patient's teeth are in a set of tooth positions by identifying colliding bounding boxes and determining the spacing or overlap between the 3D shapes bound by the colliding bounding boxes; and outputting the magnitude and velocity of the collision between adjacent teeth corresponding to the set of tooth positions.

As mentioned above, any of these method of detecting collisions and/or collision detectors may be included as part of a system or method for automatically creating an orthodontic treatment plan of a patient. For example, a method of automatically creating an orthodontic treatment plan for a patient may include: forming a digital model of a surface for each tooth of a plurality of a patient's teeth by packing a plurality of 3D shapes to approximate the surface for each tooth, wherein the 3D shapes each have a core that is a line segment or a closed plane figure and an outer surface that is a constant radius from the core; forming, for the surface for each tooth of the plurality of the patient's teeth, a hierarchy of bounding boxes enclosing the plurality of 3D shapes; passing a set of tooth positions for the plurality of the patient's teeth from a treatment plan solver to a collision detector; measuring, in the collisions detector, a magnitude and a velocity of a collision between adjacent teeth when the plurality of the patient's teeth are in the set of tooth positions by identifying colliding bounding boxes and determining the spacing or overlap between the 3D shapes bound by the colliding bounding boxes; and passing the magnitude and velocity of the collision between adjacent teeth corresponding to the set of tooth positions to the treatment plan solver; and outputting, from the treatment plan solver, one or more orthodontic treatment plans comprising a series of dental appliances for moving the patient's teeth.

A method of automatically creating an orthodontic treatment plan of a patient may include: collecting a digital model of a plurality of the patient's teeth, wherein each tooth of the digital model is segmented; automatically packing a plurality of 3D shapes to approximate a surface for each tooth of the digital model, wherein the 3D shapes each have a core that is a line segment or a closed plane figure and an outer surface that is a constant radius from the core; forming, for the surface for each tooth of the digital model, a hierarchy of bounding boxes enclosing the plurality of 3D shapes, wherein for each surface for each tooth of the digital model, bounding boxes of a lowest tier of the hierarchy each enclose a single 3D shape, subsequent tiers of the hierarchy each enclose adjacent bounding boxes or groups of bounding boxes, and a highest tier of the hierarchy encloses all of the bounding boxes around the 3D shapes forming the surface; passing a set of tooth positions for the plurality of the patient's teeth from a treatment plan solver to a collision detector; measuring, in the collisions detector, a magnitude and a velocity of a collision between adjacent teeth when the plurality of the patient's teeth are in the set of tooth positions by identifying colliding bounding boxes at the lowest tier of the hierarchy for each of the adjacent teeth, determining the spacing or overlap between the 3D shapes bound by the bounding boxes to get the magnitude of the collision, and sequentially adjusting a position of a first tooth of the adjacent teeth by a small predetermined amount in each of a plurality of axes of the first tooth and determining the change in spacing or overlap between the 3D shapes bound by the bounding boxes to get the velocity of the collision for each of the corresponding axes; and outputting the magnitude and velocity of the collision between adjacent teeth corresponding to the set of tooth positions to the solver; outputting, from the solver, one or more orthodontic treatment plans comprising a series of dental appliances for moving the patient's teeth.

A system for automatically creating an orthodontic treatment plan of a patient may include: one or more processors; a treatment plan solver operating on the one or more processors; a collision detector operating on the one or more processors; and a memory coupled to the one or more processors, the memory configured to store computer-program instructions, that, when executed by the one or more processors, perform a computer-implemented method comprising: forming a digital model of a surface for each tooth of a plurality of a patient's teeth by packing a plurality of 3D shapes to approximate the surface for each tooth, wherein the 3D shapes each have a core that is a line segment or a closed plane figure and an outer surface that is a constant radius from the core; forming, for the surface for each tooth of the plurality of the patient's teeth, a hierarchy of bounding boxes enclosing the plurality of 3D shapes; passing a set of tooth positions for the plurality of the patient's teeth from a treatment plan solver to a collision detector; measuring, in the collisions detector, a magnitude and a velocity of a collision between adjacent teeth when the plurality of the patient's teeth are in the set of tooth positions by identifying colliding bounding boxes and determining the spacing or overlap between the 3D shapes bound by the colliding bounding boxes; passing the magnitude and velocity of the collision between adjacent teeth corresponding to the set of tooth positions to the treatment plan solver; and outputting, from the treatment plan solver, one or more orthodontic treatment plans comprising a series of dental appliances for moving the patient's teeth.

In any of these methods and systems, the collision detector may be repeatedly (including iteratively) invoked. For example, in any of these methods and apparatuses, prior to outputting the one or more treatment plans, the steps of passing the set of tooth positions for the plurality of the patient's teeth to the collision detector, measuring the magnitude and velocity of collisions between adjacent teeth and passing the magnitude and velocity of collisions are repeated for a plurality of different sets of tooth positions, wherein the treatment plan solver generates the different sets of tooth positions.

In any of the methods and systems of generating treatment plans described herein, the treatment plan solver may generate the different sets of tooth positions while minimizing a numerical function subject to a plurality of numerical limits to get a solution vector including all stages of the one or more orthodontic treatment plans.

Also described herein are methods and apparatuses for rapid review and selection of a treatment plan, in real time, from among a large number of alternative treatment plans, including plans having different features, durations and final endpoints for the patient's dentition. Once selected/approved, the chosen treatment plan, including all of the staging information, may be transmitted for manufacture and delivery to the dental professional and/or patient. In particular, the methods and apparatuses described herein may permit the presentation of a variety of treatment plans having different treatment times (e.g., stages) and costs.

The array of treatment plans may include alternative variations of treatment plans that are presented to the user (e.g., dental professional, or in some cases, the patient) in parallel, and in real time. As mentioned, the treatment plan variations may include a variety of different stages, wherein each stage corresponds to a different aligner to be worn (e.g., for a predetermined period of time, such as for a day, a week, two weeks, etc.). The user may display side-by-side views, for real-time comparison, of different variations, and/or may swap between different variations, on a video device (computer, tablet, smartphone, etc.). The display may show the final position of the teeth predicted to result from the treatment and/or it may allow the user to review all of the different stages (including animations). The user may use one or more controls (e.g., buttons, sliders, tabs, etc.), which may be on the display to toggle between different treatment plans, including applying "filters" to show variations with or without a particular dental modification (e.g., interproximal reduction, tooth extraction, aligner attachments, etc.). Alternatively, the controls may be off of the display (e.g., on a keyboard, mouse, trackball, etc.).

As used herein, an array of treatment plans may refer to a group of treatment plans. The array of treatment plans may be unordered or ordered, and/or may be part of a single data structure or individual treatment plans may be maintained in separate data structures.

These methods and apparatus may also allow the user to modify any of the treatment plans. Many of the modifications made by the user may include variations of the treatment plans that are already pre-calculated and included in the array of treatment plans, thus the modifications may be made in real time by switching between the different treatment plan variations. The modifications may change one or more properties of the treatment and therefore the treatment plan. If the modifications go beyond the variations included in the array of treatment plans, the user may be notified, and the modified treatment plan may be transmitted back to the remote site for recalculation of the plurality of treatment plans (or the addition of new treatment plans to the array) to incorporate these changes, and the interactive method of forming and/or manufacturing the treatment plan may be continued with the new or enlarged array of treatment plan variations including the modifications requested by the user.

At the start of any of the methods described herein the dental professional may provide input, including patient-specific preferences or preferences specific to the dental professional (which may be applied to all of that dental professionals patients). Such preferences may include tooth movement restrictions (e.g., indicating which teeth should not move as part of the treatment), if interproximal reduction (IPR) should be used, and/or how, when during treatment or where to perform IPR, if attachments should be used, where (e.g., on which teeth) attachments should be placed if used, etc. In some variations, the method or apparatus may need just the name of the dental professional in order to invoke a predefined set of dental-professional specific preferences (e.g., looking up the dental professional's predefined preferences). The dental professional and/or patient may also specify which dental/orthodontic product(s) to use (e.g., which type of orthodontic product to use), which may correspond to properties that effect treatment, including the number of stages to use, the rate of movement of the teeth, etc. As with the dental-professional specific preferences, the method or apparatus may include a memory storing a database (e.g., a look-up table) of properties specific to each dental product.

In any of these methods and apparatuses, another input is typically a digital model of the patient's teeth. The digital model of the patient's teeth, as well as any of the user's patient-specific or user-specific preferences and/or the dental product(s) to be used may be used as inputs (e.g., sent to a remote site) to generate the array of treatment plans. The process of generating the treatment plans may be automated and may be fast (e.g., within a few seconds, minutes, or hours). Each treatment plan generated may include a final position, staging (e.g., a description of tooth movement directions along with a speed associated with each stage) and (optionally) a set of aligner features placed on each tooth to improve predictability of the treatment and ensure teeth movements occur. In generating each of these treatment plans, the final position of the teeth may be determined so as to address all or some of the patient's clinical conditions (e.g., malocclusions) such a crowding, bite issues, etc., and/or may approximate, as closely as possible, an ideal tooth position that may be achieved for the patient's teeth. Each treatment plan in the array may be specific to a set of properties correlated with the treatment plan and used to pre-calculate it. For example, each treatment plan may be generated using the particular set of treatment properties ("properties"). Properties may refer to modifications of the patient's teeth. For example, treatment plans may be pre-calculated for a particular number of stages/time of treatment, for the use or non-use of attachments on the teeth, for the use of attachment at particular locations, for the use of attachments of a particular type, for the use or non-use of IPR, for the use of IPR on specific sub-sets of teeth, for the use of IPR at specific stages, for the use or non-use of tooth extraction, etc., including all possible combinations of these properties. Each of the treatment plans are specific to the patient and may be independently generated for each set of properties using any of the techniques described herein. Thus, each treatment plan may be unique, and may have different tooth positions at any of the different stages and, importantly, may have different final stages. Although the treatment plans may have some generally similar, or nearly identical, tooth positions for some stages, they are typically generated independently of each other. For this reasons, these treatment plans may be referred to as partial treatment plans, since the final position of the treatment plan, and particularly those in which the maximum number of stages (and therefore the duration of the treatment), may not be the same as a comprehensive treatment plan, which resolves virtually all of a patient's orthodontic issues; instead, a partial treatment plan may partially resolve the orthodontic issues, or may resolve or partially resolve only some of these orthodontic issues The collection (e.g., array) of treatment plans may include a matrix of different treatment plan variations. For example, the various treatment plans may include variations having different treatment times (e.g., numbers of stages, corresponding to numbers of aligners in the treatment), and for each different treatment time, the final position may be optimized to address either or both any treatment goals, as well as approximating as closely as possible an ideal or target final position. The array of treatment plans may also include treatment plans that are variations of each of the plans having different treatment numbers, in which one or more particular treatment properties (including modifications to the patient's teeth) are included (e.g., with or without IPR, with or without extractions, etc.).

Methods and apparatuses described herein may include a display providing a simple interface for treatment planning. The user may modify any of the plans with a set of tools provided as controls (buttons, etc.) that may be present on the screen or any other input. The user may switch between different pre-calculated full treatment plans already in the array of treatment plans (e.g., by applying filters on/off to show variations such as with/without IPR, with/without extractions, with/without attachments, which attachments to place on which teeth, which teeth to use IPR, changing spacing distance between teeth, changing leveling strategy from "align by incisal edge" to "align by gingiva margins," etc.). As mentioned, in some cases, making modifications that are not covered by the pre-calculated treatment plan variations in the array of treatment plans may cause the method or apparatus to trigger generating of new treatment plans that replace or are added to the array of existing treatment plans and include the new modifications. In any of these methods and apparatuses, the treatment plans may be generated in a manner that ensures manufacturability of the plan as defined by ability to manufacture aligners based on the treatment plan without human intervention. In additional all of the treatment plans described herein may be generated so as not to worsen any orthodontic problem (e.g., malocclusion).

For example, described herein are apparatuses (e.g., systems) and methods for treatment planning that provide interactive treatment planning with a user (and/or a subject). In general, the apparatus and method may provide multiple, pre-calculated full treatment plans in which at least some of plans have different number of stages (e.g., different time to completion, wherein each stage is an aligner that may be worn for a predetermined, and continuous, amount of time), and many (if not all) of the treatment plans may have different final tooth positions that address some or all of the treatment goals. The plans may be annotated to include a description of the treatment plan, which may indicate the number of stages, the options present/absent, and the treatment goals met, treatment goals improved, or treatment goals left as-is. As described herein, these methods and apparatuses may take into account dental professional's preferences in order to maximize the treatment plans presented. For example the treatment plans that are initially presented from the array of treatment plans may be selected to have a higher probability of being acceptable to the dental professional (user), without requiring additional modifications. For example, when generating the treatment plans, the user's preferences for treatment of the specific patient (which may be based on a questionnaire and/or annotations provided by the user, as will be discussed in greater detail below, and/or treatment goals, weights on treatment goals, etc.), and/or general user preferences that may be applied to all of the user's patients (e.g., standard user practices, etc.) may be used along with the model of the patient's teeth (and in some variations the product to be used and/or characteristics of the product to be used) to generate the collection of treatment plans forming the array. Thus each array may be custom made for each individual user (e.g., dental professional) and specific to the patient. In addition, the method and apparatus may select which treatment plans to present initially based on predetermined or set user preferences.

Described herein are methods and apparatuses for the display and selection of multiple treatment plans having different endpoints and numbers of treatment stages. For example, a method of manufacturing a series of aligners for a patient's teeth may include: collecting (e.g., receiving, forming, gathering, downloading, and/or accessing, from a remote site or a local site, and may be collected, for example, in a processor to be accessed by the user), an array of treatment plans specific to the patient's teeth, wherein each treatment plan in the array describes a set of sequential stages for orthodontic movement of the patient's teeth including a final stage, further wherein at least three of the treatment plans have different numbers of sequential stages, and further wherein the array of treatment plans comprises two or more treatment plans having different treatment properties; displaying on a screen, images of the teeth at the final stage for each treatment plan of a subset of the treatment plans from the array of treatment plans; switching, in real time, between images of the teeth at the final stages for different treatment plans within the array of treatment plans based on one or more user-selected controls on the screen; and transmitting a selected one of the treatment plans for fabrication after the user has chosen the selected one of the treatment plans displayed on the screen.

The methods and apparatuses described herein may refer to transmitting and receiving to and/or from a remote site, from which the array of treatment plans specific to the patient's teeth may be generated, the remote site may be remote from the user, and may be accessible via a web (e.g., cloud) server, or the like. In some variations the treatment plans are generated locally, e.g., on software that is running on the user's computer/processor, which is the same processor containing instructions (e.g., code) for executing the interactive treatment planning, including receiving the array of treatment plans.

As mentioned, each treatment plan in the array may describe a set of sequential stages for orthodontic movement of the patient's teeth including a final stage. The treatment plan may include the final position of the patient's teeth, staging for the movements of the patient's teeth (e.g., a description of tooth movement directions along with a speed associated with each stage, which may be key frames, showing relative movement of the teeth over the treatment), and a set of aligner features placed on each tooth to improve predictability of the treatment and ensure teeth movements to happen. The treatment plan may also include metadata (e.g., annotations) about the number of stages, presence/absence of tooth modifications, effect on the patient's treatment goals, etc.). a As used herein, the phrase "real time" may refer to the immediate (or a perception of immediate or concurrent) response, for example, a response that is within milliseconds so that it is available virtually immediate when observed by the user. Near real time may refer to within a few seconds to a few minutes of concurrent.

The screen used to display and interact with the user may be any appropriate screen or monitor, including touchscreen and non-touchscreen screens. The screen may be part of a laptop, desktop, or other computer, including hand-held (e.g., smartphone, tablet, etc.) screens. The screen may include flat panel displays as well as other displays, including virtual reality (e.g., glasses, goggles, etc.) and projections (e.g., surface projections).

The different treatment properties that may be used to generate the various treatment plans may include one or more of: interproximal reduction (IRR)/changing spacing distance between teeth, extraction, and aligner attachments (one or more, at various locations), changing leveling strategy from "align by incisal edge" to "align by gingiva margins," etc.

As will be described in more detail below, any of the methods described herein may include generating the plurality of treatment plans, such as generating the array of full treatment plans including variations of different treatment properties. These treatment plans may be pre-calculated. Any number of treatment plans may be included in the array of treatment plans, typically 3 or more (e.g., 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 22 or more, 24 or more, 26 or more, 28 or more, 30 or more, 35 or more, 40 or more, 45 or more, 50 or more, 55 or more, 60 or more, 65 or more, 70 or more, 80 or more, 90 or more, 100 or more, 110 or more, 120 or more, etc.). In practice, any of these methods may include transmitting a model of the patient's teeth to the remote site holding the treatment plan generator, which may be referred to as a treatment plan optimizing engine or treatment plan optimizing generator. The treatment plan generator may be located, e.g., as part of a processor or other system, at a remote site. Thus, any of these methods may include generating, at the remote site, the array of treatment plans specific to the patient's teeth. The model of the patient's teeth (upper arch, lower arch, or upper and lower arch) may be transmitted to the remote site and may be received there as a digital file or it may be digitized at the remote site. The remote site may be a dental laboratory. In addition, the user may transmit a list of tooth movement prescription information (e.g. patient-specific treatment preferences), wherein the list of tooth movement prescription information comprises tooth movement limitations, retraction limitations, interproximal reduction limitations. In any of these variations, the remote site may also receive the users identity and may look up stored (e.g., in a database) user-specific preferences that may be applied in any case associated with that user (e.g., user-specific treatment preferences). The user may also (optionally) transmit treatment details or a reference to a set of treatment details, including product details specific to the one or more types of dental/orthodontic products to be used, if not included, may be set by default. For example, the user may transmit as input to the treatment plan generator, the name(s) or indicator(s) of particular dental/orthodontic treatment program(s), such as "OrthoGO." The treatment plan generator may then use this name or indicator to look up details specific to this treatment program from a memory accessible or included in the treatment plan generator such as the maximum number of aligners (e.g., the maximum duration of treatment), etc.

The user may be shown one or, more preferably, multiple treatment plans for their review (in real time or near real time). In displaying the treatment plans, the user may be shown the final stage of the treatment plan (showing the final position of the patient's teeth, as achieved by the treatment plan), and/or may be shown the metadata about the treatment plan (e.g., the number of stages, the treated/untreated components, etc.). Displaying images of the teeth at the final stage for each treatment plan of the subset of the treatment plans from the array of treatment plans may include concurrently displaying images of the teeth at the final stages for treatment plans have different numbers of sequential stages. The treatment plans may be shown side-by-side for comparison. In some variations, the user may toggle between "filters" or switches showing the different treatment plans (e.g., a plan with or without IPR, etc.). Because the treatment plans have been pre-calculated and are in the array, they may be shown in real time, and the user may easily switch between different versions, allowing the user to pick an optimal treatment for the patient.

As mentioned, switching between images of the teeth at the final stages for different treatment plans within the array of treatment plans may be based on one or more user-selected (selectable) controls on the screen, such as switching a treatment plan having a first number of sequential stages with a treatment plan having the same number of sequential stages but having different treatment properties when the user changes one or more user-selected controls on the screen.

For example, different filters/switches may toggle between treatment plans showing one or more tooth/treatment modifications. Virtually any modification may be used, including, for example: one or more of: extractions (of one or more teeth), adjusting of tooth overjet, adjusting for overbites, adjusting for cross bites, interproximal reductions (IPR), including one o or more aligner attachments on the teeth, and anterior to posterior (A-P) correction. These filters may correspond to treatment preferences.

The methods and apparatuses described herein may include one or more tools allowing the user to modify one or more of the treatment plans. Tools may be display tools (e.g., allowing rotation, sectioning, etc.) for modifying the display of the tooth shown by the treatment plan(s), or they may modify the treatment plan itself, e.g., modifying the position and/or orientation of the teeth in the final (or any intermediate) stage of the treatment plan. Tools may include adding/removing attachments on the teeth. The tools may include removing (e.g., reducing) material from the side of the tooth/teeth, and/or removing (e.g., extracting) the teeth.

Any of these methods may include transmitting the modified one or more treatment plans to the treatment plan optimizing generator (e.g., the remote site where the treatment plan optimizing generator is located) to recalculate the array of treatment plans based on the modifications of the one or more treatment plans.

Any of these methods may also allow the user to walk through the entire treatment plan, either as a key frame display and/or as a more intuitive display of a model (e.g., 3D model or projection) of the user's teeth in each stage. Thus, any of these methods may include displaying, on the screen, a plurality of the sequential stages (e.g., images of the teeth at each stage) when the user selects a stage selection control. These displays may be animations, showing movements of the teeth.

Any of the methods and apparatuses describe herein may allow the user to select a subset of treatment plans from the larger array (set) of treatment plans. This subset may be used for presentation to a patient, as described below (e.g., in a 'consulting mode') or for further modification or refinement, including for side-by side comparison. In some variations, the method or apparatus may automatically select the one or more treatment plans for display to the user, based on predefined user preferences. For example, any of these methods and apparatuses may include selecting the subset of the treatment plans from the array of treatment plans to display based on user preferences.

As described above, toggling the display between treatment plans may be performed by turning on/off one or more "filters" or toggles. For example, any of these methods and apparatuses may be configured to filter one or more of the displayed images of the teeth at the final stage of the subset of the treatment plans from the array of treatment plans when the user selects a filter control.

For example, a method of manufacturing a series of aligners for a patient's teeth may include: transmitting a model of the patient's teeth to a remote site; transmitting a list of tooth movement prescription information to the remote site; collecting (e.g., receiving, gathering, downloading, and/or accessing) from the remote site, an array of treatment plans specific to the patient's teeth, wherein each treatment plan in the array describes a set of sequential stages for orthodontic movement of the patient's teeth having a final stage, further wherein at least three of the treatment plans have different numbers of sequential stages, and further wherein, for each number of sequential stages, the array comprises two or more treatment plans having the same number of sequential stages but treatment properties; displaying on a screen, images of the teeth at the final stage for each treatment plan of a subset of the treatment plans from the array of treatment plans; switching, in real time, between images of the teeth at the final stages for different treatment plans within the array of treatment plans based on one or more user-selected controls on the screen; and transmitting a selected one of the treatment plans for fabrication after the user has chosen the selected one of the treatment plans displayed on the screen.

Any of the methods described herein may be performed by an apparatus configured to perform the method steps. In particular, described herein are apparatuses (e.g., systems) that are configured to execute instructions (code) to control an apparatus having a processor, display, input, etc. to interactively allow a user to design and manufacture a series of aligners for correction of malocclusions of a patient's teeth. Any of these apparatuses may be configured as non-transient, computer-readable media (e.g., software, firmware, hardware or some combination thereof) that includes instructions for controlling the apparatus as described herein and may be part of a system or sub-system.

For example, described herein are non-transient, computer-readable media containing program instructions for causing a computer to: receive, from a remote site, an array of treatment plans specific to the patient's teeth, wherein each treatment plan in the array describes a set of sequential stages for orthodontic movement of the patient's teeth including a final stage, further wherein at least three of the treatment plans have different numbers of sequential stages, and further wherein the array of treatment plans comprises two or more treatment plans having different treatment properties; display on a screen, images of the teeth at the final stage for each treatment plan of a subset of the treatment plans from the array of treatment plans; switch, in real time, between images of the teeth at the final stages for different treatment plans within the array of treatment plans based on one or more user-selected controls on the screen; and transmit a selected one of the treatment plans for fabrication after the user has chosen the selected one of the treatment plans displayed on the screen. Also described herein are systems including one or more processors configured to execute the program instructions. These systems may be referred to herein as treatment plan comparators (or interactive, real-time treatment plan comparators), and may optionally or additionally include one or more displays, one or more user selectable controls and one or more communications circuitry (e.g., a communications module, such as a wireless circuit, etc.).

The different treatment properties that may be varied between the different treatment plans may include treatment preferences, such as one or more of: allowing or restriction interproximal reduction (IRR), allowing or restriction extraction, and allowing or restricting aligner attachments (e.g., attachments on the teeth to couple to the aligner). The program instructions may be further configured to transmit a model of the patient's teeth to the remote site. The program instructions may be further configured to, generate at the remote site, the array of treatment plans specific to the patient's teeth.

The program instructions may be configured to transmit a list of tooth movement prescription information (e.g., to the remote site containing the treatment plan optimizing generator), wherein the list of tooth movement prescription information may include tooth movement limitations, retraction limitations, interproximal reduction limitations.

The program instructions may be configured to display images of the teeth at the final stage for each treatment plan of the subset of the treatment plans from the array of treatment plans by concurrently displaying images of the teeth at the final stages for treatment plans have different numbers of sequential stages.

The program instructions may be configured to switch between images of the teeth at the final stages for different treatment plans within the array of treatment plans based on one or more user-selected controls on the screen by switching a treatment plan having a first number of sequential stages with a treatment plan having the same number of sequential stages but having different treatment properties based on one or more user-selected controls on the screen. The different treatment properties may include one or more of: extractions, overjets, overbites, cross bites, interproximal reductions, attachments, and anterior to posterior (A-P) correction. The program instructions may be further configured to provide one or more tools allowing the user to modify one or more of the treatment plans.

The program instructions may be further configured to transmit the modified one or more treatment plans to the remote site to recalculate the array of treatment plans based on the modifications of the one or more treatment plans. The program instructions may be further configured to display, on the screen, a plurality of the sequential stages when the user selects a stage selection control. The stage selection control may allow the user to dynamically, in real time, view the different stages (e.g., positions of the teeth in each stage).

The program instructions may be further configured to select the subset of the treatment plans from the array of treatment plans to display based on user preferences. The program instructions may be further configured to filter one or more of the displayed images of the teeth at the final stage of the subset of the treatment plans from the array of treatment plans when the user selects a filter control.

As mentioned, any of these methods and apparatuses may include a consultation mode that presents multiple treatment plans to the patient or physician, including treatment plans having different numbers of stages and different final tooth positions. These displayed treatment plans may be selected by the user (e.g., dental professional) as a subset of the treatment plans in the array. The displayed treatment plans (and any corresponding metadata about them) may be displayed sequentially or simultaneously (e.g., side-by-side) for viewing by the patient. Pricing information may also be shown corresponding to each treatment plan, along with a graphical display that allows the patient (and/or user) to see the final tooth positions and allows the user to select the desired outcome. Multiple treatment plans having a different number of stages and different final tooth positions may be presented to the patient, and the patient (by themselves or in consultation with the dental professional) may decide which treatment plan to select.

Once a treatment plan is selected, it may be used to generate a series of aligners. For example, the treatment plan may be transmitted to a manufacturing facility that may directly print (e.g., by 3D printing) each aligner in the series, or the treatment plan may be used to generate a positive model of the patient's teeth at each stage used for forming the aligners (e.g., by thermoforming).

Thus, in consultation mode the patient is presented with multiple treatment plans having different numbers of stages and allowed to select which treatment plan to manufacture and use.

For example, a method of manufacturing a series of aligners for a patient's teeth may include a consultation mode. For example, the method may include: collecting (e.g., receiving, forming, gathering, downloading, and/or accessing), in a processor, an array of treatment plans specific to the patient's teeth, wherein each treatment plan in the array describes a set of sequential stages for orthodontic movement of the patient's teeth, including a final stage, further wherein at least three of the treatment plans have different numbers of sequential stages, and further wherein the final stages of the treatment plans within the array of treatment plans are different; displaying, on a screen, images of the teeth at the final stages for a subset of the treatment plans from the array of treatment plans; selecting, by a user, two or more treatment plans from the subset of the treatment plans using one or more controls on the screen; and displaying, to the patient, the two or more treatment plans from the subset of the treatment plans; and transmitting a selected one of the two or more treatment plans for fabrication after the patient has chosen the selected one of the treatment plans.

As mentioned, any of these method may include transmitting a model of the patient's teeth to a remote site (e.g., the location of the treatment plan optimizing generator). Displaying the two or more treatment plans may include displaying annotations describing changes in the final stage of each of the two or more treatment plans compared to the model of the patient's teeth. The annotations (which may be "metadata" about the treatment plan) may comprise one or more of: changes in the malocclusion, changes in the patient's bite, and changes in the upper and/or lower crowding.

Displaying, to the patient, the two or more treatment plans from the subset of the treatment plans may comprise displaying the number of sequential stages.

Any of these methods may include switching, in real time, one or more of the images of the teeth at the final stages of the subset for different treatment plans with an image of the final stage of one or more other treatment plans from the array of treatment plans, based on one or more user-selected controls on the screen. The two or more treatment plans from the subset of the treatment plans may comprise two or more treatment plans having different numbers of sequential stages.

For example, a method of manufacturing a series of aligners for a patient's teeth may include: transmitting a model of the patient's teeth to a remote site; collecting (e.g., receiving, forming, gathering, downloading, and/or accessing), from the remote site, an array of treatment plans specific to the patient's teeth, wherein each treatment plan in the array describes a set of sequential stages for orthodontic movement of the patient's teeth, including a final stage, further wherein at least three of the treatment plans have different numbers of sequential stages, and further wherein the final stages of the treatment plans within the array of treatment plans are different; displaying, on a screen, images of the teeth at the final stages for a first subset of the treatment plans from the array of treatment plans; selecting, by a user, two or more treatment plans from the first subset of the treatment plans using one or more controls on the screen; displaying, to the patient, the two or more treatment plans and annotations describing changes in the final stage of each of the two or more treatment plans compared to the model of the patient's teeth; and transmitting a selected one of the two or more treatment plans for fabrication after the patient has chosen the selected one of the treatment plans.

Also described herein are non-transient, computer-readable medium containing program instructions for causing a computer to: receive, in a processor, an array of treatment plans specific to the patient's teeth, wherein each treatment plan in the array describes a set of sequential stages for orthodontic movement of the patient's teeth, including a final stage, further wherein at least three of the treatment plans have different numbers of sequential stages, and further wherein the final stages of the treatment plans within the array of treatment plans are different; display, on a screen, images of the teeth at the final stages for a first subset of the treatment plans from the array of treatment plans; select, by a user, two or more treatment plans from the first subject of the treatment plans using one or more controls on the screen; and display, to the patient, the two or more treatment plans; and transmit a selected one of the two or more treatment plans for fabrication after the patient has chosen the selected one of the treatment plans.

In general, the methods and apparatuses described herein provide interactive treatment planning, and may present multiple, full and pre-calculated treatment plans to a user (e.g., dental professional) and allows the user to switch between views of different pre-calculated treatment plans, and to modify the one or more treatment plans. The systems and methods described herein may also allow for the doctor to change final position and re-calculate a new final position real time without sending it to the technician Also described herein are methods and apparatuses (e.g., non-transient, computer-readable medium containing program instructions for causing a computer to perform steps) for creating one or more (e.g., an array of) treatment plans to align, including partially aligning, a patient's teeth.

For example, described herein are automated methods of creating a treatment plan to align a patient's teeth using a plurality of removable aligners to be worn in sequential stages, the method comprising: collecting (e.g., receiving, forming, gathering, downloading, and/or accessing), in a processor: a digital model of a patient's teeth, a set of treatment preferences and/or a reference to a set of treatment preferences, a comprehensive final position of the patient's teeth, and (optionally) a set of treatment details or an identifier identifying the set of treatment details; selecting a plurality of numerically expressed treatment targets and constraints from a memory accessible to the processor, based on the set of treatment details, the set of treatment preferences and the comprehensive final position of the patient's teeth; combining the plurality of numerically expressed treatment targets to form a single numerical merit function; selecting a plurality of numeric limits on the treatment constraint functions based on the set of treatment details, the set of treatment preferences and the comprehensive final position of the patient's teeth; minimizing the single numerical merit function to get a solution vector including all stages forming the treatment plan, subject to the plurality of limits on numeric treatment constraints; and mapping the solution vector to a treatment plan, wherein the treatment plan includes a final tooth position that is different from the comprehensive final position of the patient's teeth.

In general, treatment details may refer to a product definition, which may be the parameters set by the properties of the aligner product to be used for the treatment, e.g., the number of stages, the rate of tooth movement, etc. Treatment preferences may refer to the treatment preferences of the dental practitioner (e.g., which teeth not to move, etc.) and may be specific to the patient, or may be specific to the user and applied to all of the user's patient's. Thus, treatment details may include details about the product(s) that may be used to achieve the treatment, including the number and type of aligners, and any properties of the aligners themselves. In some variations, the treatment details are not provided separately to the method or apparatus, but are available (e.g., as a default) when generating the one or more treatment plans. The method or apparatus may default to a single set of treatment details, corresponding to a single dental/orthodontic product, or it may be selected from a listing of predefined products having specified properties. Alternatively, the user may provide the details specific to a particular product or products, forming the treatment details. Note that when a plurality of different treatment plans are to be generated, forming an array of treatment plans, the various sets of treatment details, corresponding to different dental/orthodontic products, may be used to generate different variations.

Examples of treatment preferences are described in detail herein. For example, treatment preferences may include one or more of: an indicator of which teeth are not permitted to move, an indication of which teeth should not have an attachment, an indicator of which teeth to treat, an indicator of tooth class correction amount, an indicator that interproximal reduction is to be used, an indicator that arch expansion is to be used, and indicator of spacing between teeth, an indicator or tooth levelling. The identifier identifying the treatment details may identify a product having a defined set of treatment details accessible to the processor.

Examples of treatment details (corresponding to the properties of different products that may be used) are also provided below, but may include one or more of: a maximum allowed number of stages, whether attachments to the patient's teeth are allowed, a maximum allowed tooth root movement, a maximum allowed tooth crown movement, and a maximum allowed tooth rotation.

Combining the numerically expressed treatment targets may mean weighting each of the numerically expressed treatment targets in the single numerical function. A weight factor may be used to multiple any of the numerically expressed treatment targets; different weight factors may be used for each or a subset of the numerically expressed treatment targets. Weighting factors may be set empirically or may be adjusted by the apparatus.

The single numerical function may include, for a set of teeth, a sum of at least: a difference from the positions of the teeth compared to the comprehensive final position of the patient's teeth, a measure of misalignment in an x direction for the teeth, a measure of misalignment in a z direction for the teeth, a measure of misalignment of a dental arch of the teeth, a measure of diastema between neighboring teeth, a measure of overjet of the teeth, a measure of overbite of the teeth, a measure of collisions between the teeth, a measure of the difference between an arch of the teeth and the comprehensive final position of the patient's teeth, a measure of the difference in leveling between the teeth and the comprehensive final position of the patient's teeth, a measure of the amount of occlusion between the teeth of the patient's upper and lower jaws, a measure of the difference in the amount of occlusion between the teeth and the comprehensive final position of the patient's teeth, a measure of the amount of mesial to distal round trips of the teeth, a measure of the amount of buccal to lingual round trips of the teeth, and a measure of a number of aligner stages compared to a target number of aligner stages from the set of treatment details. For example, the single numerical function may include, for a set of teeth, a sum of at least: a difference from the positions of the teeth compared to the comprehensive final position of the patient's teeth, a measure of misalignment for the teeth, and a measure of a number of aligner stages compared to a target number of aligner stages from the set of treatment details.

The methods described herein may also include adjusting the plurality of numerically expressed treatment targets into a plurality of adjusted numerically expressed treatment targets based on: the set of treatment details, the set of treatment preferences and the comprehensive final position of the patient's teeth, further wherein combining the plurality of numerically expressed treatment targets comprises combining the plurality of adjusted numerically expressed treatment targets.

The plurality of numeric limits may comprise one or more of: a maximum velocity of tooth movement, a maximum amount of collision between teeth, a tooth movement limitation, a maximum number of aligner stages, a maximum amount of occlusion, a maximum amount of occlusion, a maximum amount of overbite, a maximum amount of overjet, and a maximum midline position.

In general, minimizing the single numerical function subject to the plurality of numeric limits may comprise using a constrained optimization method to get a solution vector. The constrained optimization method may comprise an interior point method (e.g., interior point method variations such as SQP and Active Set).

Mapping the solution vector to a treatment plan may comprises converting the solution vector into a set of key frames for each tooth, corresponding to a stage number, and positional information for each tooth, including an x coordinate, a y coordinate, a z coordinate, and an angulation, an inclination and a rotation angle. In mapping the solution vector to form a key function, the solution vector may include numerous key function components that may be combined to form the complete key function set for the treatment plan. Thus, mapping the solution vector to a treatment plan may include, for some teeth, mapping a single variable in the solution vector to a single coordinate or angle in a key frame, while for some teeth, mapping may include mapping a linear combination of multiple variables from the solution vector to a single coordinate or angle in a key frame.

The method may also include displaying the final tooth position of the treatment plan and/or transmitting the treatment plan to be displayed.

For example, an automated method of creating a treatment plan to align a patient's teeth using a plurality of removable aligners to be worn in sequential stages, may include: collecting (e.g., receiving, forming, gathering, downloading, and/or accessing), in a processor: a digital model of a patient's teeth; accessing (by the processor) a set of treatment preferences, a comprehensive final position of the patient's teeth, and a set of treatment details; selecting a plurality of numerically expressed treatment targets from a memory accessible to the processor based on: the set of treatment details, the set of treatment preferences and the comprehensive final position of the patient's teeth; adjusting the plurality of numerically expressed treatment targets into a plurality of adjusted numerically expressed treatment targets based on: the set of treatment details, the set of treatment preferences and the comprehensive final position of the patient's teeth; combining the plurality of adjusted numerically expressed treatment targets to form a single numerical function; setting a plurality of numeric limits on the single numerical function based on the set treatment preferences; minimizing (e.g., iteratively) the single numerical function subject to the plurality of numeric limits to get a solution vector including all stages forming the treatment plan; and mapping the solution vector to a treatment plan, wherein the treatment plan includes a final tooth position that is different from the comprehensive final position of the patient's teeth.

Accessing the set of treatment preferences may include collecting (e.g., receiving, forming, gathering, downloading, and/or accessing in the processor) the set of treatment preferences, or collecting a reference to a set of treatment preferences that the processor may use to look up a set of (e.g. one or more) treatment preferences from a memory accessible by the processor holding, for example, a look-up table of preferences indexed by a reference. Accessing the comprehensive final position of the patient's teeth may include receiving the comprehensive final position (e.g., as a digital model or representation of positions of the patient's teeth), or it may include generating, using the processor, the comprehensive final position. The comprehensive final position may be manually or semi-manually generated and a digital copy sent to the processor. If the processor has already generated the comprehensive final position, the processor may store it in a memory and access it later (e.g., during additional cycles). Accessing the set of treatment details may include accessing a stored (in a memory) set of treatment details, including accessing a 'default' set of treatment details, receiving the set of treatment details, or it may include receiving an identifier identifying the set of treatment details and using the identifier to look up, from a memory (e.g. holding a look-up table) a set of treatment details. The identifier may be a product name/model, etc.

Also described herein are apparatuses for performing any of these methods as a non-transient, computer-readable medium containing program instructions for creating a treatment plan to align a patient's teeth using a plurality of removable aligners. For example, the program instructions may cause a processor to: receive, in the processor: a digital model of a patient's teeth, a set of treatment preferences or a reference to a set of treatment preferences, a comprehensive final position of the patient's teeth, and a set of treatment details or an identifier identifying the set of treatment details; select a plurality of numerically expressed treatment targets from a memory accessible to the processor, based on the set of treatment details, the set of treatment preferences and the comprehensive final position of the patient's teeth; combine the plurality of numerically expressed treatment targets to form a single numerical function; select a plurality of numeric limits on the single numerical function based on the set treatment preferences; minimize the single numerical function subject to the plurality of numeric limits to get a solution vector including all stages forming the treatment plan; and map the solution vector to a treatment plan, wherein the treatment plan includes a final tooth position that is different from the comprehensive final position of the patient's teeth.

As mentioned above, the treatment preferences may comprise one or more of: an indicator of which teeth are not permitted to move, an indication of which teeth should not have an attachment, an indicator of which teeth to treat, an indicator of tooth class correction amount, an indicator that interproximal reduction is to be used, an indicator that arch expansion is to be used, and indicator of spacing between teeth, an indicator or tooth levelling. The identifier identifying the treatment details may identify a product having a defined set of treatment details accessible to the processor.

The set of treatment details may comprises one or more of: a maximum allowed number of stages, whether attachments to the patient's teeth are allowed, a maximum allowed tooth root movement, a maximum allowed tooth crown movement, and a maximum allowed tooth rotation. Combining the numerically expressed treatment targets may further comprise weighting each of the numerically expressed treatment targets in the single numerical function.

The single numerical function may include, for a set of teeth, a sum of at least: a difference from the positions of the teeth compared to the comprehensive final position of the patient's teeth, a measure of misalignment in an x direction for the teeth, a measure of misalignment in a z direction for the teeth, a measure of misalignment of a dental arch of the teeth, a measure of diastema between neighboring teeth, a measure of overjet of the teeth, a measure of overbite of the teeth, a measure of collisions between the teeth, a measure of the difference between an arch of the teeth and the comprehensive final position of the patient's teeth, a measure of the difference in leveling between the teeth and the comprehensive final position of the patient's teeth, a measure of the amount of occlusion between the teeth of the patient's upper and lower jaws, a measure of the difference in the amount of occlusion between the teeth and the comprehensive final position of the patient's teeth, a measure of the amount of mesial to distal round trips of the teeth, a measure of the amount of buccal to lingual round trips of the teeth, and a measure of a number of aligner stages compared to a target number of aligner stages from the set of treatment details.

The non-transient, computer-readable medium of claim 15, wherein the single numerical function includes, for a set of teeth, a sum of at least: a difference from the positions of the teeth compared to the comprehensive final position of the patient's teeth, a measure of misalignment for the teeth, and a measure of a number of aligner stages compared to a target number of aligner stages from the set of treatment details.

The program instructions may be further configured to adjust the plurality of numerically expressed treatment targets into a plurality of adjusted numerically expressed treatment targets based on: the set of treatment details, the set of treatment preferences and the comprehensive final position of the patient's teeth. Further, the program instructions may also be configured to combine the plurality of numerically expressed treatment targets by combining the plurality of adjusted numerically expressed treatment targets.

The plurality of numeric limits may comprise one or more of: a maximum velocity of tooth movement, a maximum amount of collision between teeth, a tooth movement limitation, a maximum number of aligner stages, a maximum amount of occlusion, a maximum amount of occlusion, a maximum amount of overbite, a maximum amount of overjet, and a maximum midline position. The program instructions may be further configured to minimize the single numerical function subject to the plurality of numeric limits using a constrained optimization method to get a solution vector.

The program instructions may be further configured to map the solution vector to a treatment plan by converting the solution vector into a set of key frames for each tooth, corresponding to a stage number, and positional information for each tooth, including an x coordinate, a y coordinate, a z coordinate, and an angulation, an inclination and a rotation angle.

The program instructions may be configured to provide the final tooth position of the treatment plan for display.

Any of the methods and apparatuses described herein may be configured to generate an array of treatment plan variations. This may be achieved, for example, by modifying, either automatically or manually, the treatment preferences and/or treatment details. For example, the maximum number of stages (corresponding to the number of aligners to be used in a treatment) may be modified to generate treatment plan variations having different treatment durations, since the duration of treatment is typically correlated to the number of aligners to be worn. Although in general, the more stages/aligners used, the greater the overall amount of correction that may be achieved, as described herein (e.g., approaching a comprehensive final position of the teeth which may be considered an optimal treatment plan) in some cases it may be preferable by the patient and/or dental professional to limit the duration of treatment and settle for an improved, but not perfectly corrected, alignment.

Also described herein are methods of modifying a treatment plan for a series of aligners and/or manufacturing a series of aligners for a patient's teeth. For example a method may include: transmitting a model of the patient's teeth to a remote site; transmitting a list of tooth movement prescription information to the remote site; collecting a plurality of treatment plans specific to the patient's teeth using an ideal final position for the patient's teeth and the model of the patient's teeth, wherein each treatment plan in the plurality of treatment plans describes a set of sequential stages for orthodontic movement of the patient's teeth having a final stage, further wherein, for each treatment plan the final stage is different from the ideal final position for each of the different treatment properties of the patient's teeth; ranking the plurality of treatment plans based on how comprehensive they are compared to the ideal final position; and displaying on a screen, images of the patient's teeth at the final stage for either the first or the first and second treatment plans from the array of treatment plans; switching, in real time, between images of the teeth at the final stages for different treatment plans within the array of treatment plans based on one or more user-selected controls on the screen; and transmitting a selected one of the treatment plans for fabrication after the user has chosen the selected one of the treatment plans displayed on the screen.

The different treatment properties may comprise one or more of: interproximal reduction (IRR), extraction, and aligner attachments. For example, the tooth movement prescription information may comprise tooth movement limitations, retraction limitations, interproximal reduction limitations.

Any of these methods may include switching between images of the teeth at the final stages for different treatment plans within the array of treatment plans based on one or more user-selected controls on the screen by switching a treatment plan having a first number of sequential stages with a treatment plan having the same number of sequential stages but having different treatment properties based on one or more user-selected controls on the screen.

Ranking based on how comprehensive the treatment plan is may include looking up a score from a database of rankings indexed by two or more of: interproximal reductions, attachments, dental aligner product, extractions, overjets, overbites, cross bites, and anterior to posterior (A-P) correction. Alternatively or additionally, ranking based on how comprehensive the treatment plan is may include scoring the treatment plan based on three or more of: interproximal reductions, attachments, dental aligner product, extractions, overjets, overbites, cross bites, and anterior to posterior (A-P) correction.

The method may also include modifying one or more of the treatment plans using the user interface and transmitting the modified one or more treatment plans to the remote site to recalculate the array of treatment plans based on the modifications of the one or more treatment plans.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7D schematically illustrates one example of a method for interactive real-time treatment plan comparison, which may be part of a method of manufacturing a series of aligners for a patient's teeth.

FIG. 8A is a user interface for a user (e.g., clinician, orthodontist, dentist, etc.) that may be executed as a non-transient, computer-readable medium containing program instructions for causing a computer to execute control to interactively display, select and/or modify treatment plans.

FIG. 8B is another example of a user interface, configured as an interactive prescription interface.

FIG. 9A is an example of a user interface showing the concurrent, real-time, display of multiple treatment plans showing treatments fixed at 26, 14 and 7 stages, respectively. In FIG. 9A, the final tooth configuration achieved by each treatment plan is shown for comparison, and toggles (filter controls) are included for showing alterative treatment plans calculated with/without IPR and with/without attachments. Additional filters may be included.

FIG. 9B shows the user interface of FIG. 9A after selecting (turning on) two filters, so that the treatment plan on the right (fixed at 26 stages) is a treatment plan including both IPR and attachments, and results in resolution of the patient's crowding treatment target and partially resolves the patient's open bite.

FIGS. 9C, 9D and 9E are examples of user interfaces that interactively displays and allows the user to modify (and resubmit) one or more treatment plans. FIG. 9C is an example of a user interface showing an interactive treatment planning screen in which a model (3D digital model) of the patient's dentition is included in a large display window. FIG. 9D is an example of a user interface that includes a window for showing one or both of the patient's dental arches at any stage of a proposed treatment plan. FIG. 9E is another example of a user interface, similar to that shown in FIG. 9D.

FIG. 11A is another example of a user interface such as the one shown in FIG. 10A, in which the user may comment (e.g., via text) for additional modifications.

In FIG. 12, the patient (Joe Smith) is being shown two options, a treatment plan having 26 stages with IPR and aligner attachments, and a second treatment plan having 14 stages without either IPR or aligners. The user interface (display) also indicates that the 26 stage treatment plan resolves the therapeutic goal of reducing crowding and open bite; the 14 stage treatment plan resolves the crowding (but not the open bite). The user interface also indicates the treatment goals upper and lower crowding and open bite) as the malocclusion analysis.

FIG. 13 is another example of a user interface configured for consultation with the patient. In FIG. 13, the user interface shows the patient's current dentition ("now") and identifies two malocclusion issues, and shows a 26 stage treatment plan (center) and a 14 stage treatment plan (right). The 26 stage treatment plan resolves the upper and low crowding and the open bite. The 14 stage treatment plan resolves the upper and lower crowding and partially resolves the open bite.

FIG. 14 is an example of a user interface showing a 3D model of the patient's teeth as they are moved during an exemplary 26 stage treatment plan. The display includes a control allowing the user to animate the display (moving from the initial, untreated condition, to the final position, or manually selecting any of the treatment stages.

FIG. 16A is a frontal view of a digital model (e.g., scan) of a patient's dental arch, in an untreated configuration.

FIGS. 16B-16M graphically illustrates an array of treatment plans, showing the final stage positions of the patient's teeth for each of 12 treatment plans. FIGS. 16B, 16C and 16D show the final stage tooth positions of a treatment plans generated assuming that no aligner attachments would be used, and no IPR is used on the patient's teeth; in FIG. 16B the treatment was limited to 26 stages, in FIG. 16C the treatment plan is limited to 14 stages and in FIG. 16D the treatment plan is limited to 7 stages. FIGS. 16E, 16F and 16G show the final stage tooth positions of a treatment plans generated assuming that aligner attachments would be used, and no IPR will be performed on the patient's teeth; in FIG.

16E the treatment was limited to 26 stages, in FIG. 16F the treatment plan is limited to 14 stages and in FIG. 16G the treatment plan is limited to 7 stages. FIGS. 16H, 16I and 16J show the final stage tooth positions of a treatment plans generated assuming that no aligner attachments would be used, but that IPR will be performed on the patient's teeth; in FIG. 16H the treatment was limited to 26 stages, in FIG. 16I the treatment plan is limited to 14 stages and in FIG. 16J the treatment plan is limited to 7 stages.

FIGS. 16K, 16L and 16M show the final stage tooth positions of a treatment plans generated assuming that aligner attachments would be used, and IPR will be performed on the patient's teeth; in FIG. 16K the treatment was limited to 26 stages, in FIG. 16L the treatment plan is limited to 14 stages and in FIG. 16M the treatment plan is limited to 7 stages.

FIG. 17 is another example of a user interface illustrating the real-time display of multiple treatment plans having limited numbers of stages. In FIG. 17 the left panel shows the final position of the teeth following a treatment plan that was generated by limiting the number of stages to 26 stages. The user controls on the right of the user interface ("filters") may be used to select one or more different treatment plans including a different number of stages ("product"), different treatment properties (e.g., IPR, attachments). The user interface may also show preferences ("apply template") and may show any of these variations in real time, by immediately switching between the different treatment plans. The control on the bottom of the left panel allows the user to select and display the teeth position of any of the stages. As in any of the user interfaces, the currently displayed treatment plan may be selected for comparison as part of a consultation screen. Additional controls may allow modification of the treatment plan(s) or immediate manufacturing/ordering of a series of aligners corresponding to the selected treatment plan.

FIGS. 30A-30C illustrate cross-sections through examples of 3D shapes having a core that is a constant radius from the core. In FIG. 30A the 3D shape is a sphere, showing a point as the core. In FIG. 30B, the 3D shape is a capsule, having a line and an outer surface that is constant radius from the line. FIG. 30C shows an example of a rectangular core having a constant radius from the square.

FIGS. 31A-31C show exemplary 3D shapes corresponding to those shown in FIGS. 30A-30C, respectively. In FIG. 31A the 3D shape is a sphere. In FIG. 31B, the 3D shape is a capsule. In FIG. 31C the 3D shape is a rounded rectangle.

FIGS. 32A and 32B illustrate top and side perspective views, respectively, of digital models of molars having outer surfaces that have been modeled by packing the surfaces with capsules.

FIGS. 33A-33B illustrate left and right side perspective views, respectively, of digital models of a portion of dental device (shown as precision wings) having outer surfaces that have been modeled by packing the surfaces with capsules.

FIG. 36 is an example of pseudo-code for traversal of a bounding box hierarchy to skip distance calculation between capsules that cannot influence the final value of collisions between two surfaces.

FIG. 43A is a table (Table 1) showing rankings of treatment plans indexed by attachments (all, posterior only, none) and interproximal reduction (IPR used, IPR not used) for single arch treatment plans. The value represents the relative rank of comprehensiveness (1 is highest).

FIG. 43B is a table (Table 2) showing rankings of treatment plans indexed by attachments (all, posterior only, none) and interproximal reduction (IPR used, IPR not used) for dual arch treatment plans. The value represents the relative rank of comprehensiveness (1 is highest).

In FIG. 44, a control configured as a drop-down menu or filter allows the user to switch between the type of attachments (e.g., all attachments, no attachments or poster-only attachments.

DETAILED DESCRIPTION

Figure 1B:
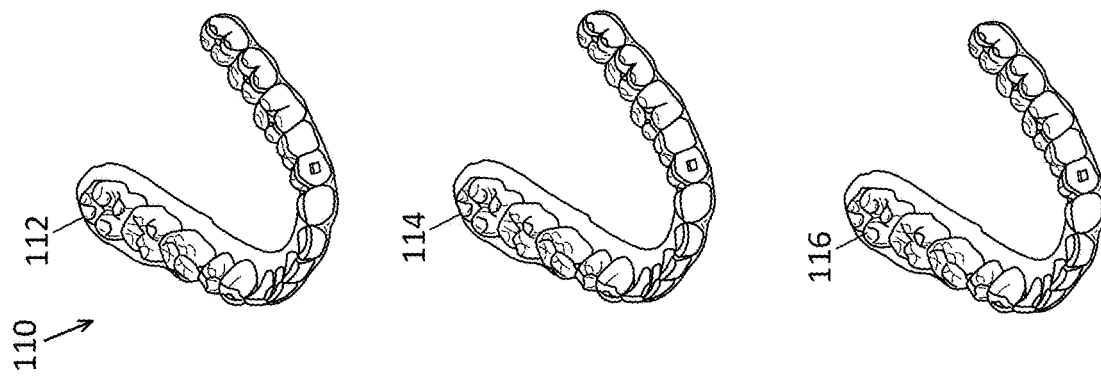
FIG. 1B illustrates a series of tooth repositioning appliances (aligners) configured to be worn sequentially (over the course of multiple days or weeks) for repositioning a patient's teeth.

In general, described herein are methods and apparatuses for manufacturing a series of aligners for a patient's teeth that may include generating multiple treatment plans that are limited various specified stages (e.g., 5 stages, 6 stages, 7 stages, 8 stages, 9 stages, 10 stages, 10 stages, 12 stages, 14 stages, 15 stages, 16 stages, 17 stages, 18 stages, 19 stages, 20 stages, 21 stages, 22 stages, 23 stages, 24 stages, 25 stages, 26 stages, 27 stages, 28 stages, 29 stages, 30 stages, etc.) and variations of these fixed-stage treatment plans in which one or more features are included to a predetermined degree (e.g., interproximal reduction, use of some number of aligner attachments, etc.). These methods and apparatuses may also include interactively displaying the multiple treatment plans, and allowing a user, such as a dental professional (e.g., doctor, dentist, orthodontist, etc.) to view, select and/or modify the multiple treatment plans. The multiple treatment plans may be labeled to indicate what treatment goals they do or do not address. The user may also select a subset of the multiple treatment plans for inclusion as part of a patient consultation, displaying the treatment plans for comparison and selection by patient.

A treatment plan optimizing generator, described in greater detail below, may be used to generate a plurality of treatment plans that are variations of each other. Typically the input to the treatment plan optimizing generator is a digital scan of the patient's teeth, as well as the constraints (e.g., number of stages, tooth modifications features, etc.) and preferences, and an "ideal" alignment of the patient's teeth (which may be manually, automatically or semi-automatically generated). The treatment plan optimizing generator may then automatically generate a treatment plan that is limited by those constraints, and that both addresses one or more treatment goals (which may also be identified or automatically identified) and is as close to the ideal alignment as possible. The treatment plan optimizing generator may be used multiple times to automatically generate a plurality of treatment plan variations that may be collected into an array (or group) of treatment plans.

As will be described in greater detail here, the results of the multiple treatment plan generation may be presented to a user. The multiple treatment plans may be collected as an array of multiple treatment plans that may include metadata identifying each treatment plan and/or the treatment goal that it addresses or does not address. Each treatment plan may represent a clinically feasible treatment plan. Further, for each plan there may be several options available to modify the plan. Plans may be limited to the number of stages, which may correlate to a commercial product. The product may include restrictions (product limitations) which may be included in the treatment plan. For example treatment plans may correspond to low stage plans (e.g. between 5 and 13 stages), intermediate stage plans (between 14 and 25 stages) and high intermediate stage plans (26 and more stages). Other tooth modification features may also be included as limitations modifying the treatment plans, such as including or not including aligner attachment placement. If attachments are not allowed, then a restricted clinical protocol may be applied to avoid unpredictable movements. Another example of a tooth modification feature that may be included in the treatment plan is to include IPR or not include IPR. If IPR is not allowed then the best plan may be presented with a condition that IPR is not allowed during the duration of the treatment.

In addition, template selection may select a clinical protocol to be applied for plan generation. The user may select any combination of options in order to determine which treatment plan is the best, given the constraints provided. All possible combinations of the plans are pre-calculated so the user can see, in real time, the options available by changing to a different clinical filter without the need to redo the treatment plan. The user may also modify any of the treatment plans with 3D controls, in which each change made with tools modifies a plan but is configured to keeps the ability to transfer the selected (and modified) treatment plan directly to manufacturing (e.g., without further human intervention).

In general, the methods described here are directed to the manufacture of a series or sequence of orthodontic aligner appliances that maybe worn sequentially to correct malocclusion(s). For example, FIG. 1 illustrates an exemplary tooth repositioning appliance or aligner 100 that can be worn by a patient in order to achieve an incremental repositioning of individual teeth 121 in the jaw. The appliance can include a shell 110 (e.g., a continuous polymeric shell or a segmented shell) having teeth-receiving cavities 111 that receive and resiliently reposition the teeth 121. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using additive manufacturing techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance may be repositioned by the appliance while other teeth can provide a base or anchor region for holding the appliance in place as it applies force against the tooth or teeth targeted for repositioning. In some cases, some or most, and even all, of the teeth may be repositioned at some point during treatment. Teeth that are moved can also serve as a base or anchor for holding the appliance as it is worn by the patient. No wires or other means may be necessary for holding an appliance in place over the teeth. In some cases, however, it may be desirable or necessary to provide individual attachments or other aligner features for controlling force delivery and distribution Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. Additional examples of accessories include but are not limited to opposing arch features, occlusal features, torsional rigidity features, occlusal cusp, and bridges. In some embodiments, the appliances, systems and methods described herein include improved orthodontic appliances with integrally formed features that are shaped to couple to such auxiliary components, or that replace such auxiliary components.

Figure 1A:
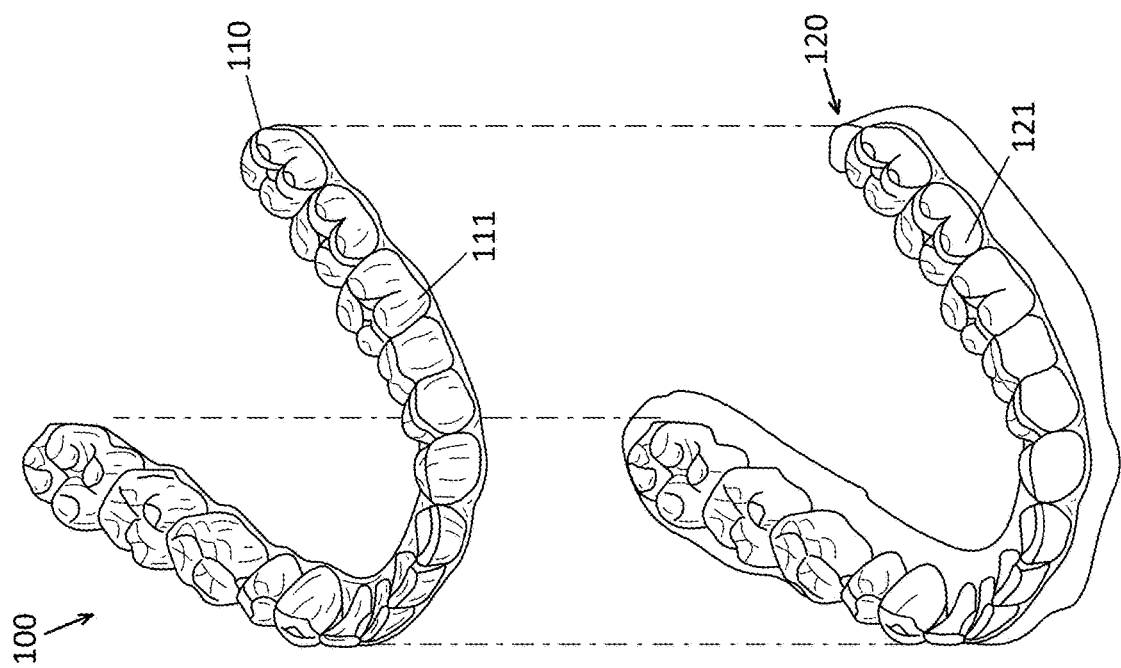
FIG. 1A is a tooth repositioning appliance, shown in this example as an aligner or shell aligner.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement towards a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

FIG. 1C illustrates a method 150 of orthodontic treatment using a plurality of appliances, in accordance with embodiments. The method 150 can be practiced using any of the appliances or appliance sets described herein. In step 160, a first orthodontic appliance is applied to a patient's teeth in order to reposition the teeth from a first tooth arrangement to a second tooth arrangement. In step 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement towards a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object's geometry can be used, referred to herein as "continuous direct fabrication." Various types of continuous direct fabrication methods can be used. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step using the same fabrication machine and method. For instance, a multi-tip extrusion apparatus can be used to selectively dispense multiple types of materials (e.g., resins, liquids, solids, or combinations thereof) from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

Although various embodiments herein are described with respect to direct fabrication techniques, it shall be appreciated that other techniques can also be used, such as indirect fabrication techniques. In some embodiments, the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more structures in the shell (e.g., by cutting, etching, etc.), and/or coupling one or more components to the shell (e.g., by extrusion, additive manufacturing, spraying, thermoforming, adhesives, bonding, fasteners, etc.). Optionally, one or more auxiliary appliance components as described herein (e.g., elastics, wires, springs, bars, arch expanders, palatal expanders, twin blocks, occlusal blocks, bite ramps, mandibular advancement splints, bite plates, pontics, hooks, brackets, headgear tubes, bumper tubes, palatal bars, frameworks, pin-and-tube apparatuses, buccal shields, buccinator bows, wire shields, lingual flanges and pads, lip pads or bumpers, protrusions, divots, etc.) are formed separately from and coupled to the appliance shell (e.g., via adhesives, bonding, fasteners, mounting features, etc.) after the shell has been fabricated.

The orthodontic appliances herein can be fabricated using a combination of direct and indirect fabrication techniques, such that different portions of an appliance can be fabricated using different fabrication techniques and assembled in order to form the final appliance. For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). The computer-based methods presented herein can improve the accuracy, flexibility, and convenience of appliance fabrication.

The methods and apparatuses described herein may form, or be incorporated into a computer-based 3-dimensional planning/design tool, and may be used to design and fabricate the orthodontic appliances described herein.

Figure 2A:
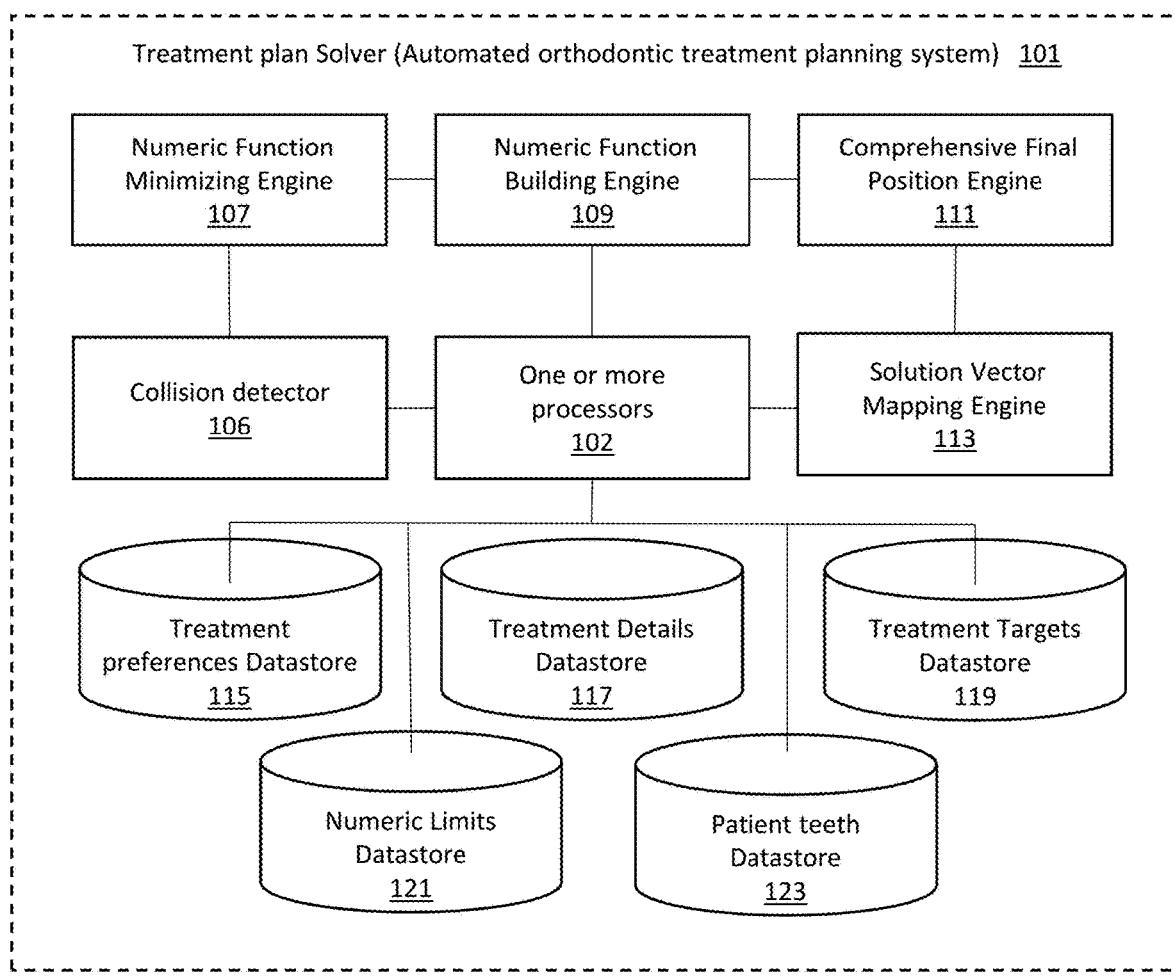
FIG. 2A is a schematic example of a treatment plan solver (e.g., an automated orthodontic treatment planning system).

FIG. 2A shows one example of a treatment plan solver (e.g., an automated orthodontic treatment planning system, or solver) 101 that may be used to automatically generate a series of treatment plans and therefore manufacture a series of aligners based on one of the series of treatment plans.

The solver 101 may include a variety of modules, including engines, processors on which the engines may operate, and/or one or more datastores. A computer system can be implemented as an engine, as part of an engine or through multiple engines. As used herein, an engine may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Alternatively or additionally, different engines may share the same processor. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

Figure 2B:
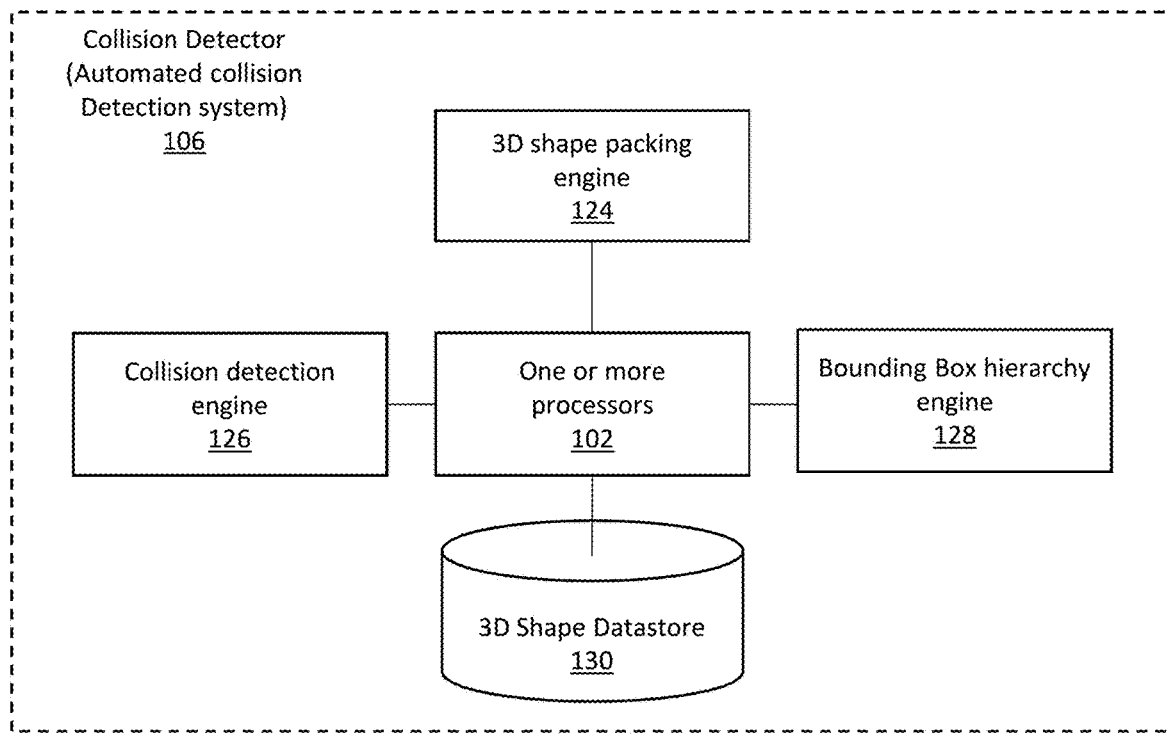
FIG. 2B is a schematic example of a collision detector (e.g., an automated collision detection system).

In FIG. 2A the system for automatically creating an orthodontic treatment plan of a patient may include one or more processors 102. The treatment plan solver set of instructions may operate on the one or more processors. The system may also include a collision detector 106, which may also operate on the one or more processors. The system may also include a memory that is part of or coupled to the one or more processors, and which stores computer-program instructions, that, when executed by the one or more processors, perform a computer-implemented method that may include collecting (e.g., forming, reading, receiving, etc.) a digital model of a surface for each tooth of a plurality of a patient's teeth by packing a plurality of 3D shapes to approximate (e.g., model, form, etc.) the surface for each tooth, wherein the 3D shapes each have a core that is a line segment or a closed plane figure and an outer surface that is a constant radius from the core. As will be described in greater detail below, the collision detector 106 may include hardware, software and/or firmware for packing the tooth or other feature, and modeling the surface with the 3D shapes such as the capsules. The system may also be configured to collect (e.g., to receive, read, etc.) treatment preferences. The preferences may be collected into a treatment preference datastore 115. The preferences may also include treatment details datastore 117. The system may form, for the surface for each tooth of the plurality of the patient's teeth, a hierarchy of bounding boxes enclosing the plurality of 3D shapes. This may be performed using the processor and/or as part of the collision detector. The tooth positions for the plurality of the patient's teeth may be passed from a treatment plan solver 101 to a collision detector (see, e.g., FIG. 2B. The solver may collect a digital model of the patient's teeth to be modified by the treatment plan (collecting may include receiving/loading from an external source, retrieving from a memory, including a patient teeth datastore 123 or other memory, or the like).

The one or more processors 102 or any of the other elements (e.g., numeric function engine 107, numeric function building engine 109, comprehensive final position engine 111, collision detector 106, solution vector mapping engine 113, etc.) may be connected in any appropriate manner and any of these elements may also be connected to the datastores (e.g., patient teeth datastore 123, treatment targets datastore 119, treatment details datastore 117, treatment preferences datastore 115, and numeric limits datastore 121, etc.).

The numeric function building engine 109 may be used to select a plurality of numerically expressed treatment targets (e.g., from a treatment targets datastore 119 or other memory or input accessible to the one or more processors) based on the set of treatment details (which may be accessed from the treatment details datastore 117 or other accessible memory/input), the set of treatment preferences (which may be provided by the treatment preferences datastore 115 or other memory/input) and the comprehensive final position of the patient's teeth. The comprehensive final position of the patient's teeth may be provided by the comprehensive final position engine 111 or from a memory storing the comprehensive final position.

The solver may also include a numeric function minimizing engine 107 which may combine the plurality of numerically expressed treatment targets to form a single numerical function. This single numerical function may then be minimized to solve for one or more solution vectors using the collision detector 106 and a set of numeric limits that may be provided, for example, from a numeric limits datastore 121 or other memory/input. The numeric limits may be selected for the single numerical function based on the set treatment preferences (e.g., from the treatment preferences datastore 115 or other memory/input).

The solution vector typically includes all of the stages forming the treatment plan, and may be stored in a memory, and/or displayed, and/or transferred. In some variations the solution vector may be converted into a treatment plan using a solution vector mapping engine 113 to map the solution vector to a treatment plan, wherein the treatment plan includes a final tooth position that is different from the comprehensive final position of the patient's teeth.

Figure 2C:
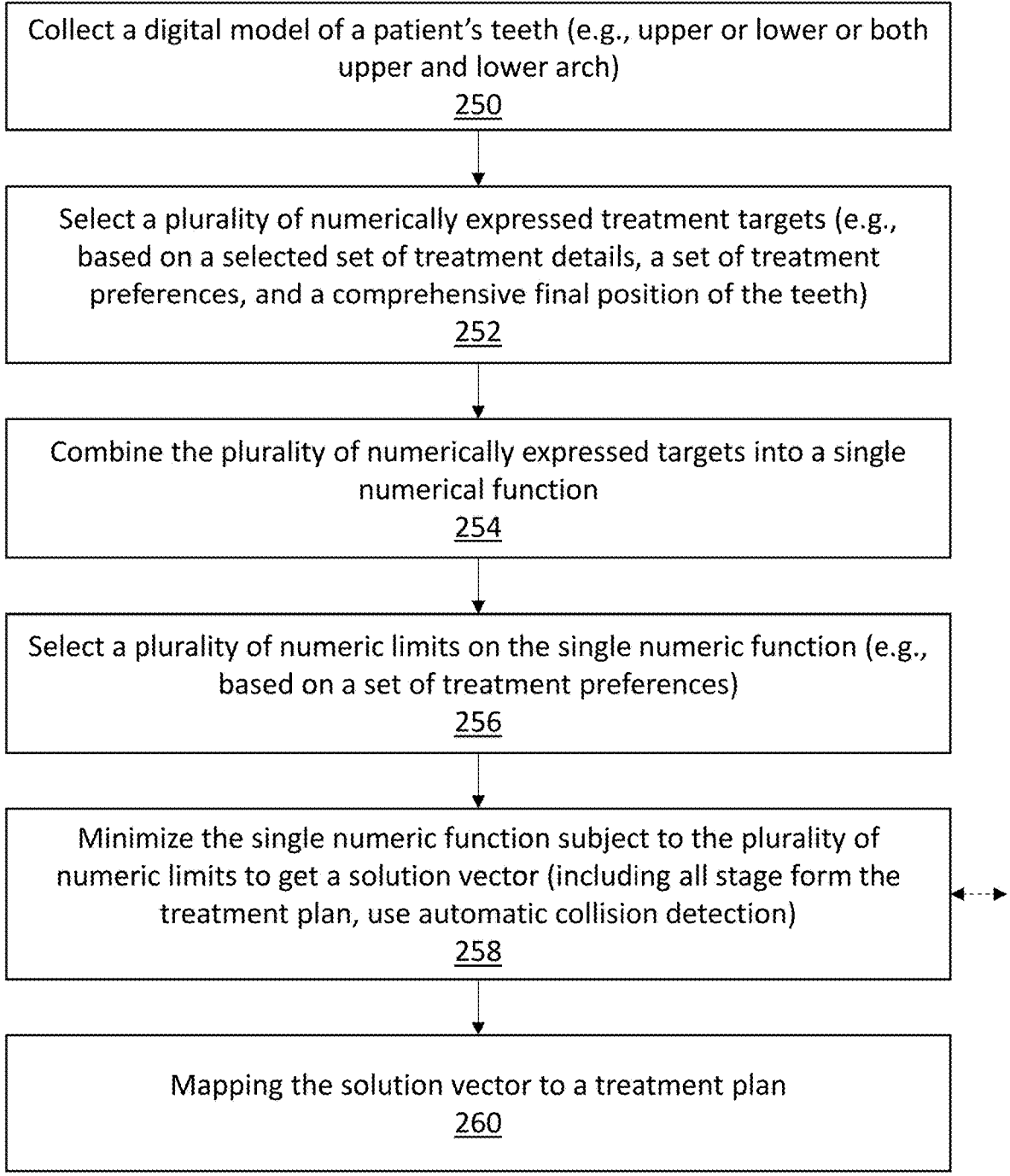
FIG. 2C schematically illustrates one example of an automated method of creating one or more treatment plans to align a patient's teeth (e.g., using a series of removal aligners to be worn in a sequence).
Figure 2D:
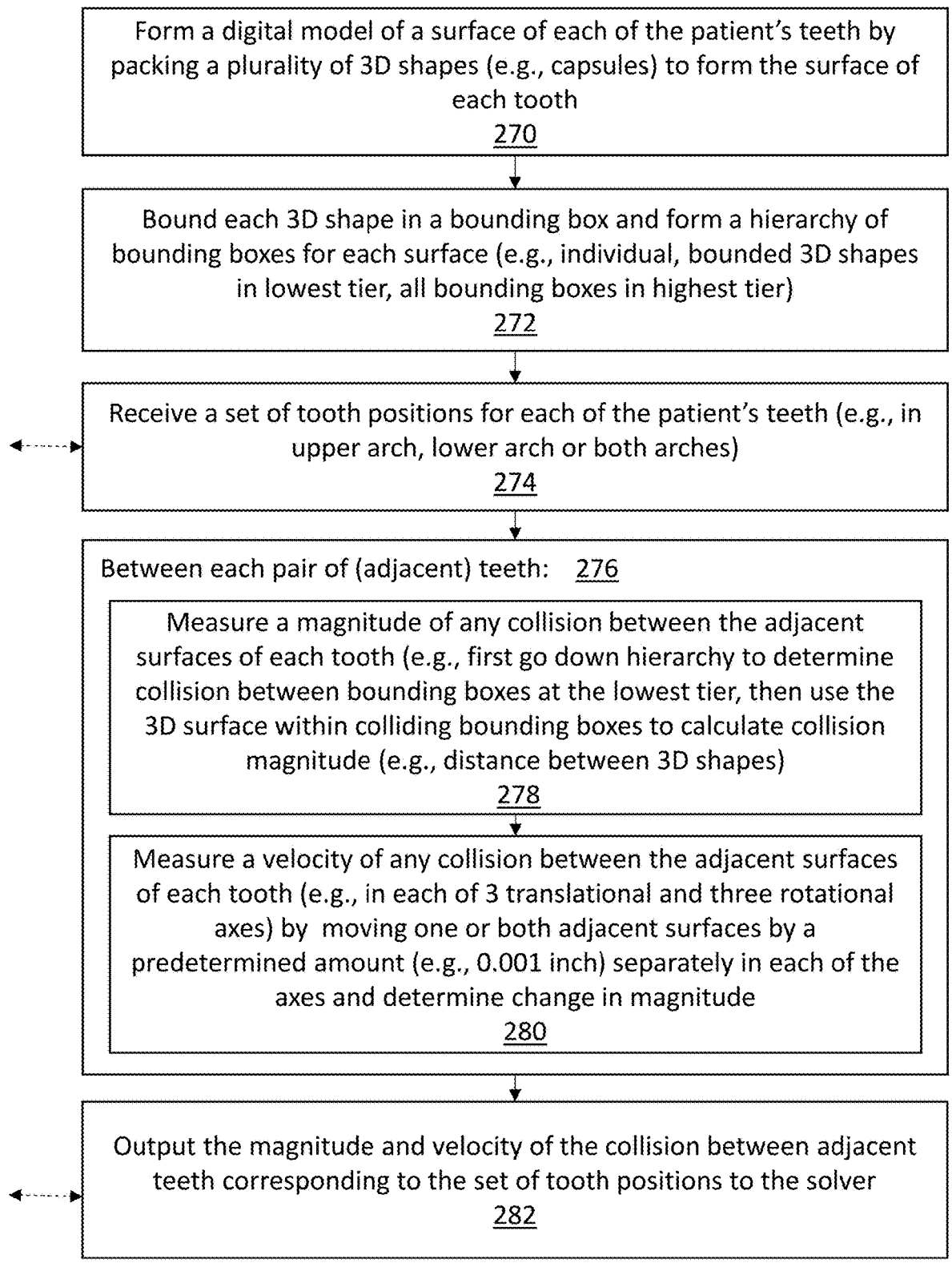
FIG. 2D schematically illustrates one example of an automatic collision detection method that may be used, e.g., by the treatment plan solver performing an automated treatment planning method. The illustrated automatic collision detection method may be performed, for example, by a collision detector.

FIG. 2C schematically illustrates a method of creating a treatment plan to align a patient's teeth using a plurality of removable aligners to be worn in sequential stages. In this example, the first step is to collect a digital model of a patient's teeth (e.g., upper or lower or both upper and lower arch) 250. This may include, for example, receiving, in a processor, a digital model of a patient's teeth. The method may also include selecting a plurality of numerically expressed treatment targets (e.g., based on a selected set of treatment details, a set of treatment preferences, and a comprehensive final position of the teeth) 252. The plurality of numerically expressed targets may then be combined into a single numerical function 254, and a plurality of numeric limits on the single numeric function (e.g., based on a set of treatment preferences) may be selected 256. The single numeric function may be minimized subject to the plurality of numeric limits to get a solution vector (including all stage form the treatment plan, use automatic collision detection) 258. The process of solving (minimizing) for the solution vector may implement the collisions detection method (FIG. 2D, described in greater detail below). The solution vector may then be mapped to a treatment plan 260.

Method of Manufacturing a Series of Aligners

Figure 3:
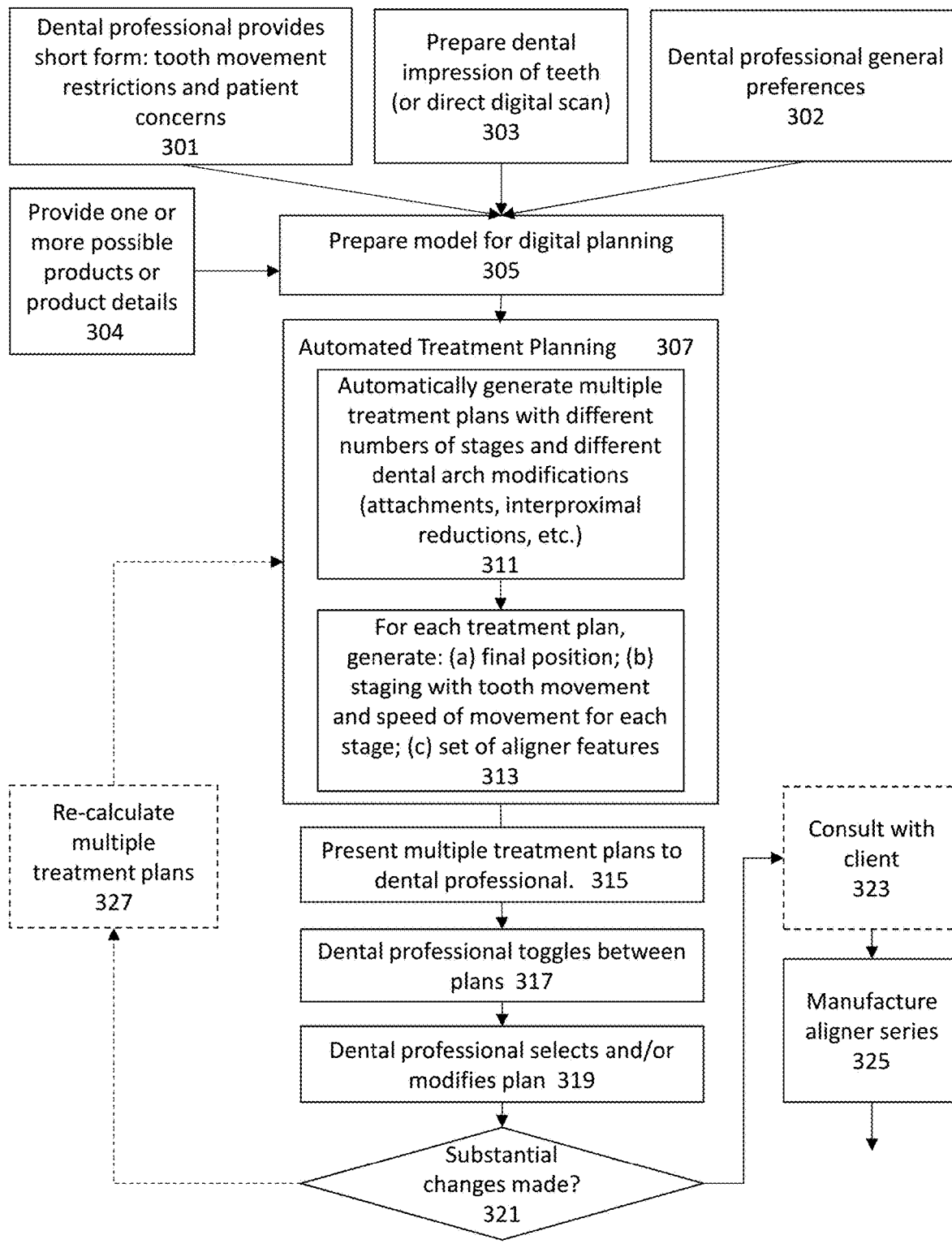
FIG. 3 illustrates an example of a method for manufacturing a series of aligners for a patient's teeth in which a plurality of treatment plans specific to the patient's teeth, representing partial treatment plans, having a fixed number of different stages and variations of these fixed number stages are all pre-calculated and included and displayed in real-time to allow the user to interactively select and/or modify a treatment plan for an orthodontic treatment. The method of manufacturing the series of aligners may include an automated method of creating one or more treatment plans or a treatment plan solver configured to perform the automated method of creating one or more treatment plans and/or an automatic collision detection method or a collision detector configured to perform an automatic collision detection method.

FIG. 3 is an overview of a method for manufacturing a series of aligners for a "partial treatment" plan. A partial treatment plan is a plan for which only a limited series of aligners is used to treat the patient; this limited number of aligners may be a predetermined number (e.g., 7, 10, 12, 16, 26, etc.) that is less than the total number that it may take to optimally correct the patient's malocclusions fully, addressing all of the clinically resolvable conditions (also referred to as treatment goals). In a partial treatment plan, the fixed number of aligners in the series may be configured (by configuring the treatment plan) to instead address some of the treatment goals within the limited number of stages defined, and approaching as closely as possible to the ideal realigned configuration without either creating new malocclusions or exacerbating existing malocclusions.

In FIG. 3, the method starts by collecting from the patient (and by the user, e.g., dental professional), a model of the patient's teeth 303, as well as any conditions (e.g., tooth movement restrictions) or preferences for treatment 301; the method or apparatus may also optionally identify any general preferences that are specific to the dental processional 302, and that may be applied to all of that dental professional's patients. In addition (and optionally) the method or apparatus may also provide an indication of the type of dental product (e.g., the type of dental/orthodontic products to be used to treat the patient 304. All of this information, and particularly the prescription information, may be completed in a relatively short (e.g., 2-25, 2-20, 2-15, etc. lines) form or virtual survey. The user may submit this information to a treatment plan optimizing generator, which may be located at a remote site. The treatment plan optimizing generator, which is described in detail below, may use this information to generate a plurality of treatment plans. For example, the treatment plan optimizing generator may first prepare the model 305, e.g., by digitizing it if it is not already a digital model, and by segmenting the digital model into individual teeth, gingiva, etc. Once prepared, the automated treatment planning 307 may be performed to automatically generate multiple treatment plans using, e.g., different numbers of stages; for each stage multiple variations including different treatment properties (e.g., IPR, attachments, etc.) may also be generated 311. Each treatment plan is complete, and may be used to build an aligner series. For example, each treatment plan may include a new (and potentially unique) final position for the patient's teeth at the end of the treatment, staging showing the tooth movement and speed of movement for each stage (e.g., key frames) and a set of aligner features 313. The corresponding aligner features may include the location of the attachments, etc.

This automated treatment planning may therefore use a treatment plan optimizing generator multiple times, each time providing slightly different treatment details and/or targets, while annotating each treatment plan with an indicator of what constraints and/or treatment targets were used to generate that treatment plan, including, for example, the fixed number of stages. The resulting multiple treatment plans may be collected into a single set (e.g., an array) and all of these treatment plans submitted back to the user via, e.g., a user interface to provide meaningful and interactive display, selection and/or manipulation of the treatment plans 315. The user (e.g., dental professional) may then, using the interactive display, in real time, toggle between the multiple plans, and select one or a subset of treatment plans 319. Optionally, the user may modify one or more plans 319; if the user modifies a treatment plan in a manner that exceed the pre-calculated plurality of treatment plans 321, then the modifications may be transmitted to back to the automated treatment planning subsystem (including the treatment plan optimizing generator) to generate additional treatment plans including the user's modifications 337. These new treatment plans may replace or supplement the plans already pre-calculated.

Optionally, once a subset of treatment plans has been selected from the larger array of treatment plans, the user may present the subset of treatment plans to a subject 323. The subject may be consulted to provide an indication (e.g., by showing the final stage/teeth position) of the orthodontic effect achievable by each treatment plan. Either the user or the subject (or both) may decide which treatment plan to choose, and the selected treatment plan may be forwarded on for fabrication/manufacturing 325 as discussed above.

Figure 4:
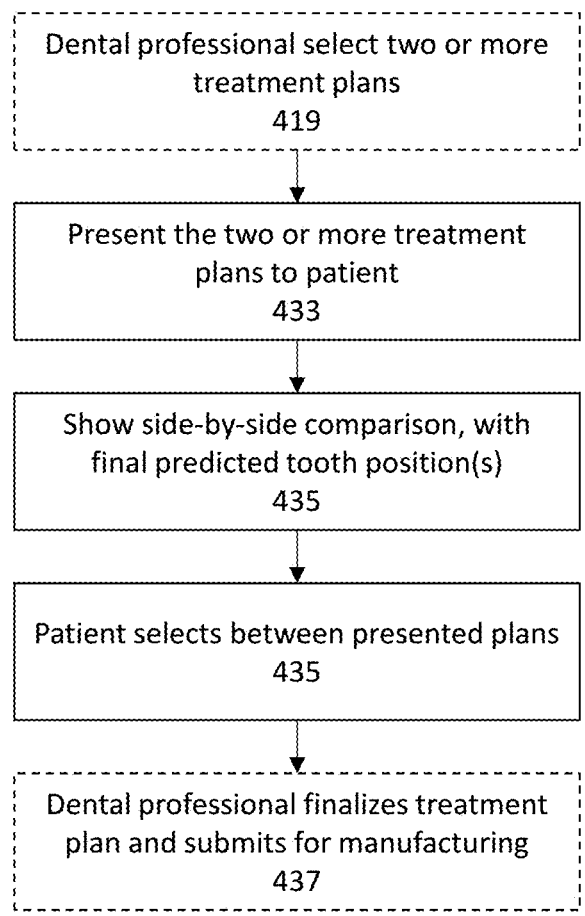
FIG. 4 is an illustration of a method for consulting with a patient by interactively showing them a subset of the treatment plans (e.g., selected by the user).

FIG. 4 provides additional detail on one example of a consultation mode of operation of the system described herein. In this example, after the dental professional has selected two or more dental pans 419 (see also FIG. 3, 319), two or more of these dental plans may be presented to the patient 433, allowing the patient to select between them. In addition to the image(s) of the teeth, including at least the last positon of the treatment plan, in some examples, metadata indicating the number of stages/length of treatment, and/or the treatment properties used to generate the particular treatment plan, etc., may be displayed as well. The display may be side-by-side 435 or it may be sequential, etc. The patient may then select between the presented plans 435. Finally, and optionally, the user may finalize the treatment, and the selected treatment plan may be submitted for manufacturing 437.

Figure 5:
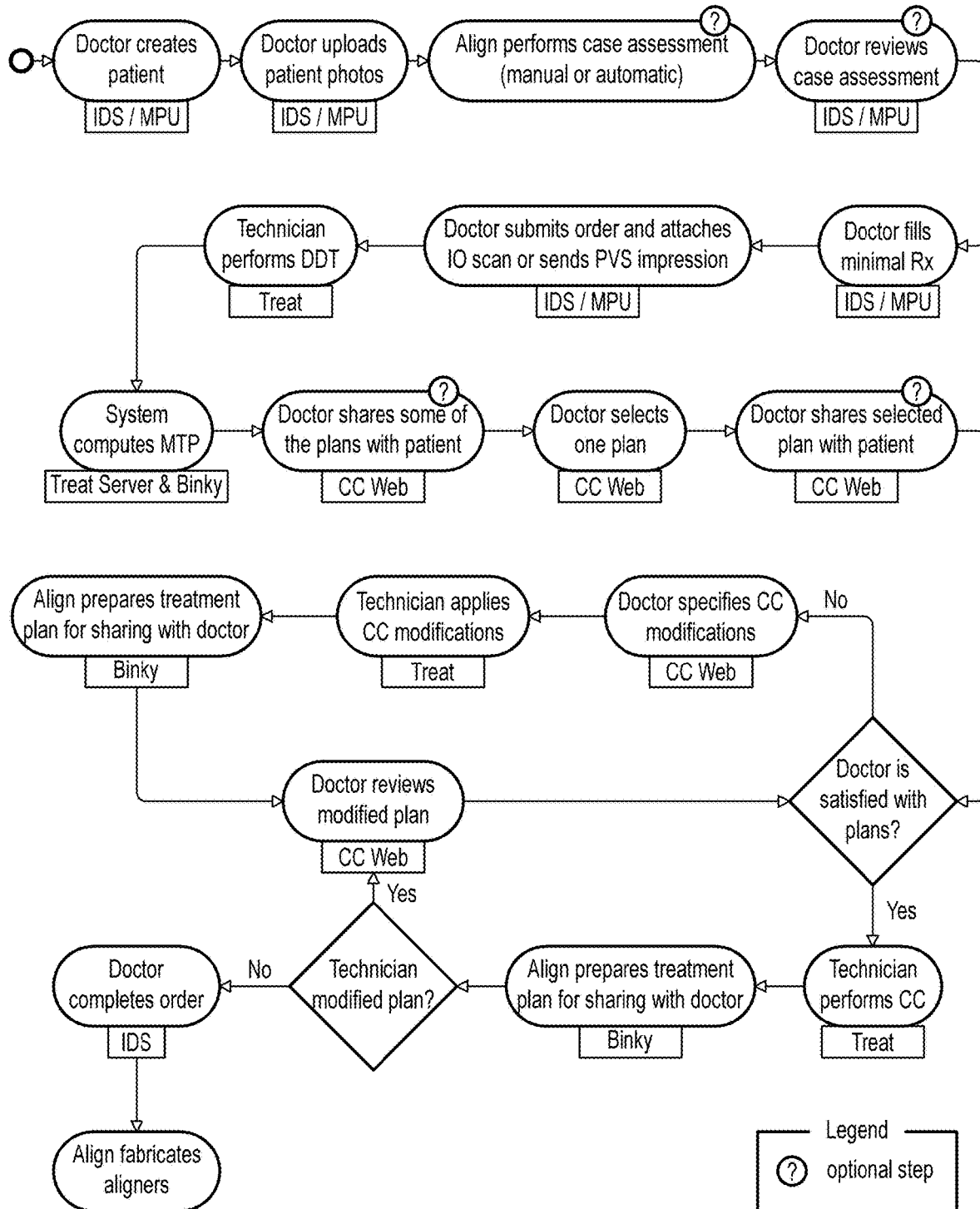
FIG. 5 is an example of a detailed process chart for designing, selecting and/or modifying a treatment plan and for manufacturing the selected treatment plan.
Figure 6A:
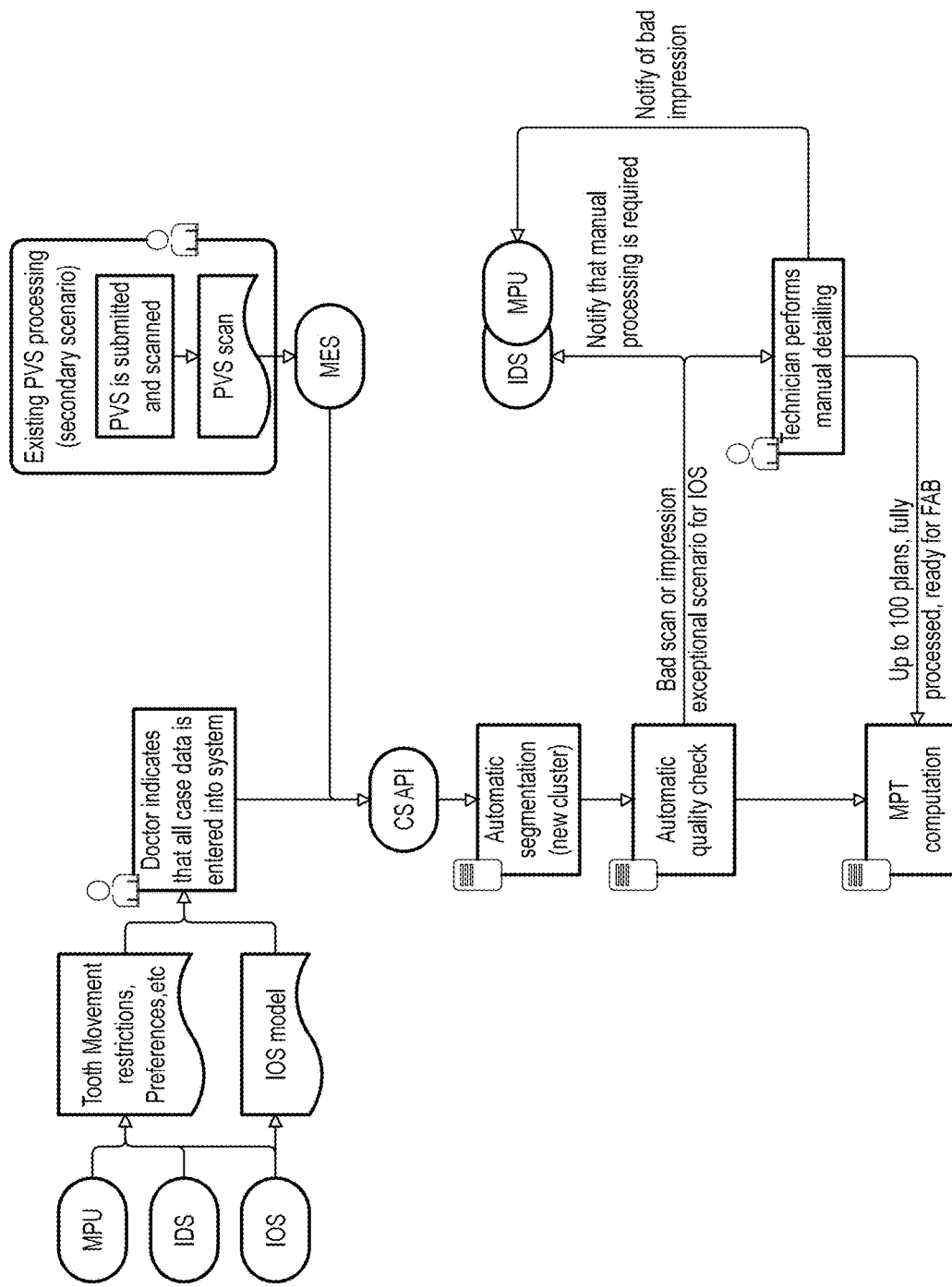
FIGS. 6A-6B is another example of a detailed process chart for designing, selecting and/or modifying a treatment plan and for manufacturing the selected treatment plan.
Figure 6B:
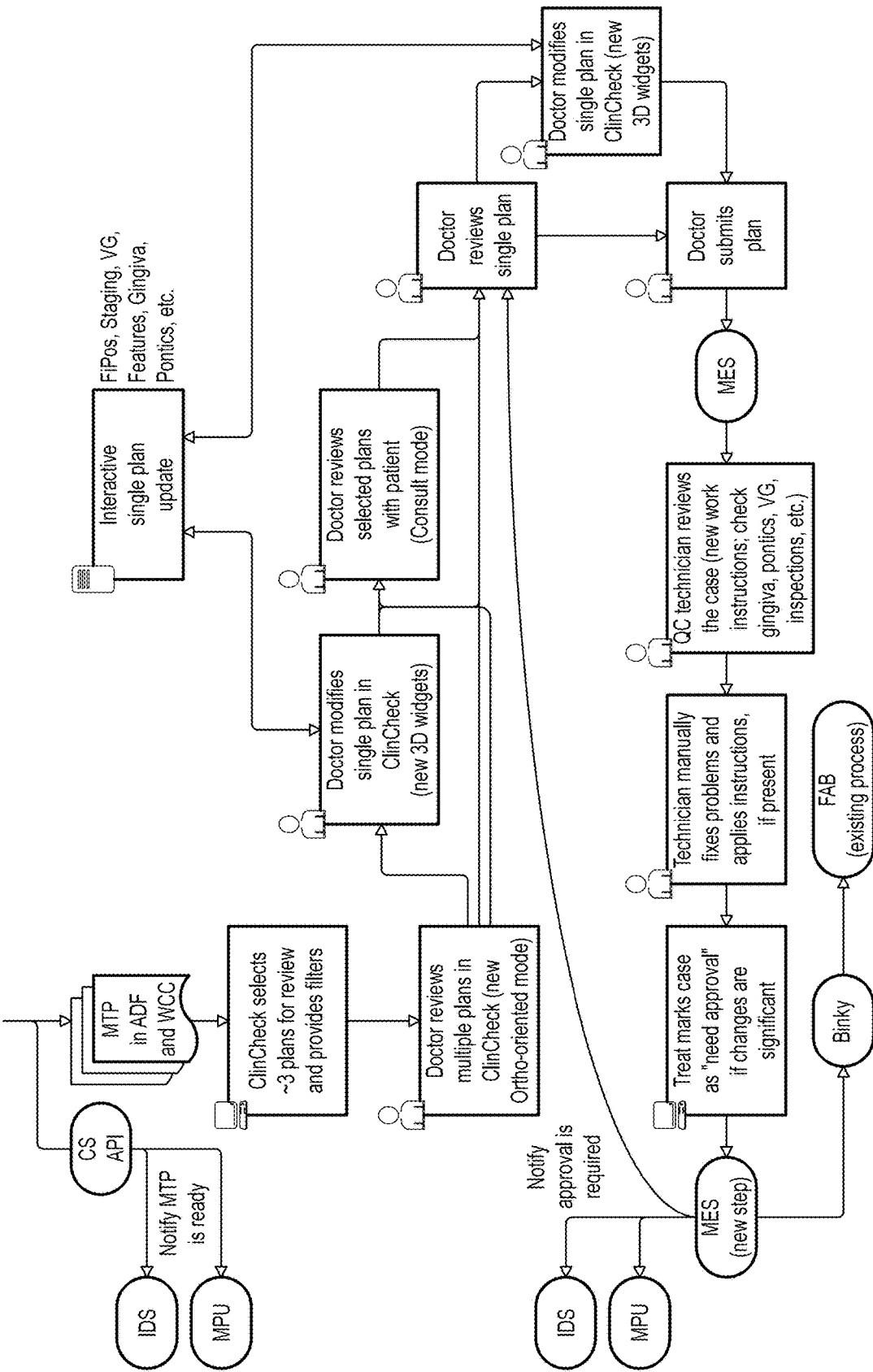

FIGS. 5 and 6A-B provide more detailed examples of possible methods for manufacturing a sequence of aligners for a patient. In FIG. 5, the user is presumed to be a doctor, through the user may be any dental professional. The user may first open a record for the patient, including any photos, using a user interface (IDS, a portal that the user may log into to access an account). A preliminary (automatic or manual) assessment may be performed to determine if the patient is a good candidate for the procedure ("case assessment"), and the user may review the case assessment. Thereafter, the user may submit a minimal patient prescription (e.g., indicating treatment goals, constraints, etc.). The user may further submit a model of the patient's teeth to the remote site for processing as mentioned above, to produce a digital model that is adequate for automatic treatment pan generation. In some cases a technician may perform digital "detailing" of the digital model to prepare it for processing. The treatment plan optimizing generator may then be used to automatically generate an array of alternative treatment plans (MTP) as discussed above. Thereafter, a user interface configured to allow interactive display of a plurality of different alternative treatment plans ("CCWeb") may be used to review and select, and in some variations, modify, the treatment plans in the array of treatment plans. The patient may be consulted, as discussed above. Once the user selects a single treatment plan, and is satisfied with the treatment plan, the user may then transmit the selected treatment plan to the manufacturer (technician) who may (optionally) review and send a finalized version of the treatment plan for final approval. Once approved, the treatment plan, including all of the stages of aligners, may be fabricated using the treatment plan either directly or converting it into a manufacturing format. If the user is not satisfied with the treatment plan, it may be modified.

FIGS. 6A-6B show a similar work flow to that shown in FIG. 5. In FIGS. 6A-6B, the user is presumed to provide the digital model of the patient's teeth at the start (e.g., by digitally scanning the patient's teeth).

Figure 7A:
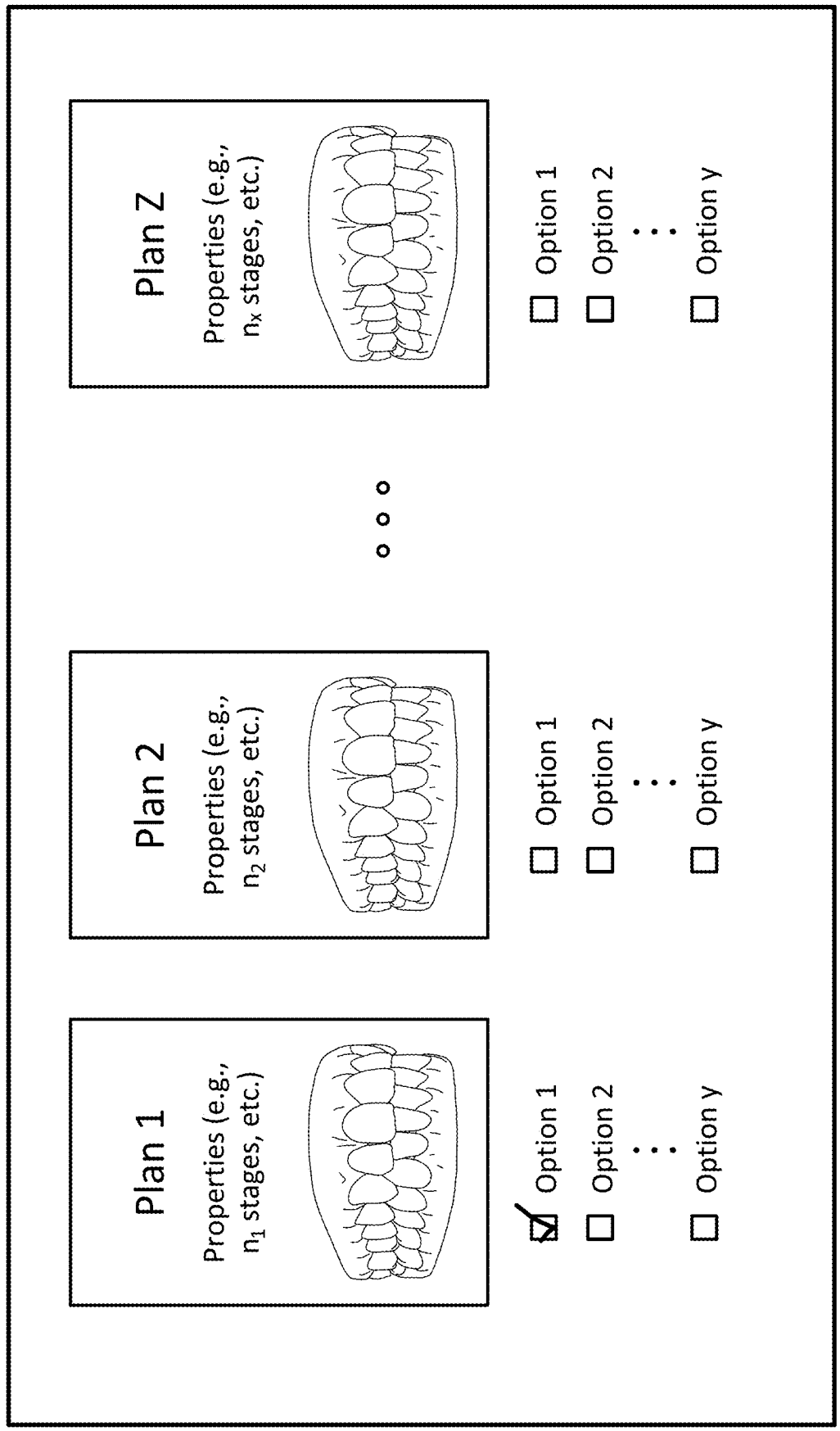
FIG. 7A is an example of a display for simultaneously showing, in real time, multiple treatment plans, including filters for toggling between treatment plans that are variations of fixed-length (e.g., "partial") treatment plans having a preset/predetermined number of stages.
Figure 7B:
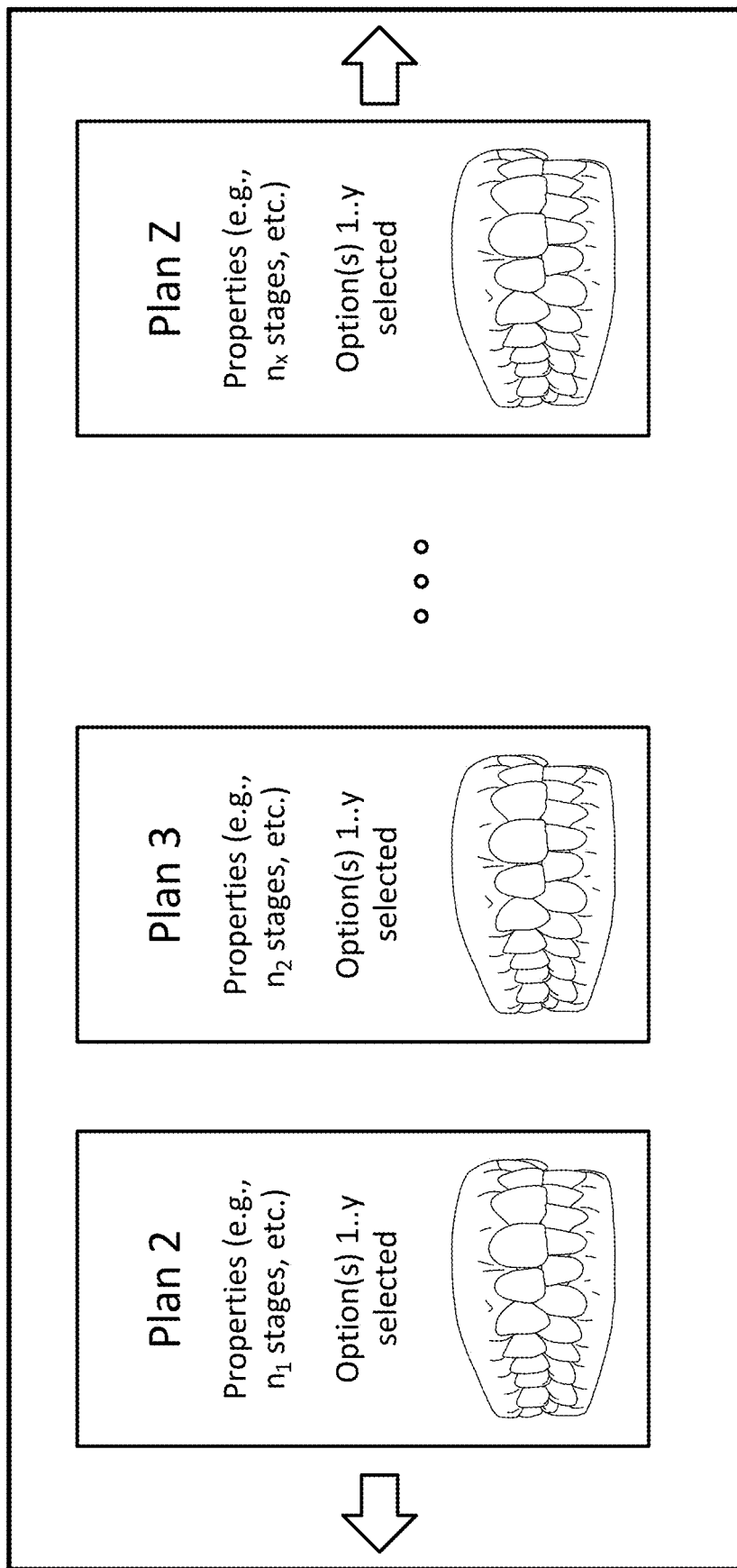
FIG. 7B is another example of a display for simultaneously showing, in real time, multiple treatment plans.

FIGS. 7A and 7B illustrate examples of an interactive display of a plurality of treatment plans to allow a user to select between the treatment plans and/or modify the treatment plans as quickly and efficiently as possible. In FIG. 7A, the display shows the final stage (final configuration) of each of the plurality of treatment plans. In this example, the plans are aligned side-by-side based on the number of stages ($n_1$, $n_2$, ... $n_x$). Each of these plans also includes optional variants (option 1, option 2, etc.) which may be displayed when the user control (box) is selected, which may be indicated by a check, as shown in FIG. 7A.

FIG. 7B is similarly to FIG. 7A, but lists each treatment plan as part of a ribbon that may be moved by sliding left or right, for example. Any of these user interfaces may show additional representations of the stages, either as key frames and/or as tooth representations.

Figure 7C:
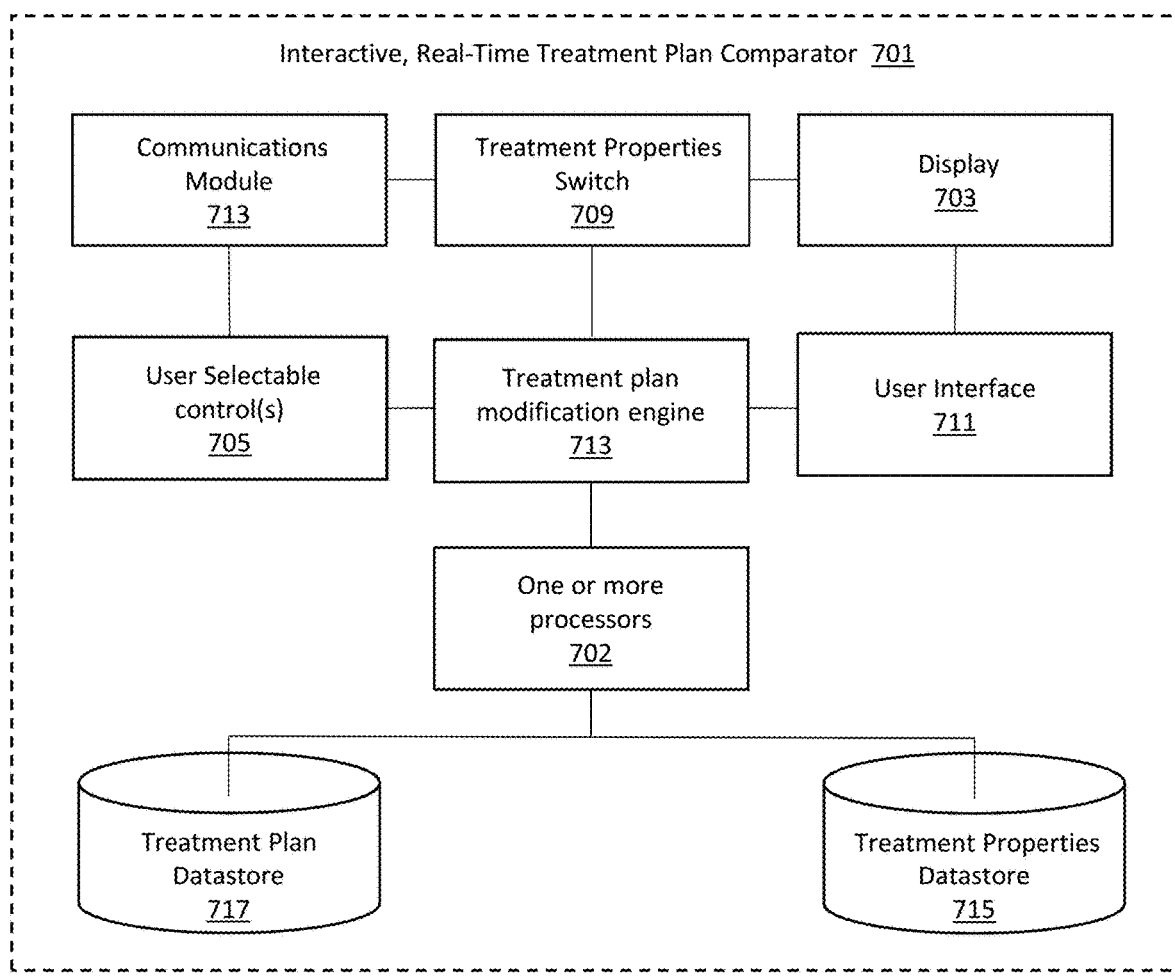
FIG. 7C is a schematic example of an interactive real-time treatment plan comparator.

FIG. 7C illustrates an example of a system. This system 701 is configured to provide interactive, real-time and dynamic comparison between different treatment plans. In FIG. 7C the system 701 includes a plurality of modules that may operate together in any combination to provide real-time (or near real-time) interactive, dynamic display for comparison between multiple full orthodontic treatment plans, including rapidly toggling between different complete treatment plans to illustrate the differences between treatment plans having modified inputs (e.g., with/without IPR, extraction, etc.). For example, in FIG. 7C, the system may include a user interface 711 for displaying (side-by-side and/or sequentially) different treatment plans. The treatment plans may be calculated as described herein, using a variety of different treatment preferences and/or treatment details. The treatment plans may be arranged in a grouping of any type (e.g., an array), and may be collected by the system (e.g., received, etc.) from a treatment plan generating system (such as shown in FIG. 2A, above), and may be stored in a treatment plan datastore 717 for use by the system 701. Each treatment plan of the plurality of treatment plans may include a set of sequential stages for orthodontic movement of the patient's teeth including a final stage. The final stage may represent the final position of the patient's teeth. In particular, these systems may be used when at least three of the treatment plans have different numbers of sequential stages, and further wherein the array of treatment plans comprises two or more treatment plans having different treatment properties. The different treatment properties may be stored for later use by the system in the treatment properties datastore 715.

In operation the system may operate the user interface module 711 in conjunction with the user selectable controls 705 to allow the user to dynamically switch (toggle) between different treatment plans, which may be displayed on a screen or other display 703 of the system by showing one or more stages, including the last (final) stage (which may be represented by a digital model of the patient's teeth in this final position), and/or properties of the treatment plan, such as the number of steps/stages, the duration of treatment, the duration of stages, the rates of tooth movements, the movement of the teeth over time (e.g., by animation or still presentation), etc. The system may display images of the teeth at the final stage for each treatment plan of a subset of the treatment plans from the array of treatment plans on the screen. A treatment properties switch 709 module may provide real-time (or near real time) switching between images of the different treatment plans within the array of treatment plans, including switching between images of the various based on one or more user-selected controls on the screen.

The system may also include a communications module 713 (e.g., wireless module, such as Wi-Fi, Bluetooth, etc.). The communications module may allow the system to receive inputs and send outputs, such as, e.g., transmitting a selected one of the treatment plans for fabrication after the user has chosen the selected one of the treatment plans displayed on the screen.

Any of these systems may also be configured to allow the user to modify one or more of the treatment plans during the display, including modifying tooth position staging timing, etc. In FIG. 7C, the system includes an optional Treatment plan modification engine 713 that may be configured to allow the user to modify a treatment plan directly.

FIG. 7D illustrates one example of a method of manufacturing a series of aligners for a patient's teeth. In particularly, this method may allow the real-time analysis and review of a huge number of treatment plans, selection of one of these treatment plans, and fabrication of a series or sequence of aligners based on these treatment plans. For example, the method may include: gathering (e.g., collecting, including collecting from a remote site) an array of treatment plans specific to the patient's teeth, wherein each treatment plan in the array describes a set of sequential stages for orthodontic movement of the patient's teeth including a final stage, further wherein at least three of the treatment plans have different numbers of sequential stages, and further wherein the array of treatment plans comprises two or more treatment plans having different treatment properties 721. Images of the teeth after the final stage for each treatment plan of a subset of the treatment plans from the array of treatment plans may then be displayed on the screen 723. The method may then switch, in real time, between images of the teeth at the final stages for different treatment plans within the array of treatment plans based on one or more user-selected controls on the screen 725. Finally, a selected one of the treatment plans for fabrication that the user has chosen may be displayed on the screen and transmitted for fabrication. Once fabricated they may be sent to the patient or to the patient's dental/orthodontic provider for distribution to the patient.

FIG. 8A shows another example of a user interface that may be used to interactively review, modify and/or select a treatment plan. In FIG. 8A, a patient record may be selected, and monitored using the interface. For example, the user interface may allow the user to interactively review the plurality of treatment plans generated; the user interface shown in FIG. 8A shows an example in which the patient's teeth model has already been submitted along with the user preferences, constrains, etc. and the treatment plan optimizing generator has already been used to generate an array including a plurality (e.g., 12 or more) of treatment plan variations.

FIG. 8B is another example of a user interface that may be used at the start of a patient treatment plan. In FIG. 8B, the user interface is configured as an interactive prescription form that may allow the user (e.g., clinician, dentist, orthodontist, dental technician, etc.) to select the patient type (e.g., child, teen, adult), and enter information about the patient (e.g., name, age, images, etc.), and/or enter treatment/protocol preferences (e.g., eruption compensation, interproximal reduction preferences, attachment preferences, etc.). The user interface may also suggest one or more preferences from a library or database of preferences. In some variations the prescription form may also allow the user to manually enter treatment preferences. In FIG. 8B the prescription form also allows the user to select the type of input of the patient dentition, such as from an intraoral scan and/or a scan of a mold or impression of a patient's teeth.

FIGS. 9A-9B (similar to FIG. 7A-7B) illustrate a user display that shows three (in this example) variations, side-by-side, of treatment plans for a patient ("Joe Smith"). As indicated on the right of the user interface, the patient has upper and lower crowding and an open bite ("malocclusion analysis"). The therapy may be configured to address these target goals. In FIG. 9A, the three sets of treatment plans are shown, with user controls allowing selection of variations (that will swap with the variation treatment plan). On the left, a 26 stage treatment plan is shown; in the middle, a 14 stage treatment plan is shown; on the right, a 7 stage treatment plan is shown. For each treatment plan, variations include: with/without IPR, and with/without aligner attachments. By selecting the user control on the screen (or on an input such as a keypad, mouse, etc.), the user may see what effect adding/removing these features has. Further, any of these treatment plans may be selected and put into a subset for display to the subject as part of a consultation mode. Finally, below the image of the final stage position of the teeth for each variations is a textual description of the malocclusion analysis specific to that treatment plan. In FIG. 8, all three basic parameters resolved the upper and lower crowding and both the 26 and 14 stage treatment plans addressed (and partially resolved) the open bite malocclusion. FIG. 9B shows the same basic user interface as FIG. 9A, but with the 26 stage treatment plan shown as a variation including both IPR and aligner attachment.

Figure 9C:
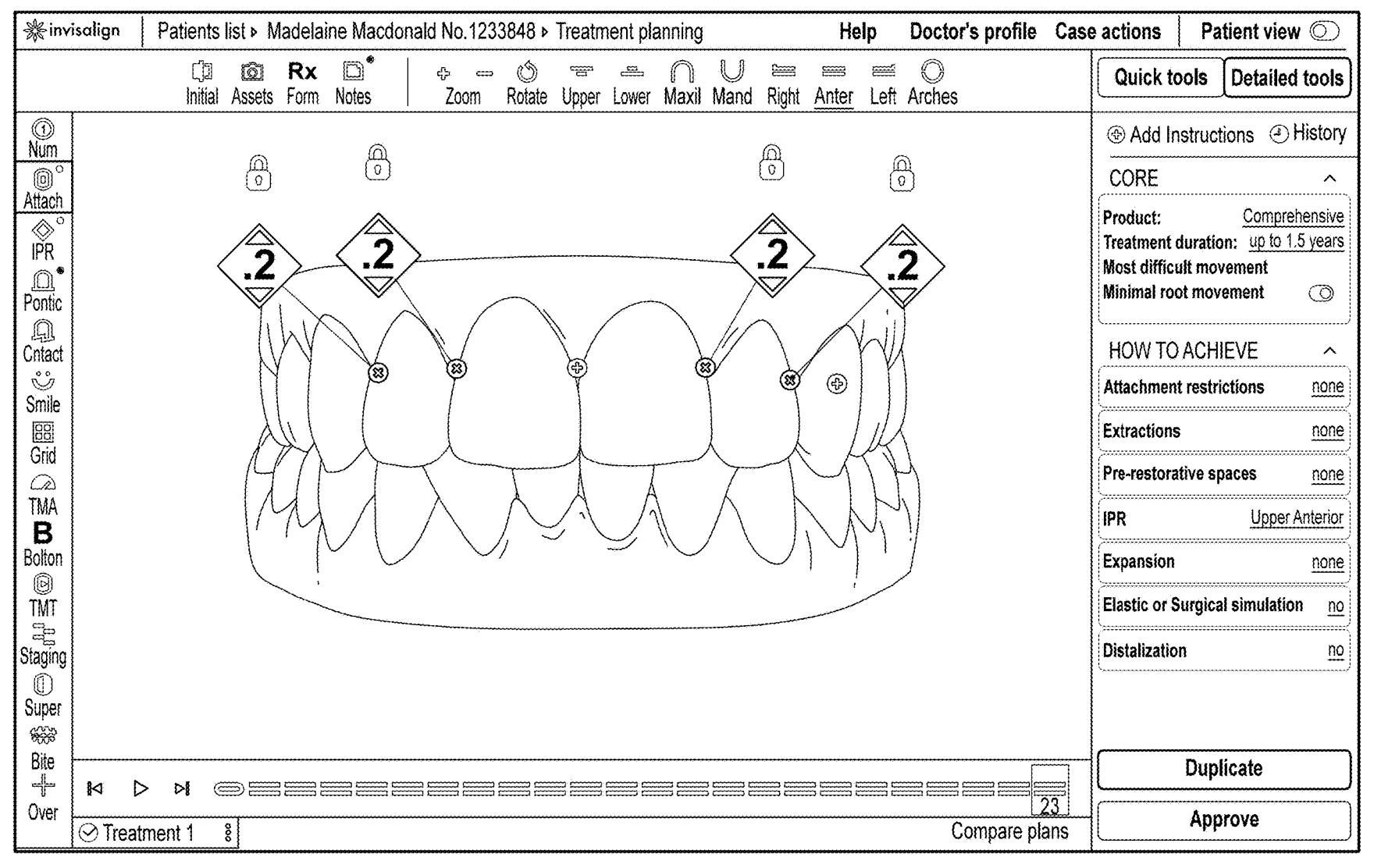

FIG. 9C is an example of a user interface showing an interactive treatment planning screen in which a model (3D digital model) of the patient's dentition is included in a large display window. In some variations either or both the upper and lower arches are shown a selected stage (or stages) of a treatment plan, and permitting the user to select and apply various digital tools to modify the treatment plan (e.g., changing tooth number, adding/removing or moving attachments, adding/removing/modifying IPR between selected teeth, adding/removing pontics to selected teeth, etc.), manipulate the 3D model of the teeth (e.g., rotate, zoom, show just upper, just lower, both upper and lower, change the angle of display of the tooth to one or more predetermined angles, etc.), manipulate the display, including selecting a different stage of the treatment plan and/or show an image of the patient's smile as predicted for any stage (or just the final stage) of the treatment plan, showing a grip, and/or showing one or more analytics (e.g., Bolton ratio, bite analytics, etc.

In FIG. 9C the user interface may also allow the user to both see and to modify the options applied in generating the treatment plan, including the name of the product (e.g., comprehensive, express, teen, etc.) having different properties for the proposed treatment plans. The properties (e.g., treatment duration/number of stages, minimal root movement, extractions, attachment restrictions, pre-restorative spacers, IPR, expansion (of dental arch) including which teeth to use for each, all, or some subset of these, elastic or surgical simulation, distalization, etc. The user interface of FIG. 9C may allow, as described above, any of the features of claims 9A-9B, including selecting/deselecting one or more parameters.

Figure 9D:
Figure 9E:
Figure 9F:
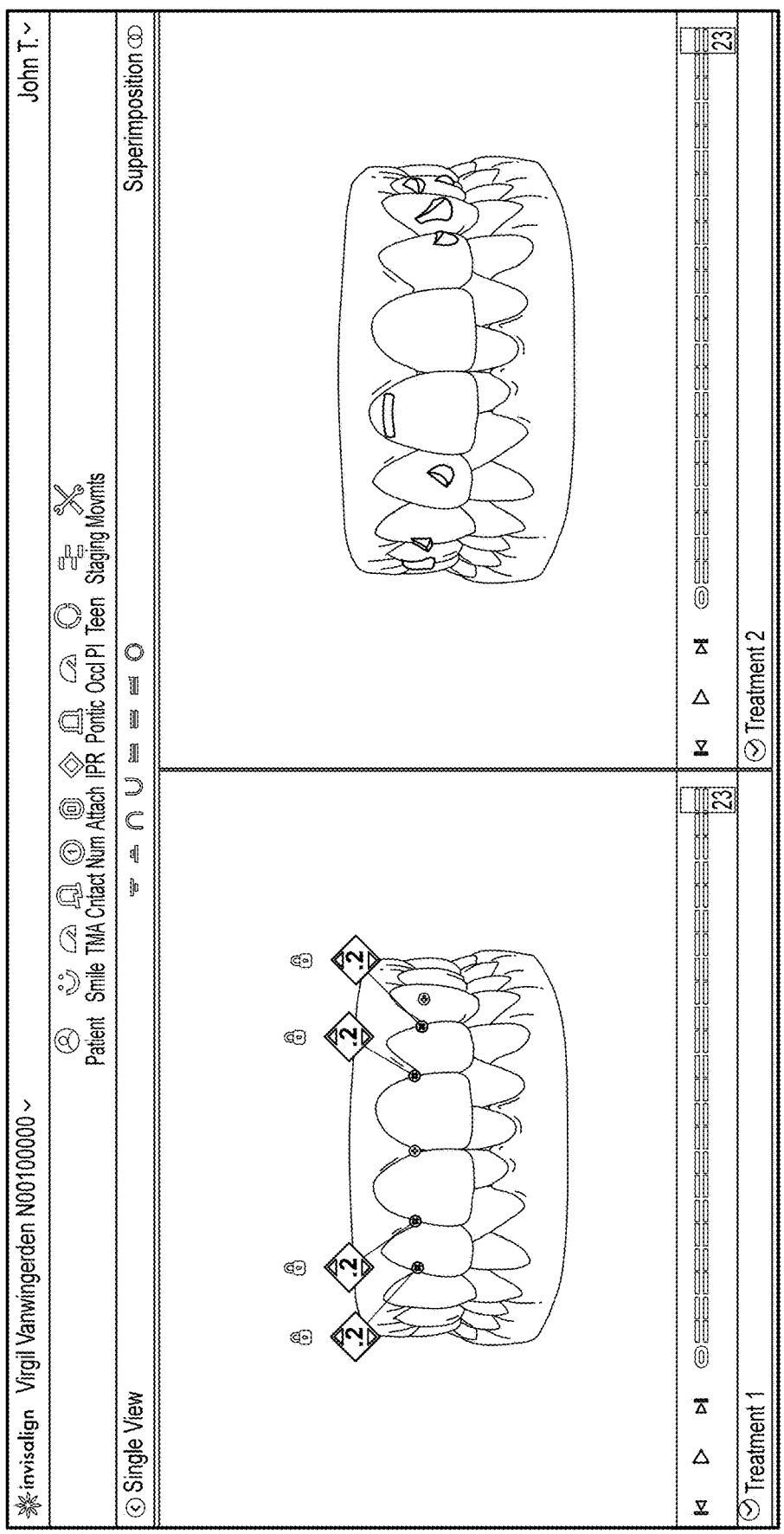
FIG. 9F is an example of a user interface configured for side-by-side comparison of one or more variables that may be considered when generating multiple treatment plans.

FIGS. 9D-9F all illustrate alternative user interfaces as described herein. In general the term 'user interface' may refer to the interface seen by the user (doctor, dentist, dental technician, etc.), although, as described below, in some variations any of these user interfaces, or similar structures may be presented to the patient, including by the user, as part of the treatment selection and/or design process and/or during the treatment process. For example, in FIG. 9D the user interface includes a window for showing one or both of the patient's dental arches at any stage of a proposed treatment plan (e.g., when a single treatment plan is selected or when only a single treatment plan is generated). The user interface may display the characteristics and/or user preferences that went into designing the treatment plan, such as the number or range of stages (e.g., a comprehensive plan having >21 stages), the amount of tooth movement (minimal or not), a description of the clinical goals (e.g., improving overbite, posterior cross bite, etc.), and aligner/staging features (e.g., pre-restorative spaces, IPR, expansion, proclination, extractions, elastic or surgical, distalization, attachments, etc.). The user interface may also provide 3D tools for manipulating the teeth and/or tools for modifying the treatment plan, and/or resubmitting for generating the new/revised treatment plan or series of plans. Finally, the user interface may allow the user to select/accept the treatment plan, so that the series of aligners may be transmitted for manufacture (e.g., which may include one or more additional quality control steps).

FIG. 9E is another example of a user interface, similar to that shown in FIG. 9D, but including additional 'tabs' allowing the user to select between proposed treatment plans for direct comparison; the functionality of the user interface may be otherwise the same as described above. Each treatment plan may be separately or jointly examined. In FIG. 9E, the user may toggle between treatment plans; in some variations, as described above, the user may be shown side-by-side windows allowing simultaneous comparison between two (or more) treatment plans, as illustrated in FIG. 9F. In this example a pair of different treatment plans generated for the same patient are shown side-by-side; the user may select one or both to rotate (in some variations the user interface may be allowed to permit either separate rotation of the respective 3D models of the patient's teeth when showing stages of the treatment plan, or the user interface may be configures so that moving one of the 3D models of the patient's teeth in a particular treatment plan may automatically move the other 3D model of the patient's teeth according to the second treatment plan.

Figure 9G:
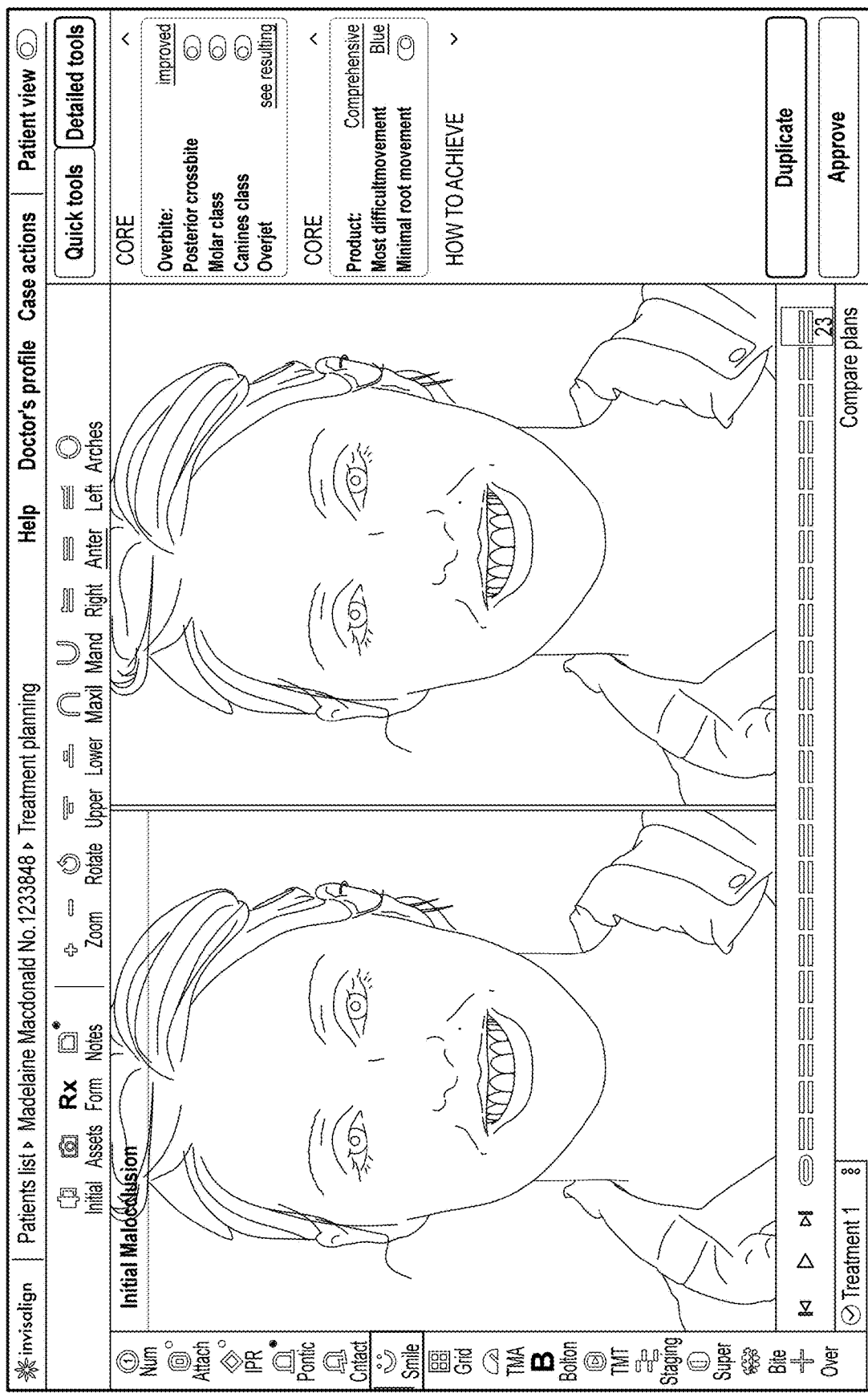
FIG. 9G is an example of a user interface configured to show 'before' and 'after' images of the patient's dentition, wherein the before treatment image is shown on the left, while the proposed/predicted outcome of a specified treatment plan is shown on the right.

In some variations the user interface may be configured to display a modified image of the patient's smile (e.g., the patient's teeth in a forward-facing image of the patient's face) at the conclusion of (or at any stage of) a treatment plan. FIG. 9G shows an image of an initial malocclusion (left image) for direct side-by-side comparison with a simulated image of the patient's smile following a particular treatment plan (right image); the specifics of the treatment plan are listed on the user interface (right side). In this example, the user may toggle between different treatment plans by toggling (in the controls on the right) various features on or off, such as overbite correction, posterior crossbite correction, molar class correction, overjet correction, IPR, attachment positions, number of stages (e.g., product), etc.

Figure 9H:
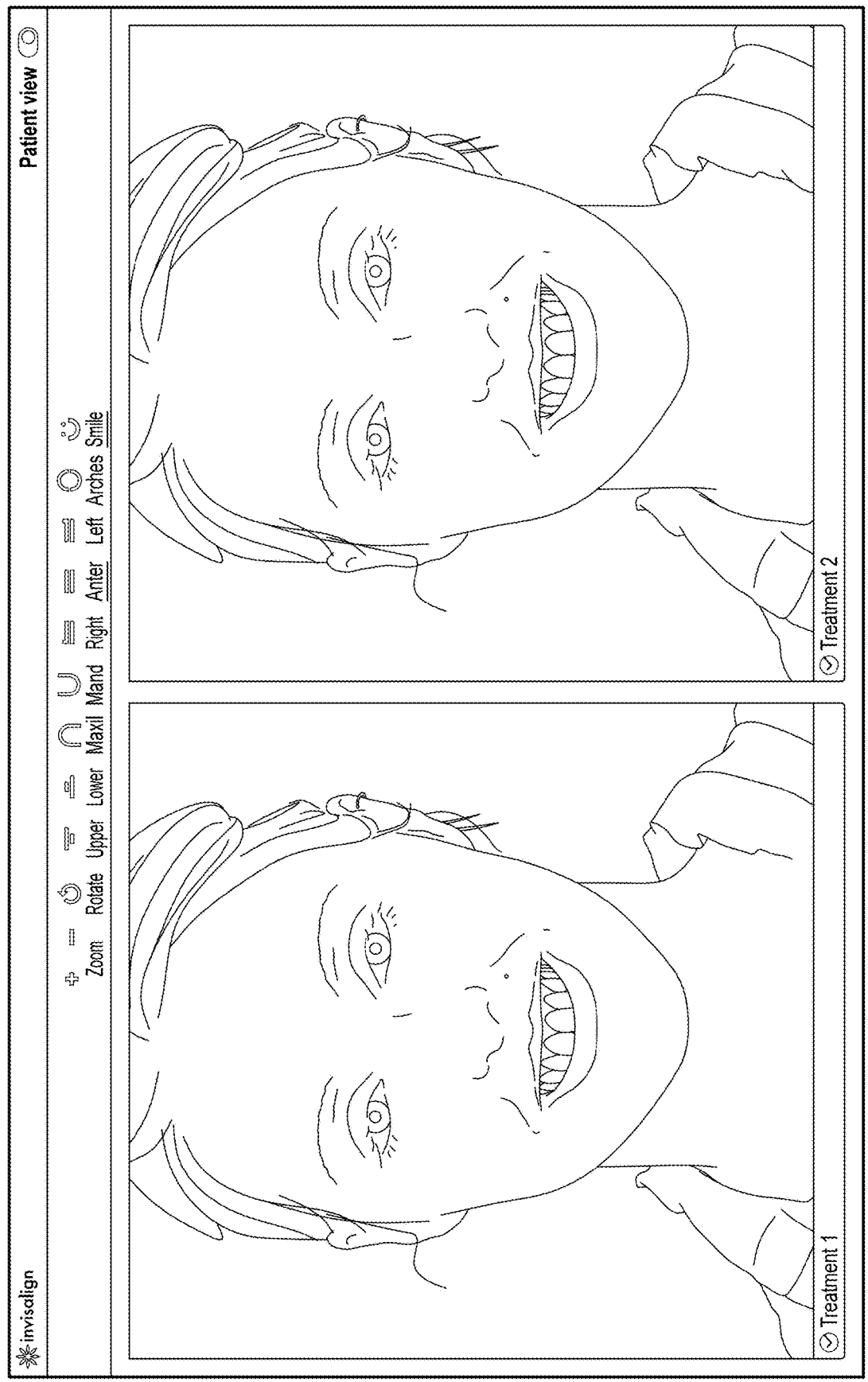
FIG. 9H is an example of a patient presentation user interface that may be provided to the patient to illustrate the predicted outcome of the treatment, and/or to allow a comparison between different treatment plans.

As mentioned, in some variations a specific output (including a specific user interface) for presenting one or more treatment plans to a patient may be used. FIG. 9H is an example of a patient presentation user interface that may be provided to the patient to illustrate the predicted outcome of the treatment, and/or to allow a comparison between different treatment plans. The user interface in FIG. 9H is a simplified version of the user interfaces discussed above, showing images of the smile (face) with a simulated patient tooth position, and/or images of the patient's teeth. The images may be manipulated by one or more controls (e.g., shown on the top of the user interface in FIG. 9H, including zoom, rotate, arch views/angles, etc.). In FIG. 9H, "smile" view is selected and the final tooth arrangement for each of two treatment plans is shown.

Figure 10A:
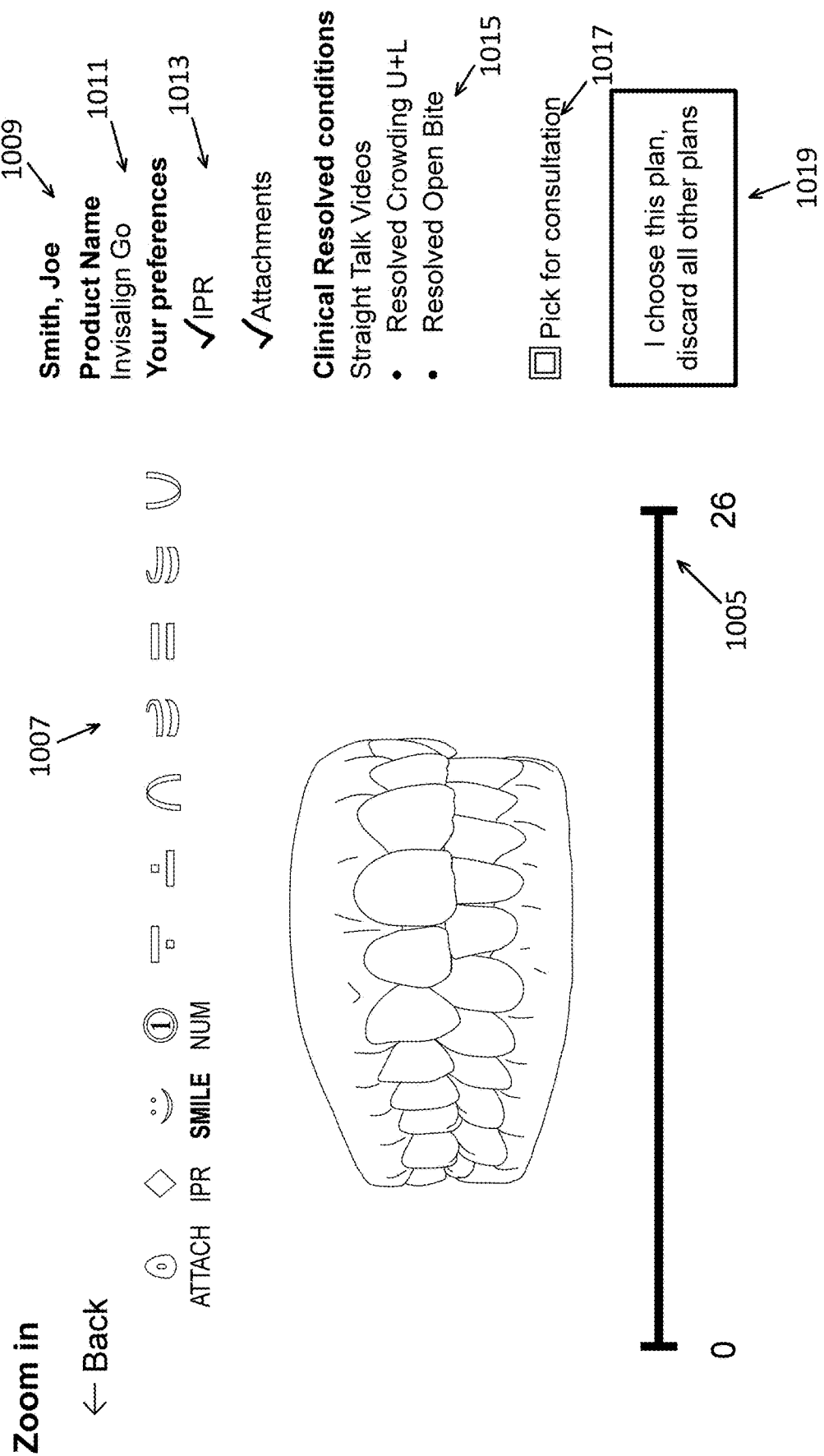
FIG. 10A shows a user interface (display) in which a 26 stage treatment plan including both IPR and aligner attachments is shown; controls on the screen (e.g., slider) allow the user to view the predicted tooth position in each stage.
Figure 10B:
FIG. 10B shows the user interface (display) of FIG. 10A, including the adjustments for spacing (shown by the + symbols) and/or leveling. Other tools may be included for modifying the treatment plan.
Figure 10C:
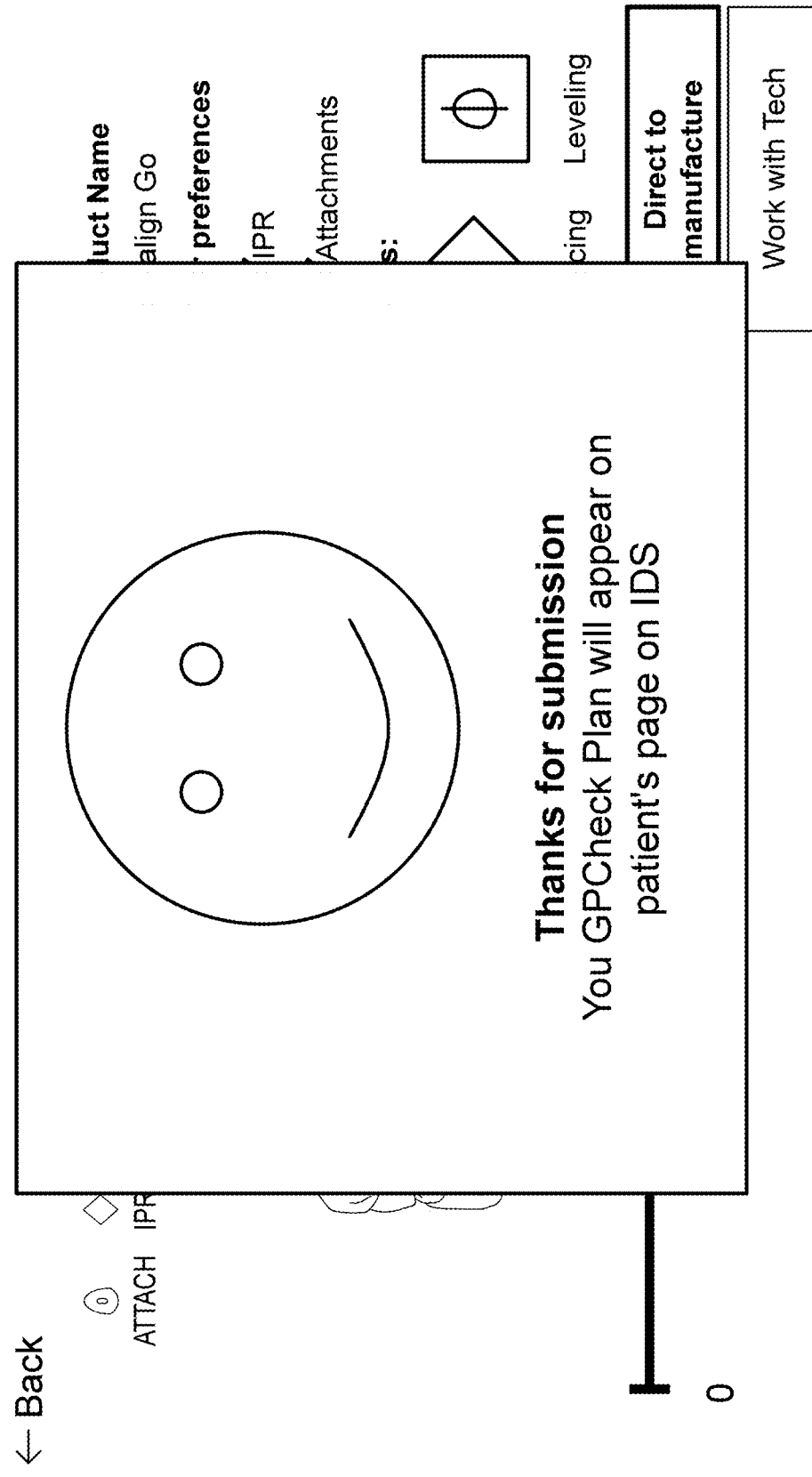
FIG. 10C is a user interface confirming submission of the modified treatment plan for recalculation of one or more treatment plans (which may be added to the array for further display, selection and/or modification).

FIGS. 10A-10C illustrate a user display screen including controls for displaying one treatment plan in detail, and/or for modifying the treatment plan. In FIG. 10A a treatment plan having 26 stages is shown. A display of the teeth at each stage is shown in the middle of the screen and this display may be changed by moving the slider (control 1005). One or more controls may also be used to change the view of the teeth shown 1007. Patient information may be shown 1009, as well as product information 1011. Treatment details and/or treatment preferences corresponding to the treatment plan being displayed may also be shown 1013. In FIG. 10A, the display indicates that the treatment plan was created allowing both interproximal reduction (IPR) and attachments. The exemplary display shown in FIG. 10A also indicates that this treatment plan resolves treatment concerns 1015; specifically this treatment plan resolves both upper and lower crowding and open bite. In addition, the display also includes a control allowing this treatment plan to be added to a subset of plans for consultation and/or for selecting this plan to order 1019. A display such as the one shown in FIG. 10A may be selected from any other display of the treatment plans, such as shown in FIGS. 7A-9B.

FIG. 10B shows the display of FIG. 10A in which the treatment plan is being modified by the user. In this example the treatment plan is being modified to adjust interproximal spacing 1021, shown by the + symbols on the teeth. In addition, the amount of leveling may also be adjusted. Additional modifications, and tools to control them, may also be included. Other controls on the screen may allow the user to communicate directly with a technician 1025, or to order a series of aligners based on this treatment plan 1027, and/or to enter into the consultation mode 1031. For example, selection of the control to order the plan may result in a confirmation screen, such as shown in FIG. 10C.

Figure 11B:
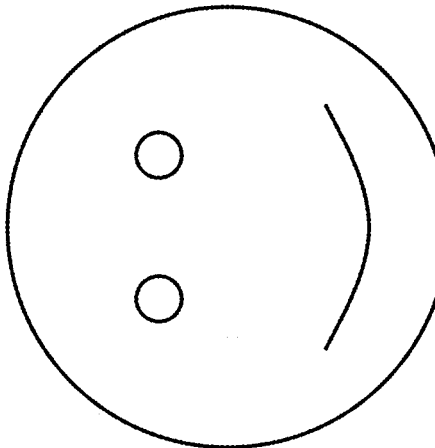
FIG. 11B is a user interface confirming submission of the modified treatment plan for recalculation of one or more treatment plans (which may be added to the array for further display, selection and/or modification).

FIG. 11A shows the exemplary screen of FIG. 10A, configured for communication with the technician, as mentioned above. In this example, the user may add instructions or preferences to annotate the treatment plan for modification. These text notes/instructions may be typed in by the user, or they may be selected from a menu of notes. In FIG. 11A, the instructions/notes 1105 include treatment preferences stating: "do not move upper and lower $3^{rd}$ molars" and "do not retract upper teeth." Additional comments may allow the user to submit 1107 or discard 1109 the comments. When the treatment preferences are submitted, the apparatus may indicate a confirmation screen 1111 as shown in FIG. 11B.

Figure 12:
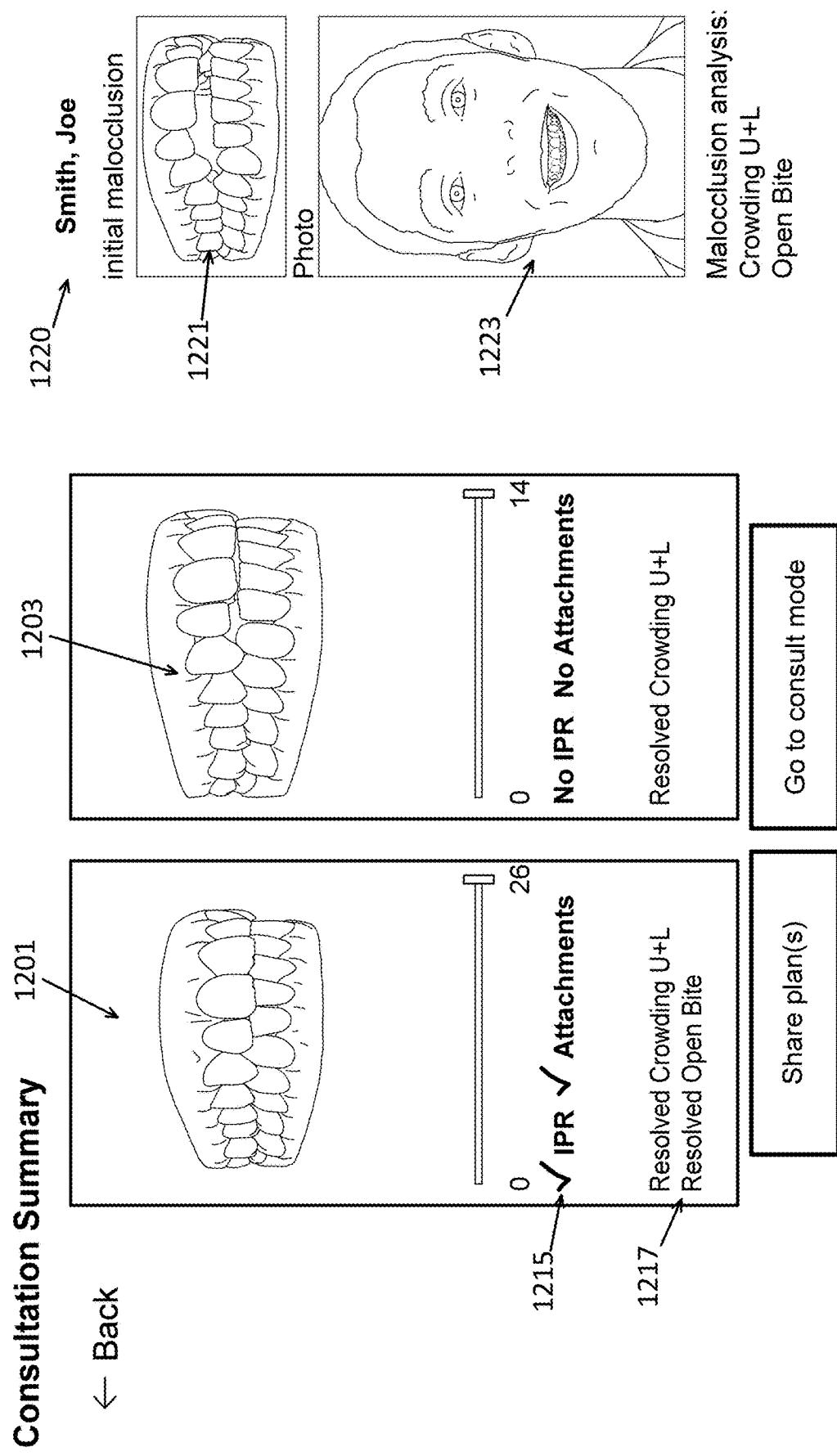
FIG. 12 is an example of a user interface configured as a consultation summary screen for use in a consultation mode to display a subset of the treatment plans to a subject (e.g., patient) to allow them to select between treatment options.

As mentioned above, the methods and apparatuses (e.g., software, firmware, hardware or some combination of these) may be configured to include a consultation mode. FIG. 12 illustrates one example of a consultation summary screen. This screen may be used by the user before entering into a consultation mode, or it may be used as part of the consultation mode. In general, the consultation mode may display a subset of the array of treatment plans; the treatment plans included in the subset may be selected by the user, or in some variations may be automatically selected based, e.g., on known user preferences. These selected treatment plans may then be presented, using the consultation mode, to the subject. In FIG. 12, the consultation summary screen shows two treatment plans 1201, 1203 as both images of the teeth (at the selected stage of treatment to be shown) and treatment details or treatment preferences 1215 (e.g., allowing/not allowing IPR, allowing/not allowing attachments, etc.). The display may also show the treatment concerns that are addressed by each treatment plan 1217 (e.g., resolved upper and lower crowding, resolved open bite, etc.). This may allow direct, including side-by-side, comparison by the patient. The screen in FIG. 12 also illustrates the patient information, including name 1220 ("Joe Smith"), the initial positions of the teeth 1221, an image of the patient 1223, and an analysis of the initial malocclusion(s) 1225. Controls on the display may allow the user to enter a consolation mode, in which a simplified display of the treatment plans may corresponding to various treatments may be shown to the patient.

FIG. 13, shows a "consultation mode" display screen, for display to a patient based on the subset of treatment plans selected by the user. In FIG. 13, the consultation mode screen shows two selected treatment plans 1303, 1305, for comparison with the patient's current dentition 1301. The first treatment plan is a 26 stage plan 1303, while the second treatment plan is a 14 stage treatment plan in this example. Any subset of treatment plans may be shown. In this example, the various treatment plans are shown with annotation indicating how well they address the patient's identified malocclusions 1307. For example, the 26 stage treatment plan (which may correspond to a first product) resolves both the upper and lower crowding and the open bite 1309. The 14 stage treatment plan (which may correspond to a second product) resolves the upper and lower crowding, and partially resolves the open bite 1312.

From the consultation mode, the user and/or the patient may review, in a sequential or side-by-side display, the various selected treatment plans, and may select between them. The consultation mode may also include information about the cost and/or timing of the treatment plans (including the number of stages, etc.).

FIG. 14 is an example of a display for showing detail (including animation) for a particular treatment plan. Individual stages may be selected.

Figure 15:
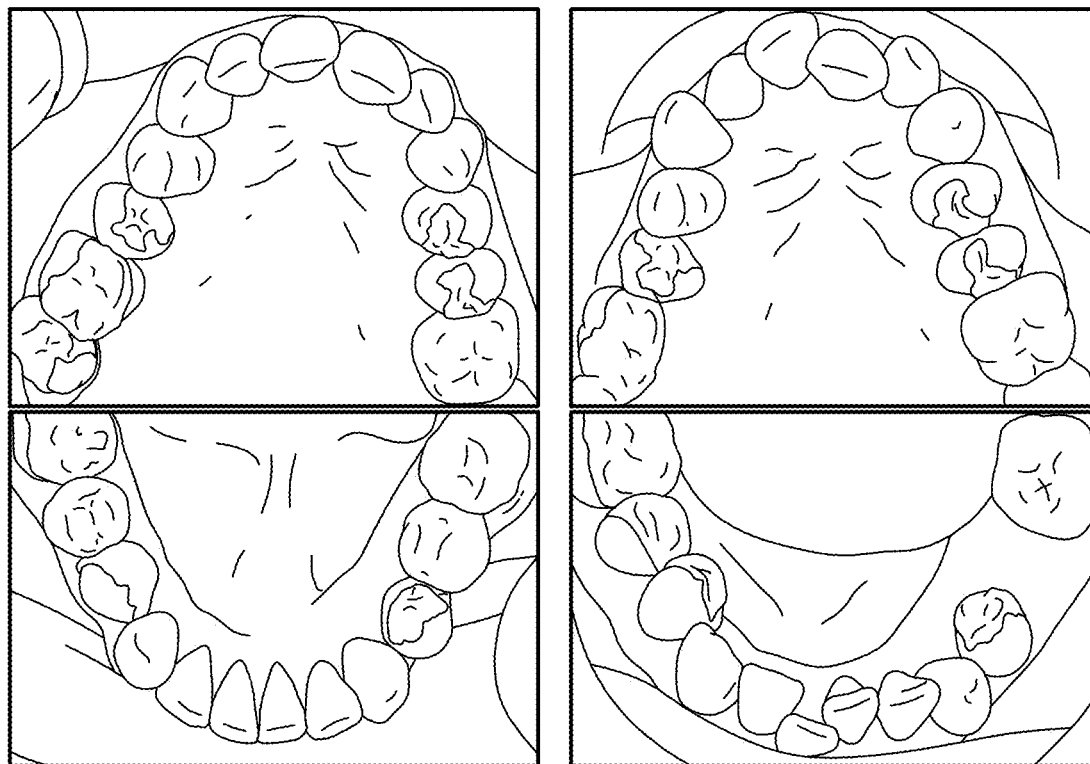
FIG. 15 illustrates a display showing progression of a patient's malocclusion over time (from 2005 to 2011). The user interface may allow the user to select and display image form the patient's dental record in addition to one or more treatment plans from the array of treatment plans.

In general, patient information, including dental record information, may be shown as well. For example, as a reference, the methods and apparatuses may include a display of the patient's upper and lower arches (e.g., see FIG. 15). In FIG. 15, the display shows images of the upper and lower jaw at two times (e.g., 2005 and 2011) for the patient. This type of display shows the progression of the malocclusion over time. In FIG. 15, the malocclusion includes a slipped contact and mesial drift.

As mentioned above, the array of treatment plans may typically include three or more (more preferably 12 or greater) treatment plans. FIGS. 16A-16M illustrate one example of an array of treatment plans for a patient. FIG. 12A shows an example of the patient's actual dentition, shown as a digital model. As discussed above, this model may be generated from a direct digital scan of the patient's teeth, or from an impression. FIGS. 16B-16M illustrate 12 alternative treatment plans generated for the patient and combined into an array of treatment plans that the user may select from or modify further. FIGS. 16B-16M are arranged as a grid, for convenience, and a model of the final tooth positions, following completion of the treatment plans, is shown. The actual treatment plan may include an indicator of position and/or orientation of each tooth, as well as key frames describing how to translate from the initial position (e.g., FIG. 16A) to a final position (FIGS. 16B-16M). In FIGS. 16B-16D, shown as the horizontal axis, each of the three treatment plans is shown having been calculated with the treatment details or treatment preferences set to not allow attachments and not allow IPR. The figures also show the use of 26, 15 or 7 stages, respectively for FIGS. 16B-16D. FIGS. 16E-16G show a series of treatment plans (again 26, 15 or 7 stages, respectively) for which the attachments were allowed, but not IPR. FIGS. 16H, 16I, and 16J (26, 15 or 7 stages, respectively), show examples of the final stages of treatment plans in which attachments were not allowed, but IPR was allowed. Finally, FIGS. 16K, 16L, and 16M (26, 15 or 7 stages, respectively), show examples in which the treatment plans were generated allowing both attachments and IPR.

An alternative treatment plan display and modification screen is shown in FIG. 17. In this example, the treatment plan is a 26 stage plan. The initial display is the 26 stage device which did not allow either IPR or attachments. In FIG. 17, the right half of the screen shows controls, configured as filters that may be selected to toggle between the different treatment plans. Because the treatment plans are all pre-calculated and included it the array of treatment plans, they may be easily and quickly toggled between each other, even in very large or complex treatment plans. FIG. 17 shows controls that allow the display to switch between a treatment plan allowing IPR/not allowing IPR 1703, and treatment plans that allow or do not allow attachments 1705. Additional other controls may allow the user to toggle between different products having different treatment durations (stages) 1707. In FIG. 17, the apparatus may also allow the user to select different treatment details 1709.

Treatment Plan Optimizing Generator

Also described herein are the methods and apparatuses for automatically creating a treatment plan to align a patient's teeth using a plurality of removable aligners to be worn in sequential stages. These methods and apparatuses may include creating a plurality of variations of treatment plans to align a patient's teeth using a plurality of removable aligners to be worn in sequential stages. The method may be referred to herein as a method for automatically generating optimized treatment plans, and the apparatus (e.g., software, including non-transient, computer-readable medium containing program instructions for creating a treatment plan to align a patient's teeth using a plurality of removable aligners) may be referred to as a treatment plan optimizing generator.

The methods for automatically generating optimized treatment plans described herein may simultaneously optimize final position and intermediate teeth positions (e.g., staging). This may allow the apparatus to produce treatment plans having a final position that is achievable in exactly the allowed number of stages (and therefore duration of treatment) for a product corresponding to a set number (or range) of aligners.

The comprehensive treatment plans built using the methods of automatically generating optimized treatment plans described herein also incorporate an optimized or idealized treatment plan (which is referred to herein as a comprehensive treatment plan) generated without consideration of the amount of time or number of stages it may take to achieve. This may enable the method to improve orthodontic measurements that are not explicitly defined as optimization goals. Measurements that represent potential orthodontic problems may be restricted to a range between the initial positions (or values) of the patient's teeth and the positions (or values) planned in the comprehensive treatment. This ensures that partial final position does not introduce or worsen orthodontic problems unnecessarily.

Figure 18:
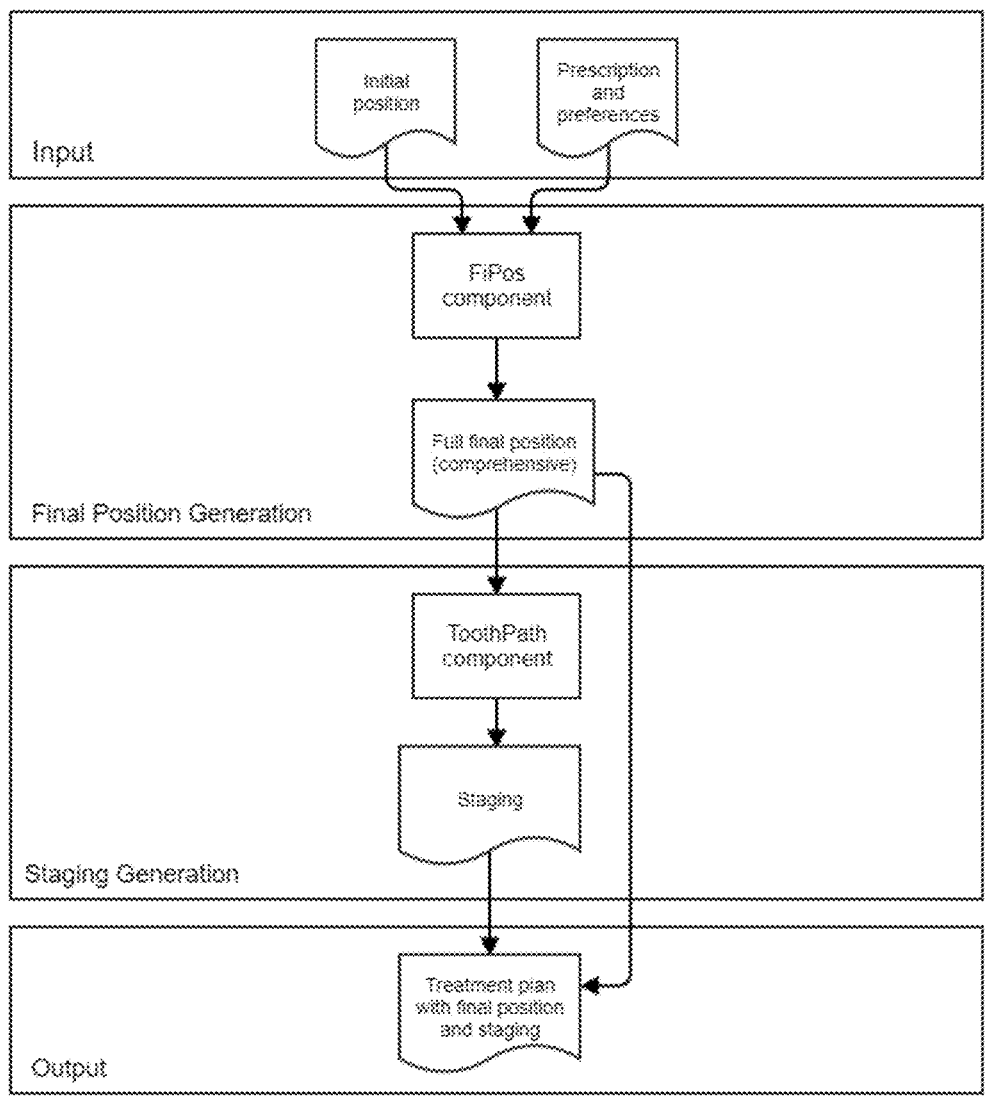
FIG. 18 illustrates a sequence of a linear treatment planning method using a comprehensive final position as the final position of the planned treatment.

As an alternative to the methods and apparatuses described herein, a treatment plan may be created by first building (manually or automatically or a combination of manually and automatically) the comprehensive treatment plan, and then segmenting the plan into a series of movement-limited stages. In this method, the number of stages depends upon the final positions of the teeth. Stages are determined by, e.g., iteratively simplifying the leading tooth movements. FIG. 18 shows one example of a process flow for this method, in which the initial position of the teeth is provided along with the user (e.g., dental professional's) prescription and preferences as inputs to generate the final portion of the teeth (e.g., the comprehensive treatment plan). The final position produced by this method may not always satisfy product constraints due to inaccuracy of treatment length estimation. Further, straight-forward simplification of tooth movements that may be required to segment the steps of the plan may unnecessarily compromises quality of the final position. Finally, treatment plan may not prioritize aesthetic goals over orthodontic norms and rules, achieving sub-optimal resolution of the likely patient's chief concerns. Although these problems may be mitigated by personal judgement of technicians, such manual adjustments may take significant time and the produced plans may lack consistent quality.

The method in FIG. 18, which involves sequentially solving for a comprehensive final position ("final position generation"), then segmenting this into a series of aligners ("staging generation") and finally outputting the treatment plan including both the final position and staging ("output") is a linear process, although it may include iteration to adjust the final position and/or staging. As mentioned above, there are often situation in which it is desirable to pan a treatment in which the parameters such as the length of treatment are constrained. Further, it would be beneficial to provide methods and apparatuses for treatment planning in which the entire treatment plan (e.g., each stage) is determined at the same time, rather than sequentially.

Described herein are methods and apparatuses for generating orthodontic treatment plans by expressing the target treatment goals for tooth movement as numerical expressions and limiting these target treatment goals by numeric constraints corresponding to limits on the treatment. Once the treatment goals and limitations are defined numerically, the resulting numeric expression (e.g., equations) may be treated as a non-linear optimization problem and solved to generate an optimal treatment plan given the constraints and target goals. These method may result in generating treatment plans that may be referred to as "partial plans" because they are not intended to fully resolve all of the patient's clinical orthodontic conditions, but may best resolve them within the given product limits (e.g., within a limited treatment time/number of stages, etc.).

Figure 19:
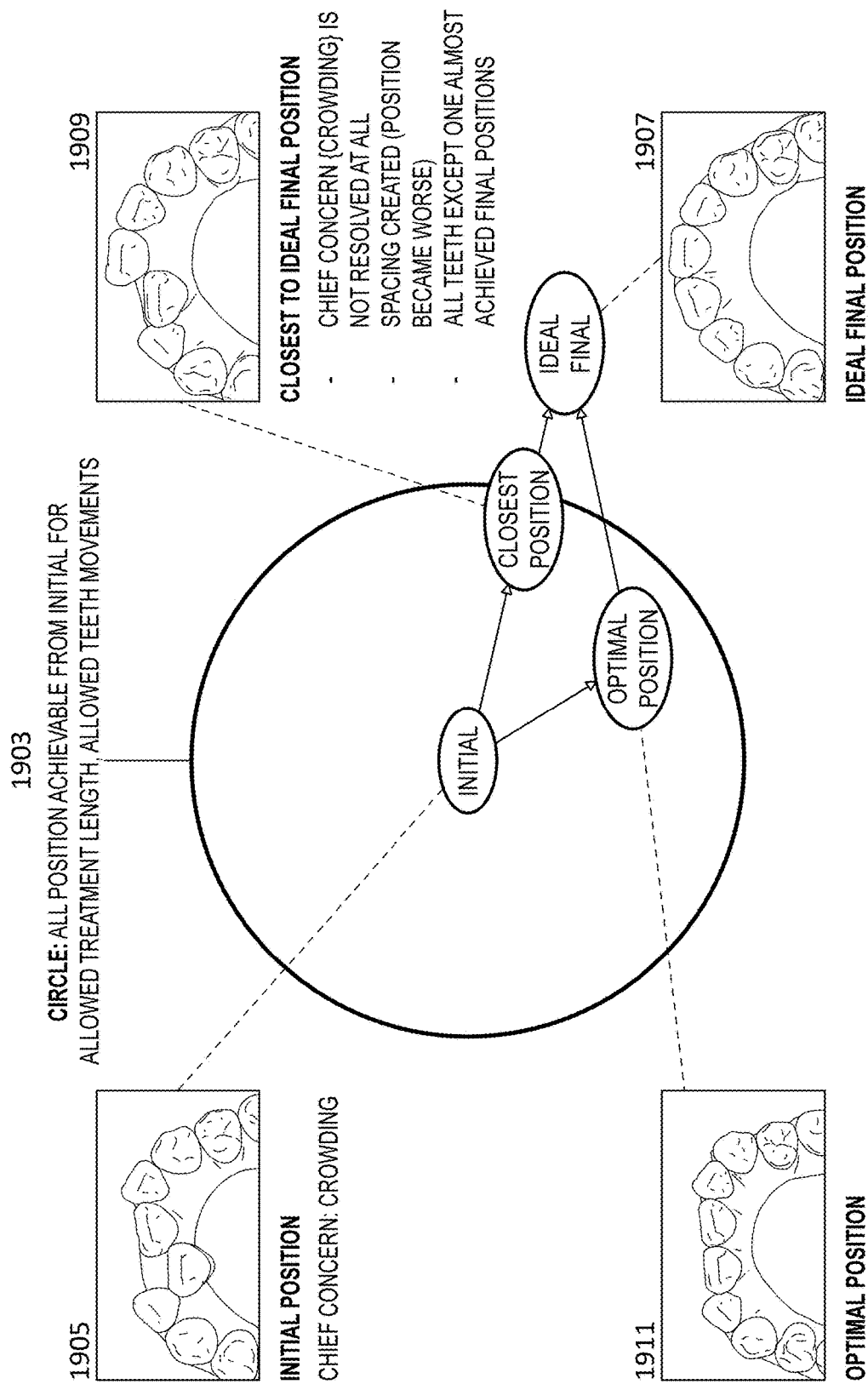
FIG. 19 is a graphically illustration of a method for automatically generating optimized treatment plans described herein.

FIG. 19 schematically illustrates a simplified overview of the concept underlying the method for automatically generating optimized treatment plans described herein. In FIG. 19, the region within the circle 1903 represents all of the treatment plans and final positions that may be achieved from a patient's starting tooth configuration (shown as the central circle 1905, in the upper left). The circle therefore contains all of the final tooth positions and treatment plans for achieving these final positions when the treatment plan is constrained by the limits of the aligner system (e.g., the limits on the number of stages, the limits on the amount and rate of movement of each tooth, etc.) and the limits required by the dental professional (e.g., restricting movement of some teeth, etc.). These limits may be referred to as the treatment preferences and the treatment details. The circle shown in FIG. 19 is highly simplified; the space bounded by the constraints may be multi-dimensional, but the principle concept is the same as shown in FIG. 19.

A comprehensive treatment plan is typically determined without concern for all or most of the constraints forming the boundary 1903. Thus, in FIG. 19, the comprehensive treatment plan ("ideal final") 1907 is shown located outside of the space formed by the boundary 1903, although in theory it may be inside or outside. An image of the final tooth position corresponding to the comprehensive treatment plan is shown in the bottom right of FIG. 19. Since this orthodontically ideal final position may not be achievable within the boundary, the space contained within the boundary must be examined to identify the next-best treatment plan that satisfies as many of the treatment concerns while providing an aesthetically pleasing result.

One possible solution may be to find the treatment plan within the boundary that is close to the ideal final position. In FIG. 19, the closest position 1909 results in a final position of the teeth that is unsatisfactory. As shown in the upper right corner of FIG. 19, the treatment plan that is closest to the ideal final position within the boundary is does not resolve the principle concern (e.g., crowding) though it may address other concerns (e.g., leveling, etc.), and instead creates or makes worse other problems, such as spacing of the teeth. Although almost all of the teeth, except one, achieved a final position nearly identical to the ideal final position, the resulting final position is both orthodontically and aesthetically unsatisfactory.

Instead, the optimal position 1911 that both resolves the principle concern (e.g., crowding of the teeth) and results in an aesthetically pleasing result is shown in the bottom left of FIG. 19. Although fewer teeth achieved the final position that is the same as the optimal position, the resulting final position is superior to the closest position shown.

Figure 20A:
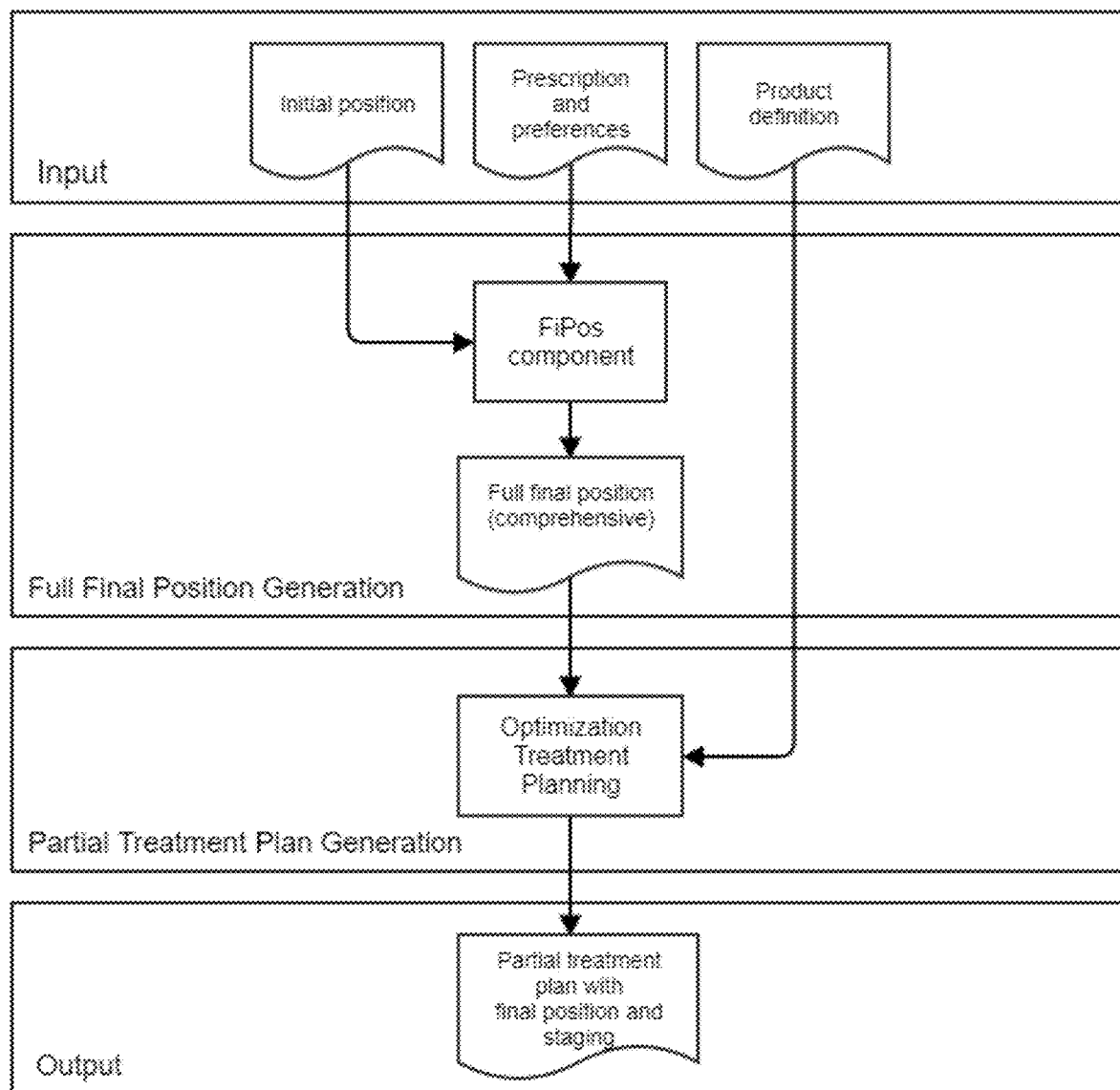
FIG. 20A illustrates a sequence of an optimization-based partial treatment planning method (e.g., an automated method of creating a treatment plan to align a patient's teeth using a plurality of removable aligners to be worn in sequential stages) as described herein.

In practice, the ideal fit may be found by expressing the constraints as a numeric expressions and a set of limits on these numeric expression and solving the resulting expression as an optimization problem. Specifically, the method may include identifying, for a particular patient, a set of treatment preferences and treatment details, expressing these treatment preferences and treatment constrains as a nonlinear expression, and solving the optimization problem. FIG. 20A illustrate a schematic of this method. In FIG. 20A, the input into the method (or an apparatus performing the method) is the initial position of the patient's teeth, the dental professional's prescription and preferences, and the definition of the product. The definition of the product may be thought of as the set of treatment preferences. This may include, for example, the number of stages, the properties of the aligners including the rate of movement of the teeth by the aligner, etc. The user's prescription and preferences may correspond to the treatment details.

In any of the methods and apparatuses described herein, it may be beneficial to have an ideal tooth position (e.g., the comprehensive final tooth position) for use in the treatment planning. However, it should be clear that this comprehensive final tooth position is not used as the actual final tooth position. Instead, the methods described herein concurrently determine both the actual final tooth position and the stages required to achieve that tooth position within the limits required by the treatment preferences and treatment details. Software for determining a comprehensive final position may be used (which may also be referred to as "FiPos" software) or the final position may be manually, or semi-manually/semi-automatically determined either digitally or manually (e.g., using a model of the patient's teeth) and digitized.

Once a comprehensive final tooth position has been identified ("Full Final Position Generation"), this final position may be used, along with the initial position, treatment preferences and treatment details, to determine the optimal treatment plan, using "optimization treatment planning." This optimized treatment planning is described in greater detail below. The optimization treatment planning may include result in a vector description including the staging, key frames (showing movement of the teeth between stages) and a proposed final position of the teeth, which may be output ("output") by the system.

Figure 20B:
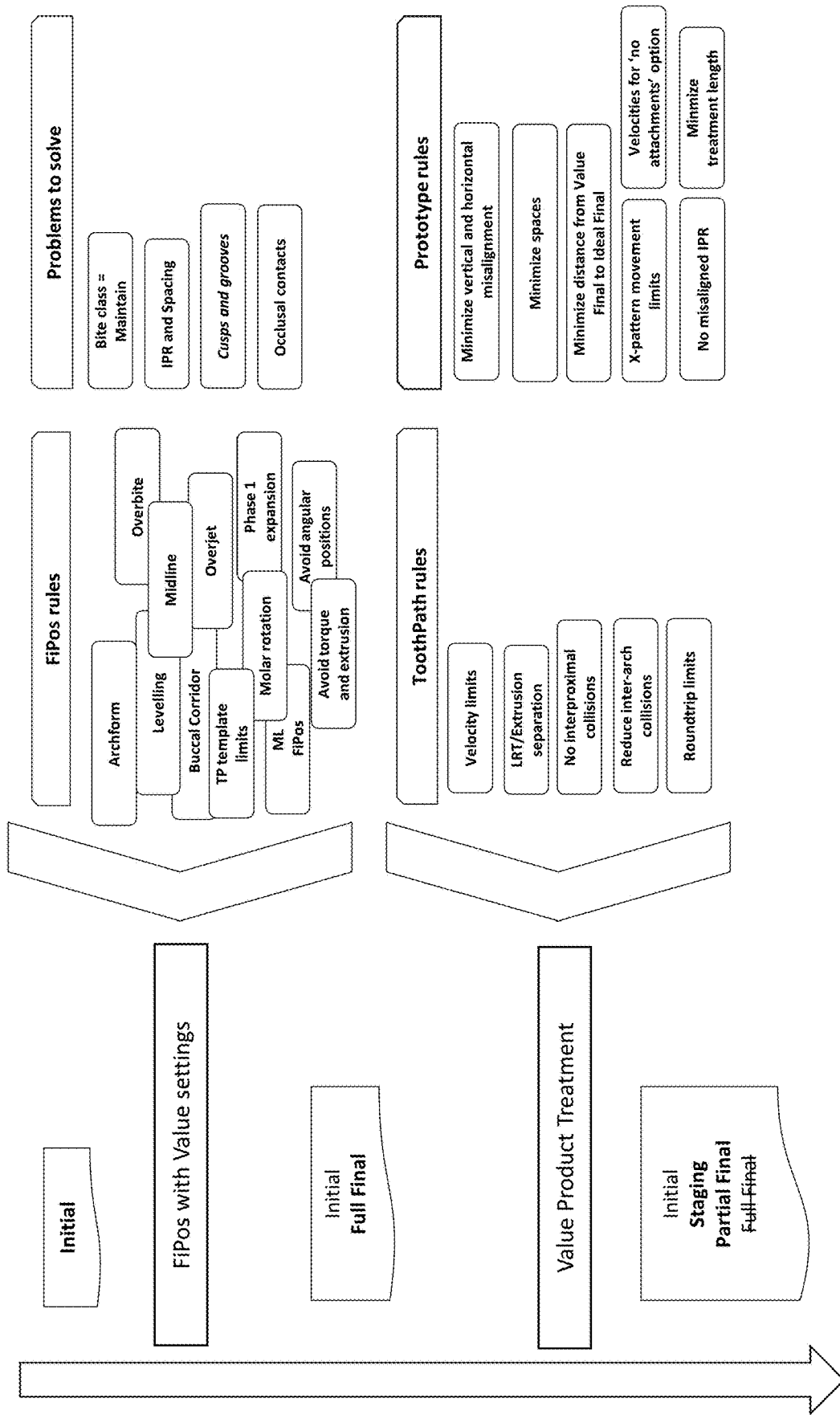
FIG. 20B is another schematic illustration of a method of creating a treatment plan to align a patient's teeth using a plurality of removable aligners to be worn in sequential stages.

FIG. 20B illustrates this method is slightly more detail, showing the rules and problems to be solved for the determination of the comprehensive final position, as well as an example of the rules and limitations for determining an optimization problem that can be solved for an optimized treatment plan.

Figure 20C:
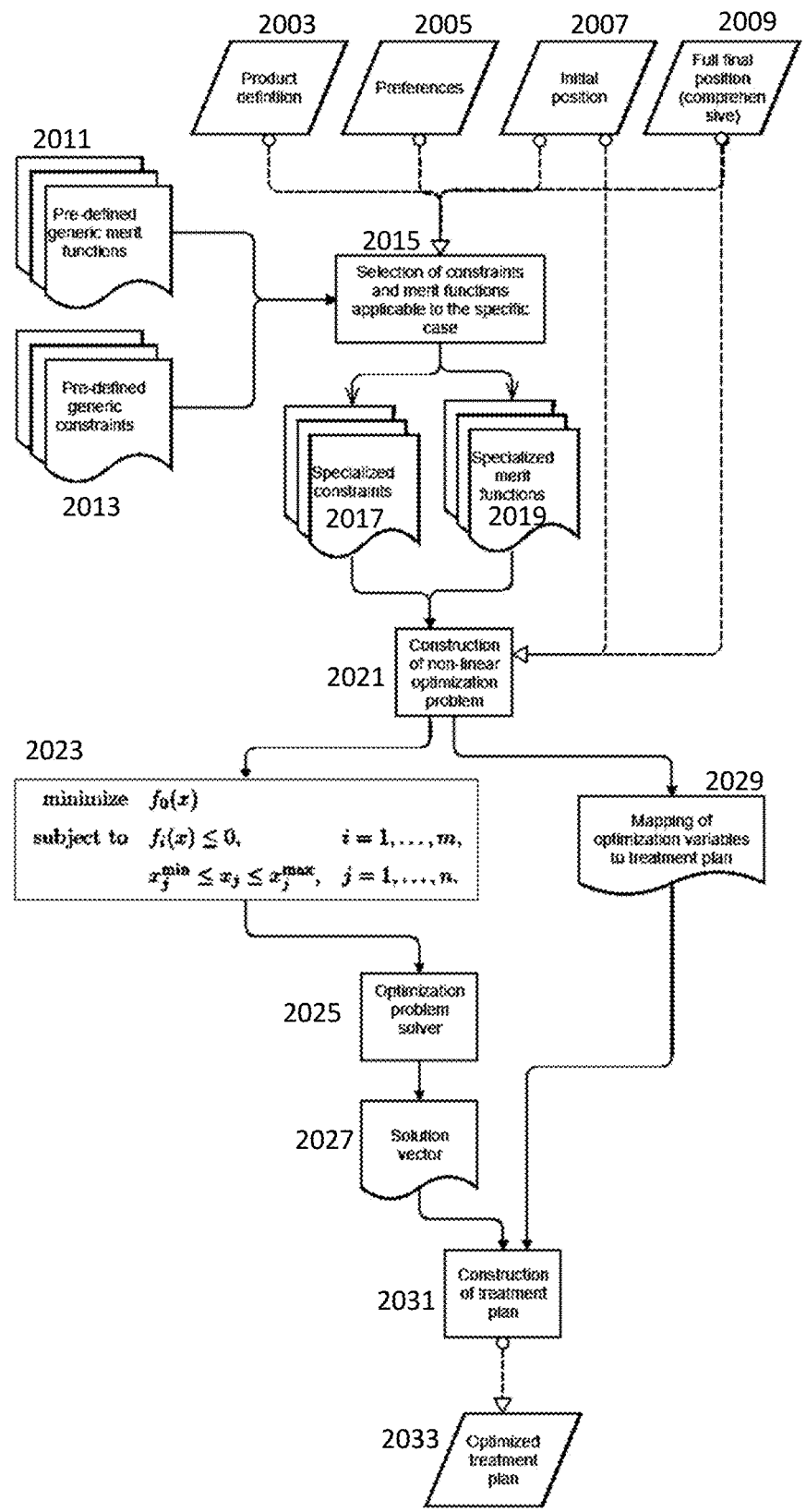
FIG. 20C is an alternative illustration of a method of creating a treatment plan to align a patient's teeth using a plurality of removable aligners to be worn in sequential stages.

In FIG. 20C, the same four inputs (product definition/treatment details 2003, preferences (treatment preferences, user-specific and/or patient specific) 2005, initial tooth position 2007, and comprehensive tooth position 2009) are used by the treatment plan optimizing generator to select a plurality of numerically expressed treatment targets from a memory accessible to the processor 2011. The memory may generally include a set of pre-defined generic expression ("merit functions" or merit function components, or "target functions") that describe the numerically expressed treatment targets. Typically each of these targets is a numeric function that has a value that is closest to zero for ideal cases. For example, as will be described below, if the treatment target is alignment in an x direction, the numeric function may express the deviation from alignment in the x direction as a numeric vale (e.g., from 0, meaning in alignment, to some distance, e.g., in mm, out of alignment).

Similarly, the treatment preferences may be expressed as limits on the target functions. The treatment preferences, and in some variations treatment details, initial positions and comprehensive positions may be used to select the numeric limits from a stored set of pre-defined generic constraints. Once the numeric limits and target functions have been selected (e.g., based on the set of treatment details, the set of treatment preferences and the comprehensive final position of the patient's teeth) 2015, resulting in the specialized constraints (limits) 2017 and specialized numerically expressed treatment targets (target functions) 2019, they may be expressed as a non-linear optimization problem 2021 by first combining the plurality of numerically expressed treatment targets (target functions) to form a single numerical function (single numerical merit function). Each numerically expressed treatment target may be multiplied by a scaling factor. The resulting non-linear optimization problem is a single numerical function subject to the plurality of numeric limits 2023.

Thereafter, the optimization problem may be solved using conventional techniques, such as an interior point method. Such nonlinear constrained optimization solution techniques 2025 may minimize the single numerical function subject to the plurality of numeric limits to get a solution vector including all stages forming the treatment plan 2027. The solution vector may be mapped to a treatment plan 2029, wherein this "optimized" treatment plan 2033 includes a final tooth position that is different from the comprehensive final position of the patient's teeth.

An optimized treatment plan may be identified by solving an optimization problem once the constraints on the patient's teeth (e.g., product definition/treatment details and treatment preferences) are expressed as numeric functions and limits. Non-linear constrained optimization problems can be represented by a merit function and a set of inequality constraints:

$$\begin{aligned} \text{minimize} \quad & f_0(x) \\ \text{subject to} \quad & f_i(x) \le 0, \quad i = 1, \ldots, m, \\ & x_j^{min} \le x_j \le x_j^{max}, \quad j = 1, \ldots, n. \end{aligned}$$

Figure 21:
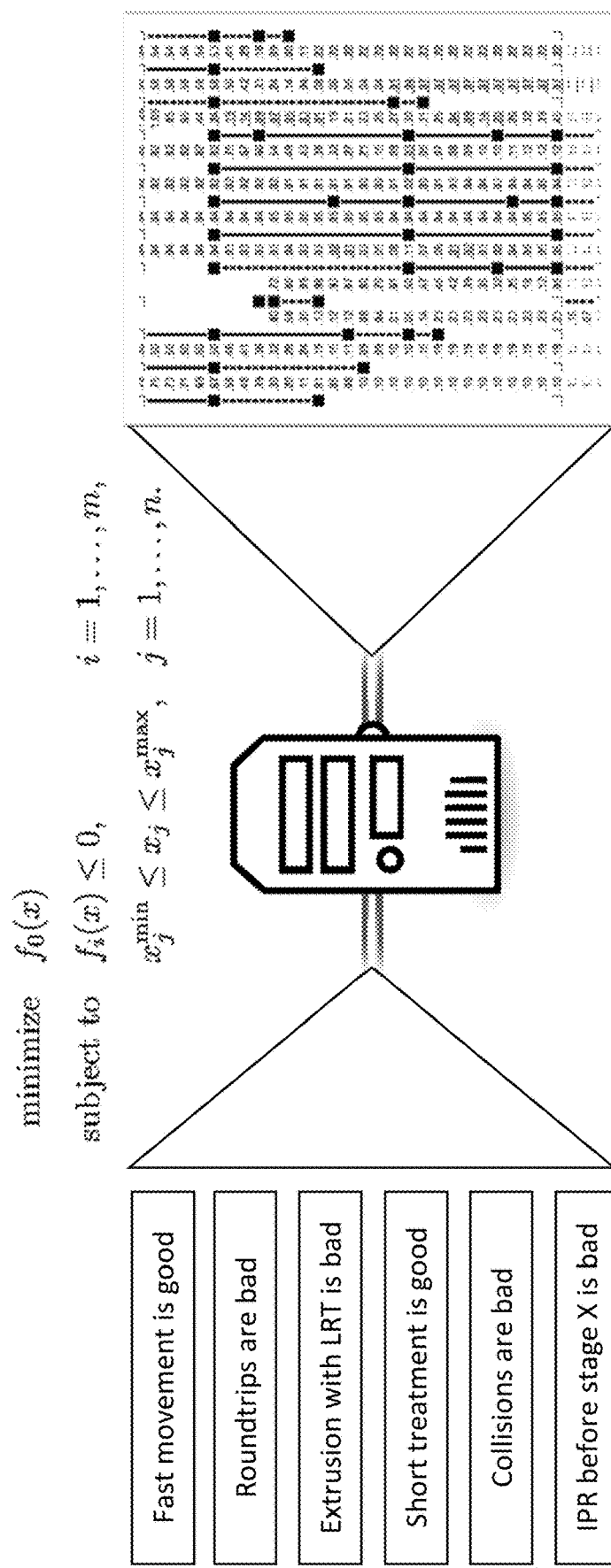
FIG. 21 illustrates the use of a non-linear constrained optimization method to generate a treatment plan.

See, e.g., FIG. 21. To produce treatment plan by solving optimization problem, the treatment plan is described in terms of distinct values, which are mapped to $x_j$ variables in the problem statement. One possible mapping, used in the first implementation of the method, is described below. The position of each tooth at the final stage is described in terms of six coordinates (orientation, e.g., rotation, and translation from the center of the jaw) and mapped to six variables. Staging, i.e. intermediate positions, of each tooth is described as a linear combination of several functional component. Each component describes deviation from linear movement at a certain stage and is parametrized by six coordinate deviations and a stage number. Thus, each functional component is mapped to seven variables in optimization space, per tooth.

The numeric limits on the single numerical function are understood to be qualities of treatment plan that must never be violated and may be defined as inequality constraints Constraints enforce mechanical, biomechanical, clinical and aesthetic rules, as well limits imposed by product definitions. Implemented constraints include, but are not limited to, amount of reproximation, maximum velocity of tooth movement, depth of inter-arch collisions, cusp-to-groove occlusion. Example of constrains also include "do-no-harm" constrains that ensure that the movement of the teeth does not result in making the alignment worse or overcorrecting, e.g.: midline, overjet, overbite, occlusion, misalignment, spaces, rotations, etc. Other constraints may include: amount of collisions, movement velocities and separation of movements, etc.

Qualities of treatment plan that must be improved as much as possible within constraints are defined as numerically expressed treatment targets, i.e. components of merit function, $f_0$. Targets are typically features that are to be improved or modified by the treatment. Targets may include, but are not limited to, length of the resulting treatment, amount of spaces, misalignment between teeth, etc. For example, potential chief concerns may include: misalignment (x and z), de-rotation, occlusion, diastema and spaces, inter-arch collisions, etc. Other targets may include: closeness to comprehensive setup, and roundtrips. The merit function(s) are defined as a non-linear combination of target functions, weighted by pre-defined coefficients. All of the target functions may be summed (and weighted) to form a single numerical function (single numerical merit function).

For example, target functions that may be weighted, summed and minimized as described herein may include: minimal difference with ideal final position (with the target of trying to achieve an ideal final position); misalignment, e.g., by minimizing the difference between x- and z-misalignment in value final position and in ideal one; tooth aligned to arch (e.g., minimize the angle between the x axis in a value final position and an ideal one); minimal diastema (e.g., minimize spaces between neighboring teeth); occlusion (e.g., applicable for cases with both jaws, pull corresponding cusps from one jaw to the groves from opposite jaw); round-trip (e.g., minimize mesial-distal and buccal lingual round-trips); inter-arch collisions in value position (applicable only for cases with both jaws, e.g., try to create inter-arch collision at posterior teeth as close to ideal final position as possible); inter-arch collisions during staging, etc.

In general, measurement may be a function implemented in software that can be used as target or constraint in the optimization problem. The input for every measurement may be: 3D models of all teeth (constants), six coordinates per tooth that define the tooth position relative to the jaw. The output of every measurement may be a single numerical value, such as distance in mm, angle in radians, or score from 0 to 5.

Figure 22A:
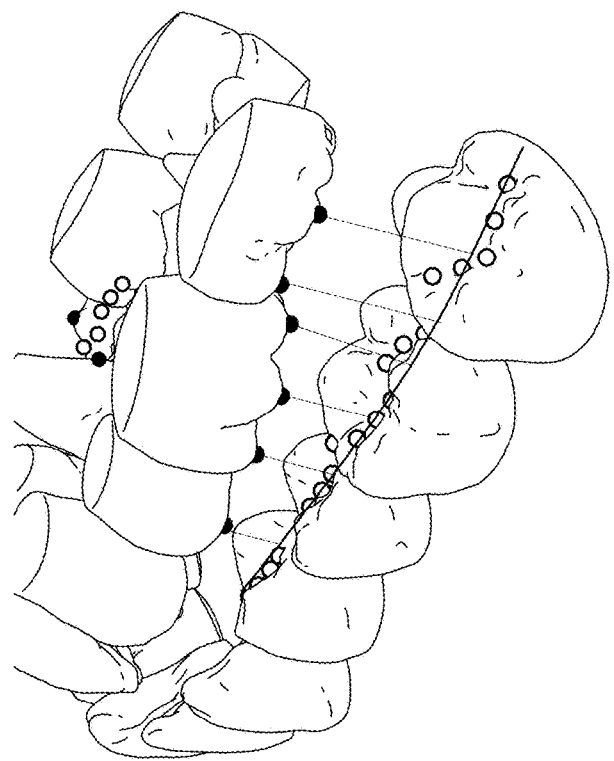
FIG. 22A illustrates one method of quantifying occlusion between upper and lower jaw so that it may be expressed as a numeric expression.
Figure 22D:
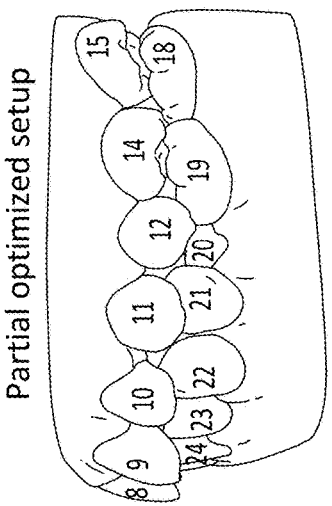
FIGS. 22B-22D show patient cross bite correction from a starting position (FIG. 22A) using a full treatment plan (FIG. 22C), and partial, optimized treatment plan (FIG. 22D).
Figure 22C:
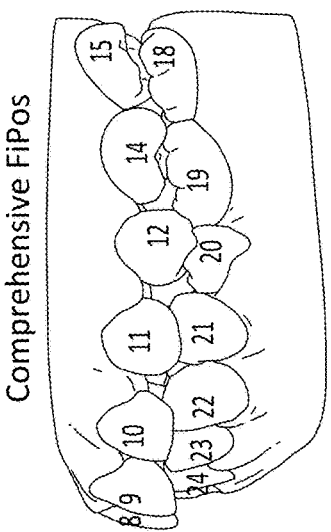
Figure 22B:
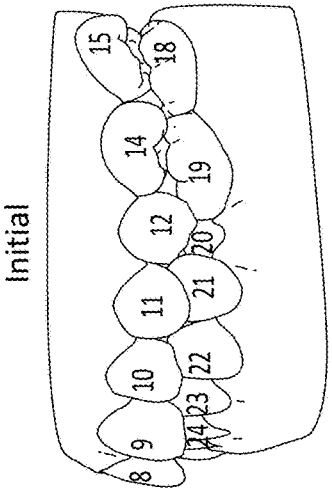

Examples of targets are shown in FIGS. 22A-25 illustrate examples of targets and constrains that are expressed as numeric functions and limits. For example, FIG. 22A shows one method of quantifying occlusion (e.g., between upper and lower jaws). In FIG. 22A, the occlusion metric is the cumulative distance between all corresponding cusp points from one jaw and groove spline from opposite jaw. For the upper jaw, lingual cusps are used and for the lower jaw, buccal cusps are used. Thus, the quality of the occlusion is measured as a function of distances between occluding grooves and cusps. The constraints of the optimization problem may ensure that quality of occlusion in partial setup is not worse than the patient's initial position. As a result, if the patient's cross bite cannot be fully fixed with good occlusion in low-stage product, it will not be corrected. This is illustrated in FIGS. 22B-22D. FIG. 22B shows a view of a patient's initial tooth configuration (cross bite). FIG. 22C shows the correction using a comprehensive final position to correct. FIG. 22D shows a comparable correction using a 'partial' optimization setup as described herein.

Figure 23:
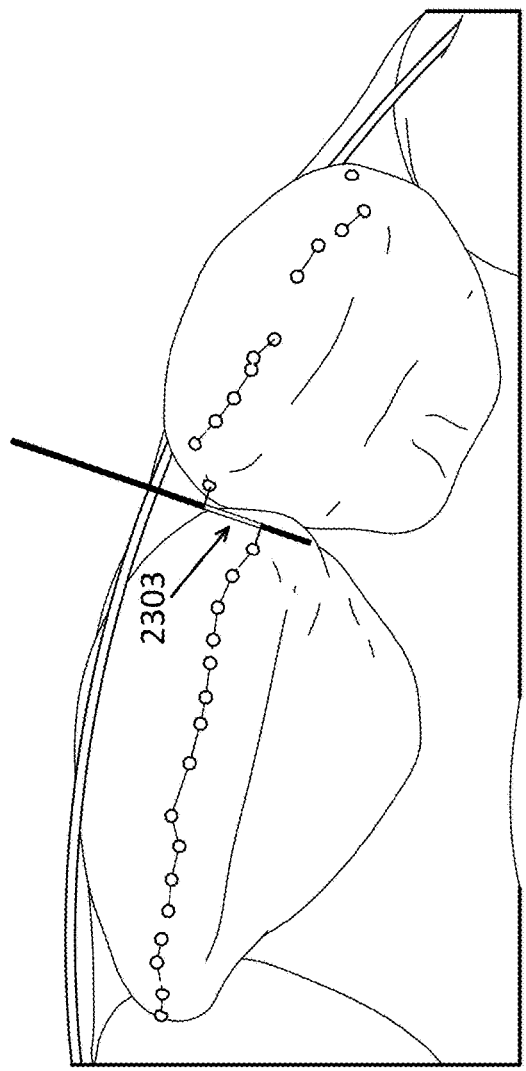
FIG. 23 shows quantification of x-misalignment so that it may be expressed as a numeric expression.
Figure 24:
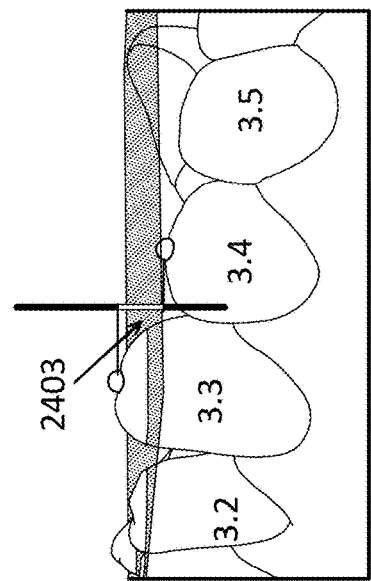
FIG. 24 illustrates quantification of z-misalignment so that it may be expressed as a numeric expression.

FIG. 23 shows an example of the quantification of x-misalignment. X-misalignment is a projection of a line between buccal ridge end points of two neighbor teeth onto the arch normal in a given stage 2303 (yellow line). Similarly, FIG. 24 illustrates quantification of z-misalignment. Z-Misalignment is a projection of a difference of tooth tip point onto the jaw occlusal plane's normal in a given stage 2403.

Figure 25:
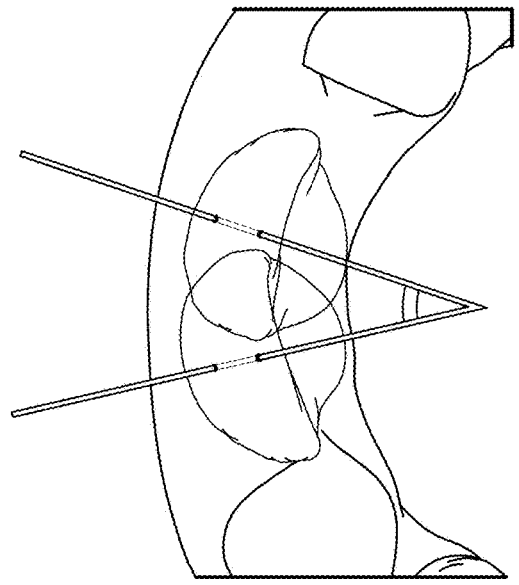
FIG. 25 shows alignment to arch quantification so that it may be expressed as a numeric expression.

FIG. 25 illustrates alignment to arch quantification. As illustrated, alignment to arch for a given tooth is the angle between a projection of X axis in a value final position and an ideal one.

Examples of constraints include tooth movement limits that typically require that the range of movements that are allowed are limited for every dental type according the product definition. These limits may be defined clinically to ensure that the proposed treatment plans are achievable in practice with the device to be used. Each product (e.g., aligner) may different set of values, which may be stored in a look-up table or other memory accessible by the processor.

Tooth movement limits may include rotation (e.g., tooth rotation along z axis); tip (e.g., tooth rotation along x axis), torque (e.g., tooth rotation along y axis); crown movement, including horizontal crown movement (e.g., translation along z axis ignored), buccal-lingual crown movement (crown center translation along x axis), mesial-distal crown movement (e.g., crown center translation along y axis); mesial-distal root apex movement (e.g., root apex translation along y axis); buccal-lingual root apex movement (e.g., root apex translation along x axis); extrusion/intrusion (e.g., tooth translation along z axis); and relative extrusion.

Collision constraints may also be used to limit collisions between teeth. Further, staging constraints may be applied to intermediate stages (e.g., key frames) to ensure that the treatment is plan is consistent and clinically predictable. Collision constraints may include inter arch collision (applicable only for cases with both jaws), which forbids deep collisions greater than, e.g., 0.05 mm in depth, on the posterior teeth and may forbid smaller or equal depth in anterior teeth in the value final position. Collision constrains may also forbid one arch collision (e.g., so that collision between neighbor teeth in value final position does not exceed a maximum of collisions in initial, ideal final or value corresponding to the tight contact).

Staging constraints may also be used. For example, stating constraints may include synchronized finish of value final positions (e.g., every tooth must complete movement at the same stage number); fixed stage constraints (e.g., every tooth starts movement at stage 0); "not greater stage" (e.g., the final stage number, treatment length, must not be greater than allowed in the product (i.e. 20 stages, etc.); a "do not trigger Stairs pattern" (e.g., do not exceed mesial-distal movements on every tooth that can be predictably achieved in practice without long sequential teeth movements, referred to as a stairs pattern); constraints so that no Z-rotation and Intrusion/Extrusion round-trips occur on any tooth; and velocity rules (e.g., tooth movement over a single stage, e.g., aligner, must not exceed 0.25 mm).

Other examples of constraints include "do no harm" constraints, which ensure that planned final position does not introduce or worsen orthodontic problems. In the optimized final position, the value of every measurement that corresponds to an orthodontic condition must lie within the value measured in initial position, and the value measured in the comprehensive (ideal) final position. For example, overjet may be limited (applicable only for cases with both jaws)

by requiring that each jaw should have at least one incisor for each side. Overbite may be limited (applicable only for cases with both jaws); each jaw should have at least one incisor for each side. Midline may be limited (applicable only for cases with both jaws); each jaw should have more than two anteriors. Occlusion may be limited (applicable only for cases with both jaws). X- and z-misalignment may be limited (applicable for each pair of neighbor teeth where at least one tooth is movable); arch and jaw occlusal plane may be calculated once in initial position. Spacing (applicable for each pair of neighbor teeth where at least one tooth is movable) may be limited; crown space between neighbor teeth should not exceed maximum of spaces in initial and ideal final positions. Angular may be limited by keeping teeth axes between initial and ideal final position (alignment to arch measurement for x, y and z axes).

Once the problem is stated in this manner it can be solved by any constrained optimization algorithm of sufficient power, such as an Interior Point method. The result is a solution vector. The vector will include position and orientation values for each tooth, as well as stage number corresponding to each tooth. The vector may describe a large number of such values, e.g., $x_j$ variables.

The produced solution vector of optimal values of $x_j$ variables may be converted to the treatment plan by the mapping of variables described above in reference to FIG. 20C.

In general, these methods may be used to generate partial treatment plans that are characterized by addressing patient's concerns as much as possible within the product limits. In contrast to comprehensive, or full, treatment plans that have as their end point the ideal, comprehensive tooth position, these partial treatment plans may not fully resolve all of the concerns of the dental professional, and may not address all orthodontic problems. To produce such partial plan, treatment length and tooth limits allowed within the product are implemented as inequality constraints. This forces the optimization algorithm to find a solution, i.e. treatment plan, within the product limits, that improves merit function as much as possible, but not to the full degree.

In general, to improve quality of the plans, an optimization target (e.g., the comprehensive tooth position) may be added to minimize distance between the partial plan and the comprehensive treatment. This distance can be measured by a length of secondary treatment that achieves comprehensive final position starting from the partial final position. Full final position for the comprehensive treatment plan may be produced manually, automatically or semi-automatically, as mentioned above, and is stored separately in apparatus. Once the partial treatment plan is ready, full final position is discarded.

To ensure that the partial treatment plans generated as described herein (optimized treatment plans) do not introduce or worsen orthodontic problems, additional inequality constraints may be introduced. As discussed above, each identified orthodontic problem, such as deep bite or class, may be measured as a single numerical value. Next, two inequalities constrain such measurement in partial setup to the range between the initial value and the comprehensive treatment. Former inequality ensures that partial setup does not worsen the problem over the initial position. The second (optional) inequality may ensure that partial setup does not overcorrect the problem unnecessarily.

By including a comprehensive final position, and incorporating it the merit function and constraints of the non-linear optimization problem, and solving this problem using the generic optimization algorithms, the method described herein may produce treatment plans that fully satisfy the constrains from the product and user preferences, while optimally resolving chief concerns, improving and maintain other orthodontic measurements.

The methods described herein can be straight-forwardly applied to all products with limits on number of stages or amount of tooth movement. By building such plans automatically, they may enable a dental professional to review multiple plans for a product range, or customize product while reviewing the updated treatment plan, as described above. Restriction on the number of stages may be replaced or supplemented with other restrictions and goals; this may allow the method to incorporate chief concerns, doctor's preferences and predictability models into comprehensive treatment plans as well.

The methods and apparatuses described herein are also fully compatible with the use of biomechanical solutions that can potentially be combined with optimization of final and intermediate tooth positions to produce treatment plans with movements that are fully supported by the appliance (e.g., aligner) design.

Collision Detection

Construction of orthodontic treatment for a patient must account for limitations on mutual position of teeth, including amount of space and interproximal reduction. Computing exact amount of collisions and spaces between teeth may be a computationally intensive operation that impacts cost and quality of automatic treatment plans. Described herein are methods and apparatuses (e.g., such as system for automatically detecting collisions between teeth, which may be referred to as collision detectors) for constructing approximated shapes of teeth by packing the surface(s) of the teeth, or in some variations, other structures (e.g., attachments, brackets, etc.) using multiple three dimensional (3D) shapes (such as capsules) having a planar figure (e.g., line, rectangle, etc.) in the core, and an outer surface extending a constant radius from the core in x, y and z. Collisions (e.g., overlap) between the teeth may be analytically determined from the 3D shapes with high precision. These systems and methods may also be applied to just adjacent portion of the teeth (rather than the entire teeth) and may be combined with a hierarchy of bounding boxes in order to accelerate the computation. Compared to precise generic technique or estimating collision, these methods and apparatuses described herein may be two or more orders of magnitude faster, and may allow the systems and methods described above for calculating one or more treatment plans (e.g., a solver or a treatment plan solver) to incorporate these collision detectors. Furthermore, any of the methods and apparatuses described herein may determine both the magnitude of the overlap (or in some cases, the closest separation) between the teeth, but may also be configured to determine the velocity of the overlap (e.g., in three or more spatial directions, such as x, y, z and/or yaw, pitch, roll).

Figure 29A:
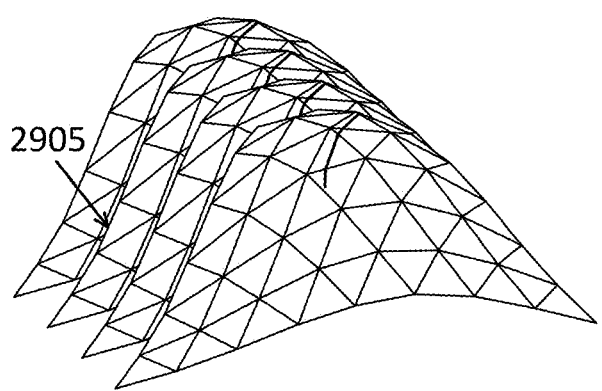
FIG. 29A shows an example of a triangular mesh surface approximation.
Figure 29B:
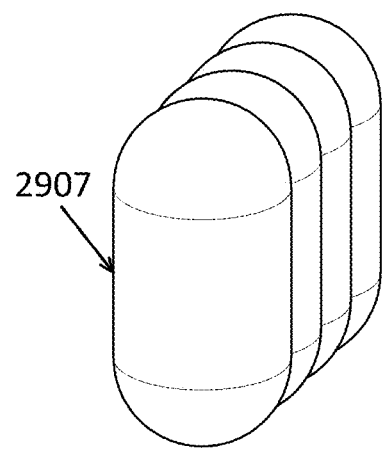
FIG. 29B shows an example of a surface approximation by packing with 3D shapes (shown as capsules) to approximate a surface and some or all of the internal volume of a three-dimensional object (or the portion of the object adjacent to a second object).

FIG. 29A illustrates the use of a triangular mesh 2905 to model the surface of a shape, such as a tooth. Surface modeling using a triangular mesh may be used to model adjacent teeth and the modeled surface may be used to estimate the distance between objects such as teeth. FIG. 29B shows an example of a group of three-dimensional (3D) shapes, shown as capsules, in which the 3D shapes each have a core that is a line or a plane figure and an outer surface that is a constant radius from the core. In FIG. 29B the capsules 2907 are formed by a core that is a line. As will be described in greater detail below, modeling the surfaces of adjacent teeth by packing these surfaces (and internal regions) with capsules as described herein may be used to determine collisions between the shapes much more rapidly than other methods, including modeling by triangular mesh, as shown in FIG. 29A. For example, a tooth surface may be modeled with high precision using 2000-8000 triangles; the same surface may be modeled using 50-200 capsules with nearly equivalent precision. Because the capsules have both flat and convex regions they may be particularly well suited to modeling shapes such as the surface of a tooth. Using 3D shapes having a constant radius from a planar shape (e.g., line, rectangle, etc.) may be used to calculate the distance between the surfaces more than five times faster compared to modeling with triangles at an equivalent precision. The 3D shapes, such as capsules, are typically solids, and may therefore be used for fast penetration depth computation.

Figure 29C:
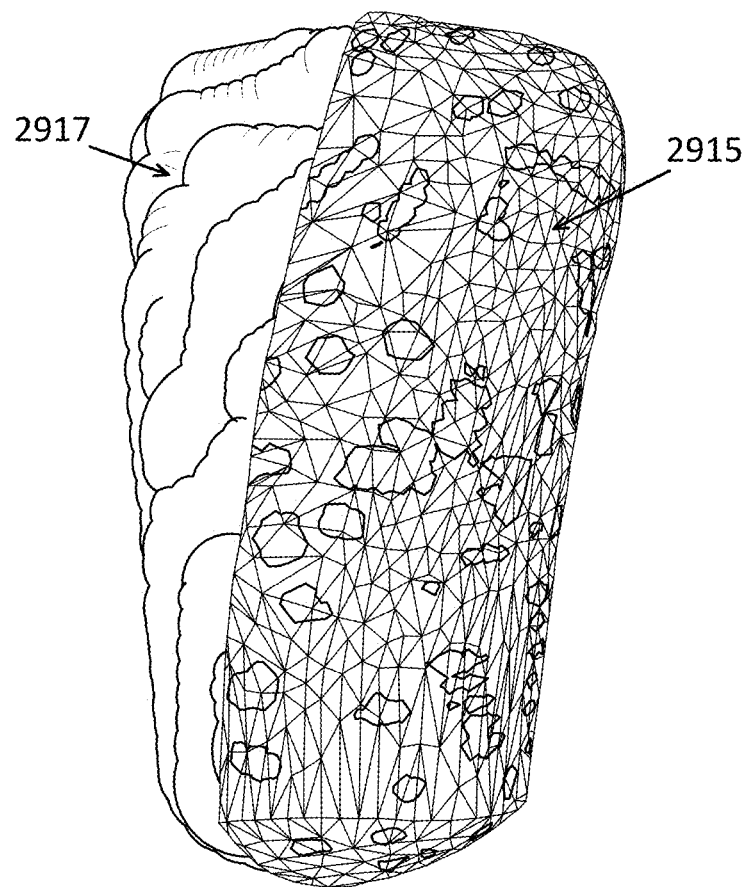
FIG. 29C is an example of a comparison of a tooth having a surface approximated by both a triangular mesh (on right) and packing with 3D shapes (on left, shown as capsules).

FIG. 29C shows a side-by-side comparison of a tooth modeled with both capsules 2917 (entire tooth) and triangular mesh (right side 2915). In practice, the patient's teeth only need to be modeled by packing with three dimensional shapes such as capsules once; thereafter the overall tooth position may be changed, but the same surface modeled by the 3D shapes may be used to examine collisions/spacing for multiple different arrangements of the teeth.

Any appropriate 3D shape having a core that and an outer surface that is a constant radius from the core may be used, although it has been found that using shapes with at least partially linear cores (e.g., capsules, rounded rectangles, etc.) may be particularly beneficial for modeling the tooth surfaces and estimating distanced, including collisions, and depths of collision. For example, FIGS. 30A-30C show sections through 3D shapes having a core and an outer surface that is a constant radius from the core are shown; the corresponding figures shown are shown in perspective view in FIGS. 31A-31C. In FIGS. 30A and 31A the shape is a sphere having a core 3001 that is a point at which the radius, r, 3003 originates. The use of a sphere, which has only a concave outer surface, for packing a complex shape such as the tooth surface may be suboptimal, in part because the surface of the tooth includes regions that are not concave. The use of spheres may require a larger number of smaller spheres for packing to approximate the tooth surface compared to other shapes such as capsules like those shown in FIGS. 30B and 31B. In FIGS. 30B and 31B, the capsule has core that is a line segment 3005, and an outer surface that is a constant radius, r, 3007 on all side of the line in x, y and z space. Similarly, FIGS. 30C and 31C show an example in which the core is a closed planer shape, shown as a rectangle 3009 having a constant-length radius 3011 extending from the surface. The outer surfaces are shown in the perspective views of FIGS. 31A-31C.

When modeling the tooth using the 3D shapes such as capsules, a variety of different capsule sizes may be used; the capsules may have different lengths of the core line segment, and/or the radius of each capsule extending from the core may be different (though typically the same radius length in an individual capsule). Alternative or additionally, different 3D shapes may be used.

FIGS. 32A and 32B illustrate top and side perspective views, respectively, of a patient's molar 3201 that has been modeled using a plurality of capsules. In this example, the entire outer surface of the portion of the tooth above the gingiva has been modeled by packing with capsules. In practice one or more teeth may be modeled from a digital model of the patient's tooth or teeth. For example, a digital scan of the patient's teeth (e.g., from an intraoral scan, a scan of an impression of the teeth, etc.) may be provided and the surface of the teeth may be modeled by packing the tooth surface (and all or the peripheral region of the tooth volume) with a plurality of 3D shapes, such as capsules. An optimization algorithm may be used to automatically position a small number of capsules to approximate the tooth surface as close as possible. The precision of the match with the tooth surface may be set as a parameter, so that the minimum number of capsules (or maximum size of capsules) necessary to model the surface within the set precision may be determined.

In variations in which the patient's teeth are digitally scanned, the digital scan may be segmented into individual teeth (or groups of teeth) and each segmented region, e.g., tooth, may be modeled with 3D shapes (e.g., capsules). In some variations the tooth or teeth may already be modeled in another manner (e.g., by triangles as described in FIG. 29A) and the existing model may be modeled with the 3D shapes.

To model an individual tooth (or group of teeth), the tooth may be packed with capsules so that difference between tooth's surface and the outer surface of the capsules is as low as possible. In this model, only the 3D shapes, e.g., capsules, are used for approximations; these 3D shapes may be constructed quickly and may be analyzed quickly. As will be described in greater detail below, in some variations, only a part of a tooth may be approximated. For example, only the IP area, incisal area, crown, etc. may be modeled; for example, only the side of the tooth facing the adjacent tooth may be modeled. Alternatively, the whole tooth shape may be modeled. In some variations, the tooth shape may be decimated before approximating. For example, the tooth shape may be simplified by filtering (e.g., smoothing, etc.). Alternatively or additionally, the original shape can be used to obtain more precise approximations. In some variations, all of the teeth (or subsets of teeth) can be modeled simultaneously, e.g., in parallel. Alternatively, teeth may be modeled one-by-one, e.g., sequentially.

Modeling the tooth may be iterative. The surface may initially be filled with non-overlapping 3D shapes (e.g., capsules) as a starting configuration. Each iteration may include: finding the area of shape which is approximated by capsules the worst (e.g., comparing the digital tooth surface, or "actual surface," to the 3D shape-filled surface). On optimization problem may be constructed for approximating this area with 1 capsule object. For example, the following relationship may be minimized, subject to the constraints that the end points of each capsule must lie inside of the convex hull of the tooth shape, and each least square straight-line (LSS) closet vertex from the tooth shape should not be farther than some small limit:

$$\sum_k \left[ \omega_k \min_m \text{Distance}(vertex_k, capsule_m) \right]^2$$

In this relationship, $w_k$ is the weight for vertex $v_k$ of the original shape. For interproximal (IP, the region between adjacent teeth) area approximations:

$$\omega_k = f(\{vertex_k\}_y^2)$$

This may be solved with an optimization solver, and a newly found surface may be added to the approximation, while obsolete surfaces may be removed from the approximation. The total approximation may then be refined. This process may be repeated (iterated) as much as necessary until the desired precision is achieved.

For example, in some variations, the systems and methods described herein may select a subset of vertices from the digital model (e.g., scan) of the tooth surface, and may approximate this subset of vertices with one capsule. An optimization solver may be used to minimize the distance between the capsule and the selected subset of points. If the approximation is poor (e.g., below some threshold for approximation), the set of point is not adequate, and the subset of vertices may be revised to find points within the vertices that may be approximated better, or finding new sets of points that may be approximated more closely within the desired range (e.g., another capsule may be identified to approximate the smaller subset of points). Once the initial packing of capsules has been completed, each approximating a small subset of points on the tooth, the optimization process may be repeated with some of the capsules rearranged to achieve a higher precisions. The process may stop when the maximum amount of capsules desired is reached. For example, the threshold number of capsules may be set to, e.g., 15 capsules (10 capsules, 12 capsules, 15 capsules, 20 capsules, 25 capsules, 30 capsules, 35 capsules, etc.). Alternatively, in some variations, the process may be repeated until a precision limit or threshold is reached, without limiting the number (and therefore size) of capsules. For example, a precision limit may be set to require filling of all spaces bigger than 0.001 mm. Alternatively, a combination or balance of the two (number of capsules and/or minimum precision limit) may be used, for example, increasing the number of capsules if the precision is within a predefined range.

Although FIG. 32A-32B illustrates an example of an entire tooth modeled using a plurality of capsules, other structures may also be modeled, including other dental structures that may be present on the tooth or associated with the tooth. For example, FIGS. 33A-33B illustrate perspective views of a portion of a dental appliance (a precision wing portion 3301) that has been modeled by packing with a plurality of 3D shapes (e.g. capsules). In some variations, this may be beneficial for detecting collision between the teeth and an orthodontic device, or between multiple orthodontic devices, etc.

Figure 34A:
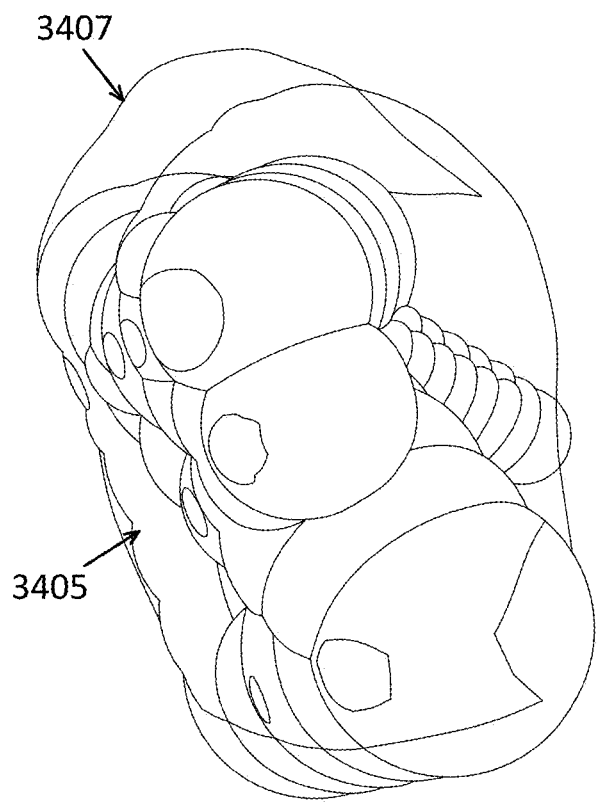
FIG. 34A illustrates another example of a tooth having a first (left) side surface that is formed from the digital model of the tooth by packing a plurality of 3D shapes (capsules in this example) to approximate the surface.
Figure 34B:
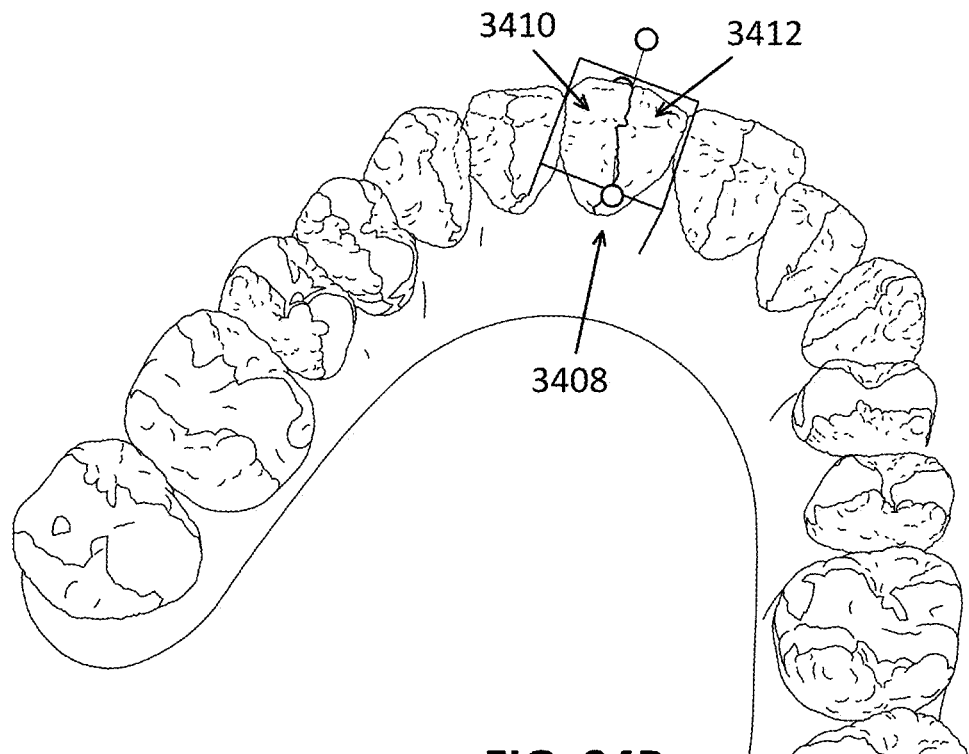
FIG. 34B illustrate a digital model of a plurality of the patient's teeth (shown here as the patient's maxillary arch) in which each tooth has been divided up into regions (e.g., left and right or left, right and middle regions) so that the surface of the tooth in each region can be modeled (e.g., formed) by packing a plurality of 3D shapes (e.g., capsules) to approximate the surface.

FIG. 34A illustrates an example of a tooth having a surface (an interproximal surface) that is modeled using a plurality of capsules. In FIG. 34A, the left interproximal surface 3405 is approximated by packing the surface with a plurality of capsules of various sizes. Other region of the tooth (e.g. crown region) are not modeled, or not modeled to the similar precision. In some variations, multiple regions associated with the same tooth may be modeled separately, such as left and right interproximal regions, crown regions, etc. FIG. 34B illustrates a dental arch including a plurality of individual teeth. Each tooth is divided up into left and right sides, and in some teeth (e.g., molars, premolars) a separate middle region; the left and right regions may be modeled separately. For example, the boxed incisor 3408 includes a left side 3410 and a right side 3412, shown by different shading, and similar distinctions can be made for all of the teeth.

Once one or more surfaces of the teeth have been digitally modeled by packing 3D shapes, a hierarchy of bounding boxes may be formed around all of the 3D shapes and adjacent sets of shapes for each modeled surface of each tooth. Building a hierarchy of bounding boxes may provide a rapid and efficient way to determine which capsules between two adjacent teeth may be closest to each other and/or may overlap. The use of bounding boxes, and particularly an organized hierarchy of bounding boxes, may reduce the time for finding closest pair of capsules dramatically. The bounding boxes allow the rapid determination of an approximate value of a collision/separation in space, instead of a precise one. The approximate value may be calculated as a minimal distance between all possible pairs of capsules of two shapes. For example, approximate collisions can be used in optimization process of treatment plan generation to provide a good initial guess of teeth position that fulfills almost all requirements besides some small violations of collision/space rules left due to imprecision of approximate calculations. Those violations can be resolved by switching back to precise calculations (e.g., using the capsule distance). This combination of bounding boxes and 3D shapes, allowing both rough and more precise determination of spacing, has been found to give a substantial performance boost of up to 150 or more times compared to the use of more precise collision depth/space calculations only.

The use of the hierarchy of bounding boxes, which provide approximate collision information, with the more precise collision information provided by the 3D shapes, such as capsules, particularly by increasing the number of capsules, may allow both rapid and accurate collision/spacing information.

Figure 35A:
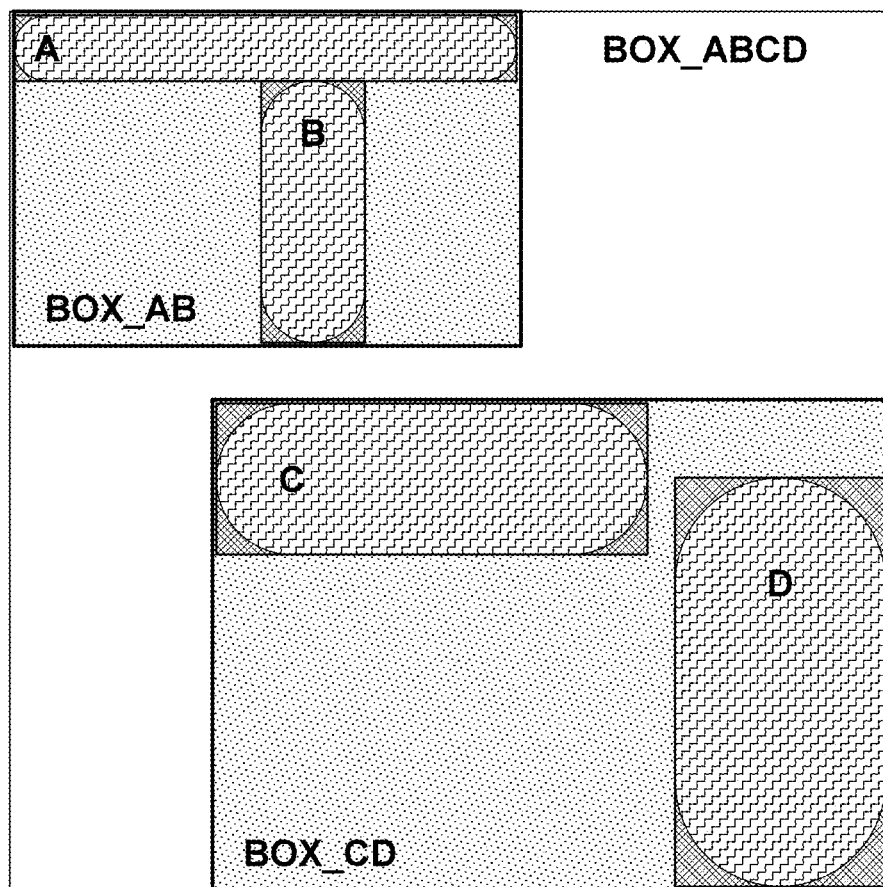
FIG. 35A illustrates one example illustrating the formation of a hierarchy of bounding boxes around capsules.

The hierarchy of bounding boxes may be organized so that each capsule is put into a bounding box that fits it tightly. Each bounding box containing one or more capsules are considered leafs of the hierarchy. Each box from a higher level of hierarchy bounds several boxes from a lower level of hierarchy. FIG. 35A illustrates one example of a hierarchy of bounding boxes for four capsules. In this example, capsules A, B, C, D are each bound in a bounding box, forming the lowest level of the hierarchy. Bounding boxes A and B are united into bounding box AB, and bounding boxes C and D are united into bounding box CD. Finally, at the top of the hierarchy, bounding boxes AB and CD are united in bounding box ABCD. FIG. 35A shows the entire hierarchy arranged as a tree, with the boxes corresponding to individual capsules at the lowest level.

Figure 35B:
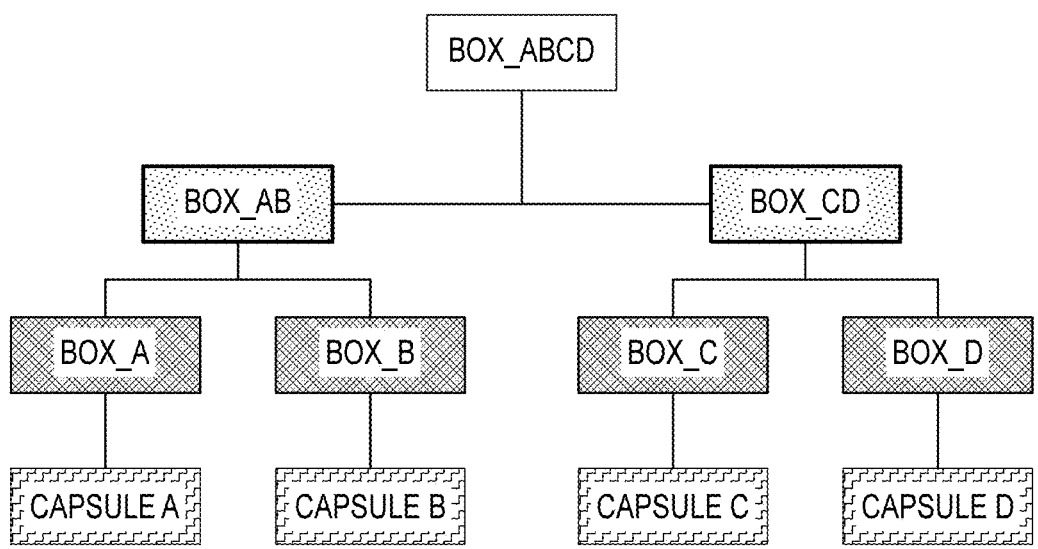
FIG. 35B is an example showing the tiers of the exemplary hierarchy of FIG. 35A, forming a tree hierarchy.
Figures 37A, 37B:
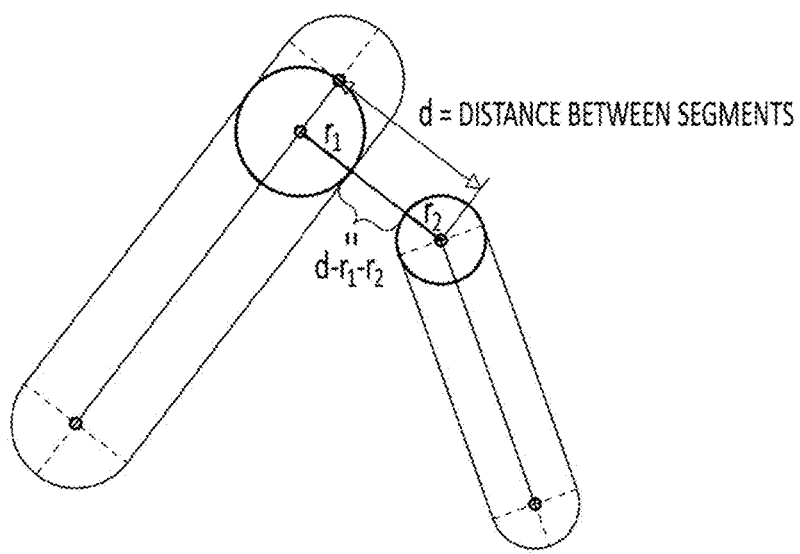
FIG. 37A illustrates one method of determining collision distance (in this example, negative collision distance or spacing) between two capsules from each of two separate surfaces being examined for collisions.
FIG. 37B is an example of pseudo code for finding approximate distance between the surfaces of two shapes (e.g., shape A and shape B) packed with capsules.

Any appropriate algorithm for construction of a hierarchy of bounding boxes can be used. Using tighter bounding boxes (e.g., having smaller volumes) may result in more efficient usage of the hierarchy in collisions computations, therefore the methods and apparatuses described herein may build a hierarchy while minimizing the volume of the resulting bounding boxes on each level of hierarchy. Each tooth may have a single hierarchy, or multiple hierarchies, e.g., corresponding to the left interproximal side and the right interproximal sides, etc. The hierarchy may be traversed to avoid calculation of distances between pairs of capsules that cannot influence the outcome value of collision/space when checking adjacent teeth for collisions. For example, FIG. 36 illustrates an example of a method (e.g., shown here as pseudo-code) for traversal of bounding box hierarchies to skip distance calculation between capsules that cannot influence the final value of collision/space. This method may start at the highest level and see if there is any collision (e.g., overlap) between the highest levels of the hierarchy by, e.g., measuring the distances between the largest (top level) bounding box for each adjacent tooth or both adjacent tooth regions. If there is no overlap at the top level, there is no collision at all. However, if there is a collision, then the next level down the hierarchy may be compared to determine which branches of the hierarchy include collisions; for each branch that includes a collision, the procedure may continue down to the next level/branch until the lowest level (capsule or other 3D shape) is reached; the final levels on both teeth, or regions of the teeth, therefore represent the regions that are colliding, and these regions may be examined to determine the depth (magnitude) of collision. FIG. 37A illustrates one method of analytically determining the distance between two capsules of different hierarchies. In general, the apparatuses and methods may measure the distance, d, between the cores of the 3D shapes and the minimum separation between the capsules in this example is equivalent to the shortest distance between the two line segments minus the radius of the first capsule and the radius of the second capsule. FIG. 37B also includes an example of a pseudo-code set of instructions for finding approximate distance between two shapes, such as, for example, shape A and shape B packed with capsules shown in FIGS. 35A-35B. Although the examples described herein include bounding boxes, other simplified bounding geometries may be used, for example, bounding sphere or bounding capsule hierarchies may be used.

In addition to detecting the magnitude of any collision that occurs when the teeth are in a specified position, the methods and apparatuses described herein may be used to determine the velocity of any collision. In doing velocity measurements, one or both teeth may be moved very small increments (e.g., less than 0.001 mm, less than 0.01 mm, etc.) in one or more axis (x, y, z axis, roll, pitch and yaw), and the resulting change in the overlap determined for each axis. The final velocity may be measured for each of the six axes, and/or may be combined into a single indicator (e.g., vector) sum or relationship.

Figure 40:
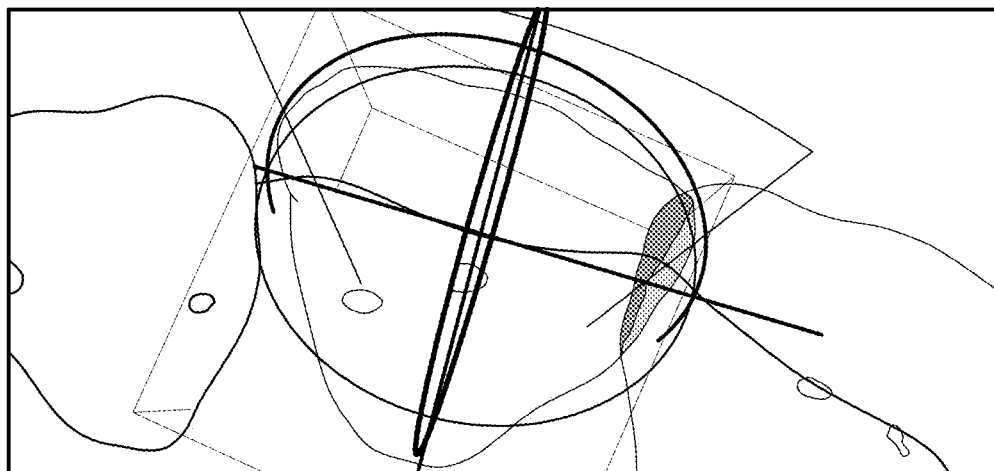
FIG. 40 is an enlarged view of one of the teeth shown colliding in FIG. 38, illustrating the six axes for which a velocity of collision may be determined.

During any of the processes for determining the velocity of a collision, in which the tooth may be 'jittered' in one or more of its axes, the closest pair of capsules in collision/space with any change in position of shape is very small. This can be used for faster calculation of gradients in optimization algorithm for determining the final position of the teeth following treatment, and for staging construction. For example, the tooth may be moved in each of the six axes (e.g., three translational axes, x, y and z, and three rotational axes: pitch, yaw and roll) by a small amount (e.g., less than 0.001 mm of translation, less than 0.01 degree of rotation, etc.). This is illustrated in FIG. 40, for example, showing the axes around one tooth. The same capsules identified as colliding may therefore be re-examined following the small movements to determine the velocity of the collision. When using the solver/engine to solve for one or more treatment plan, the solver may avoid collisions between teeth. For the solver to estimate an optimal solution when planning a treatment, the solver may be provided by not just the magnitude (e.g., depth) of the collision, but also the velocity of the collision, e.g., how the collision depth reacts to small changes of position relative to the neighboring tooth. If one tooth is fixed, but the other is moved, e.g., jittered, about its original position, the same pair(s) of capsules may be used for very rapid calculations. The depth may be defined as how close the tooth is to another tooth, e.g., in mm of overlap. In some variation, the method and/or apparatus may alternatively measure the space between the two closest capsules (e.g., even when not colliding).

Figure 38:
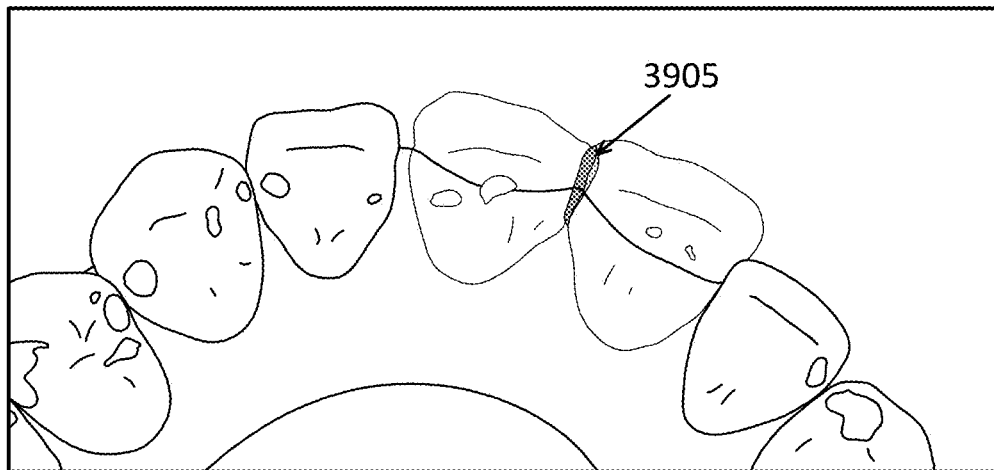
FIG. 38 is an example of a digital model of a set of teeth, including a pair of teeth shown colliding.
Figure 39:
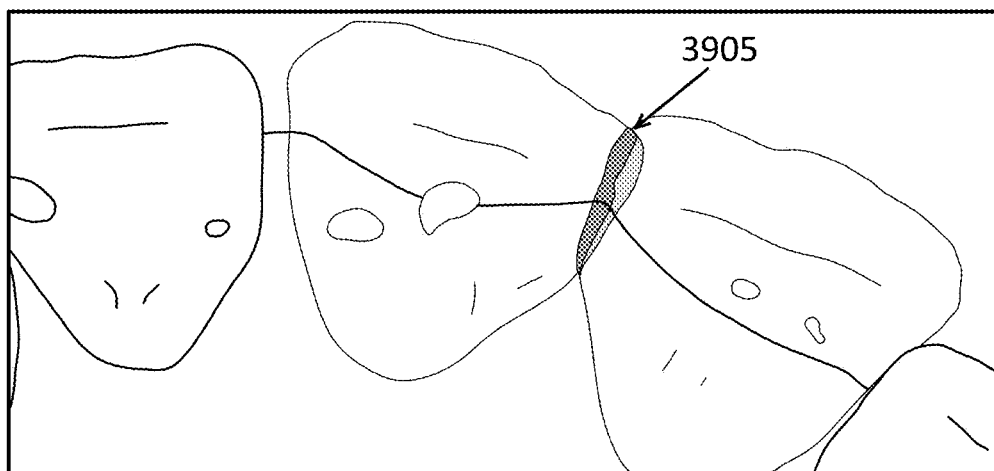
FIG. 39 is an enlarged view of the collision region between the two colliding teeth shown in FIG. 38.

In use, the method of solving for the magnitude and velocity of a collision may be integrated into a method for solving for one or more treatment plans. For example, the treatment plan solver may call on the collision detector to identify the collision and rotation between each tooth. The treatment plan solver may have initially identified digital models of the patient's teeth in which one or more surfaces were modeled by 3D figures such as capsules. See, e.g., FIGS. 38 and 39. The patient's teeth, e.g., along the interproximal regions, may be modeled as individual teeth (or set of teeth) and the overlap 3509 may be determined. The teeth do not need to be re-modeled when making additional collisions determinations. The collision detector (collision engine) may measure the change in magnitude as a collision depth, and may also determine the velocity of the changing magnitude for each of a plurality of axes.

A special variant of the method is used during construction of orthodontic treatment with a non-linear optimization based algorithm. For example, to compute gradients of change of collision or space amount, every step of a non-linear optimization algorithm may compute values for thousands of small variations of teeth positions. The result of previous computations may be used to select smaller number of capsules that must be considered to find the amount of collision or space, provided the change of position was limited by a small constant bound. This additional pruning reduces computational complexity from $O(N^2)$ to $O(1)$, and allows an increase in the number of capsules used in tooth approximation without corresponding increase of computation time, increasing the precision.

In examples in which the capsules have a planar figure (e.g., line, rectangle, etc.) in the core, and an outer surface extending a constant radius from the core in x, y and z, collisions (e.g., overlap) between the teeth may be analytically determined from the 3D shapes with high precision. These systems and methods may also be applied to just adjacent portion of the teeth (rather than the entire teeth) and may be combined with a hierarchy of bounding boxes in order to accelerate the computation, as described above.

Any of the methods and apparatuses described herein, including subcomponents or subsystems (e.g., such as system or subsystem for automatically detecting collisions between teeth, which may be referred to as collision detectors) may be configured for constructing approximated shapes of teeth by packing the surface(s) of the teeth, or in some variations, other structures (e.g., attachments, brackets, etc.) using multiple three dimensional (3D) shapes (such as capsules), as described above, and these 3D shapes ("capsules") may be selected based on the shape(s) of the product being modeled, including teeth and/or other structures, such as retainers, attachments, etc. As describes above, in general approximation of shapes using the capsules as allows a dramatic reduction in the time necessary for collision computations which may be a bottleneck in treatment plans construction. However even if the accuracy of approximation is not high, a filling (e.g., capsule-based) technique may still be useful in eliminating remaining collisions when modeling. In some variations, the construction of high-precision approximations can result in significant time savings even without requiring a refinement of treatment plans with precise computations.

Figure 41A:
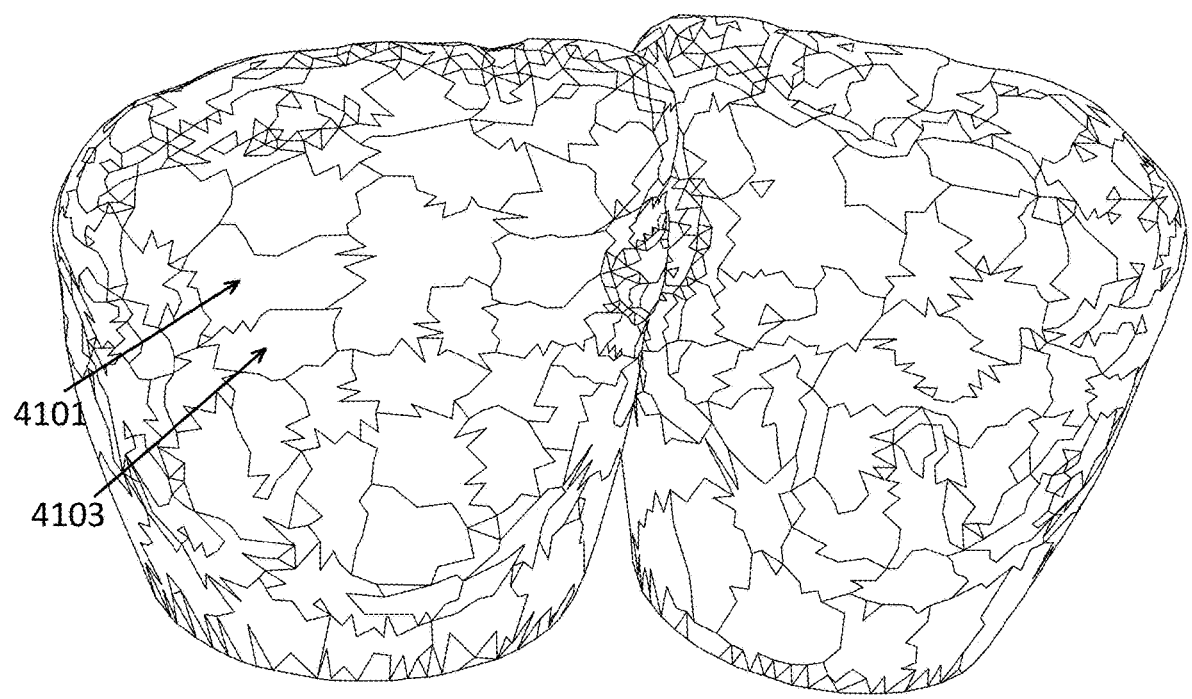
FIG. 41A shows one example of a pair of tooth shapes showing regions having close (closed) curvatures.

For example, in some variations topographical information about the face(s) of the teeth or other targets being modeled may be used to select the size, shape and/or position of the capsules. In some variations topological information about faces (such as curvatures) is used to find regions best suitable for approximation with single capsule. This may be accomplished by identifying one or more areas on a shape having a closed curvature; in some variations, when the capsules consists of spheres of fixed radius, or shapes based on a fixed radius, they may not efficiently approximate areas that have different curvatures. FIG. 41A illustrates one example of a pair of tooth shapes showing regions having close (closed) curvatures that may be approximated using a single capsule. In FIG. 41A, each of the different regions (shown by different shading), e.g., 4101, 4103, has a close curvature. Use quadric error metric to measure distance from shape to approximation. Any appropriate method may be used to determine the curvature of the surface.

Figure 41B:
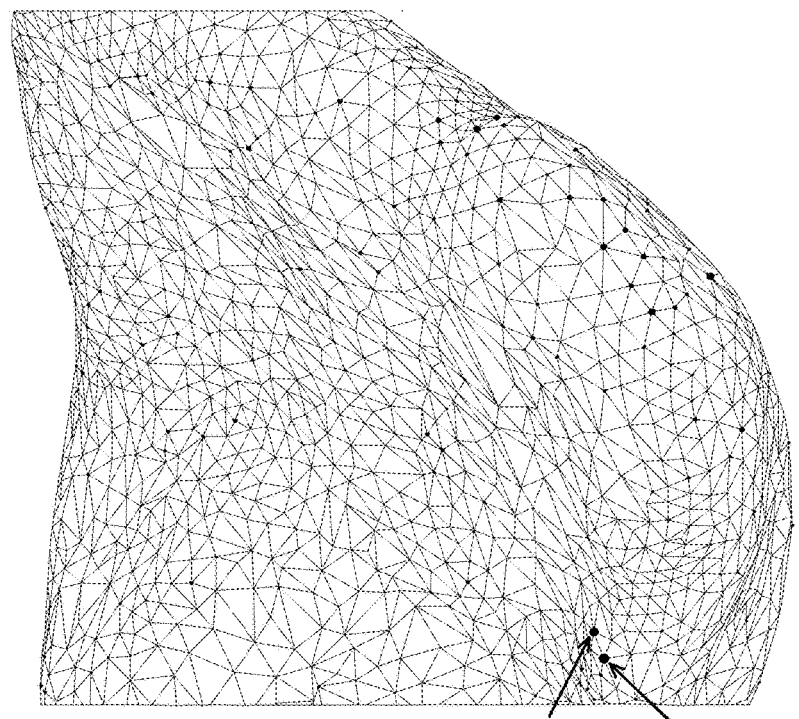
FIG. 41B is a 3D model of a patient's teeth showing regions having close (closed) curvatures.

Once identified, the curvature may be used to determine the shape, size and/or position of the capsules. Capsule approximations may be refined on the fly. For example information about approximation quality in different regions may be determined, stored, and used to refine approximations interactively if collision was requested in a particular (e.g., a "bad" region, or region of high error, as shown in FIG. 41B). In FIG. 41B, the shaded dots of different sizes show regions having approximation errors (e.g., the relative sizes of the dots 4109, 4109' in FIG. 41B reflect the approximation error at each dot position).

For example, described herein are methods of determining/detecting collisions as described above, in which an initial partitioning of the three-dimensional shape(s) (e.g., teeth) may be based on curvatures of the outer shape surface. Thus, the method, or any apparatus configured to perform it, may identify a face of the outer surface that is close. For each face, the method or apparatus may construct a vector with coordinates (x1, . . . , x7) where x1 . . . x3 are coordinates of center of a face, x4 . . . x6 are coordinates of vector $(k_1*d_1+k_2*d_2)\hat{}n$ ($k_1$, $k_2$ are principal curvatures of face, $d_1$, $d_2$ are principal directions, and n is normal to face), and x7 is a mean curvature of a face defined as $k_1+k_2$.

A clustering algorithm may then be used with the constructed set of vectors, and the number of clusters should be equal to desired number of capsules. In this technique, the center of each cluster may be used to construct a capsule to be used by an optimization algorithm as an initial guess. A quadric error metric may be used to control approximation sticking from 3D shape; for measuring a distance between a capsule and a plane, the following definition may be used:

$$\text{Distance}(\text{Capsule},\text{Plane})=\min(\text{quadric error metric}(s(t,r),\text{Plane}))$$

In this technique, t belongs to [0,1], s(t) is sphere with center p0+t*(p1−p0), p0 and p1 denote end points of capsule, r is radius of capsule. This metric differs from the distance from an un-oriented point p (as opposed to a plane {p, n}) to a capsule; it also takes into account the orientation of the normals, and distinguishes naturally between convex and concave regions.

As mentioned above, any of these methods may include refinement of capsules on the fly. For example, after an approximation is computed, the apparatus or method may include marking poorly approximated areas with marker (e.g., flag). A collision computation may check if any poorly approximated areas lie near a potential collision area; if so, the method or apparatus may perform a capsule construction for the affected areas (near potential collisions; other regions with a low probability of collisions may be ignored, even if poorly approximated). Newly constructed capsules may then be added to the approximation, and the collision results may be recalculated using the newly constructed capsules.

Figure 41C:
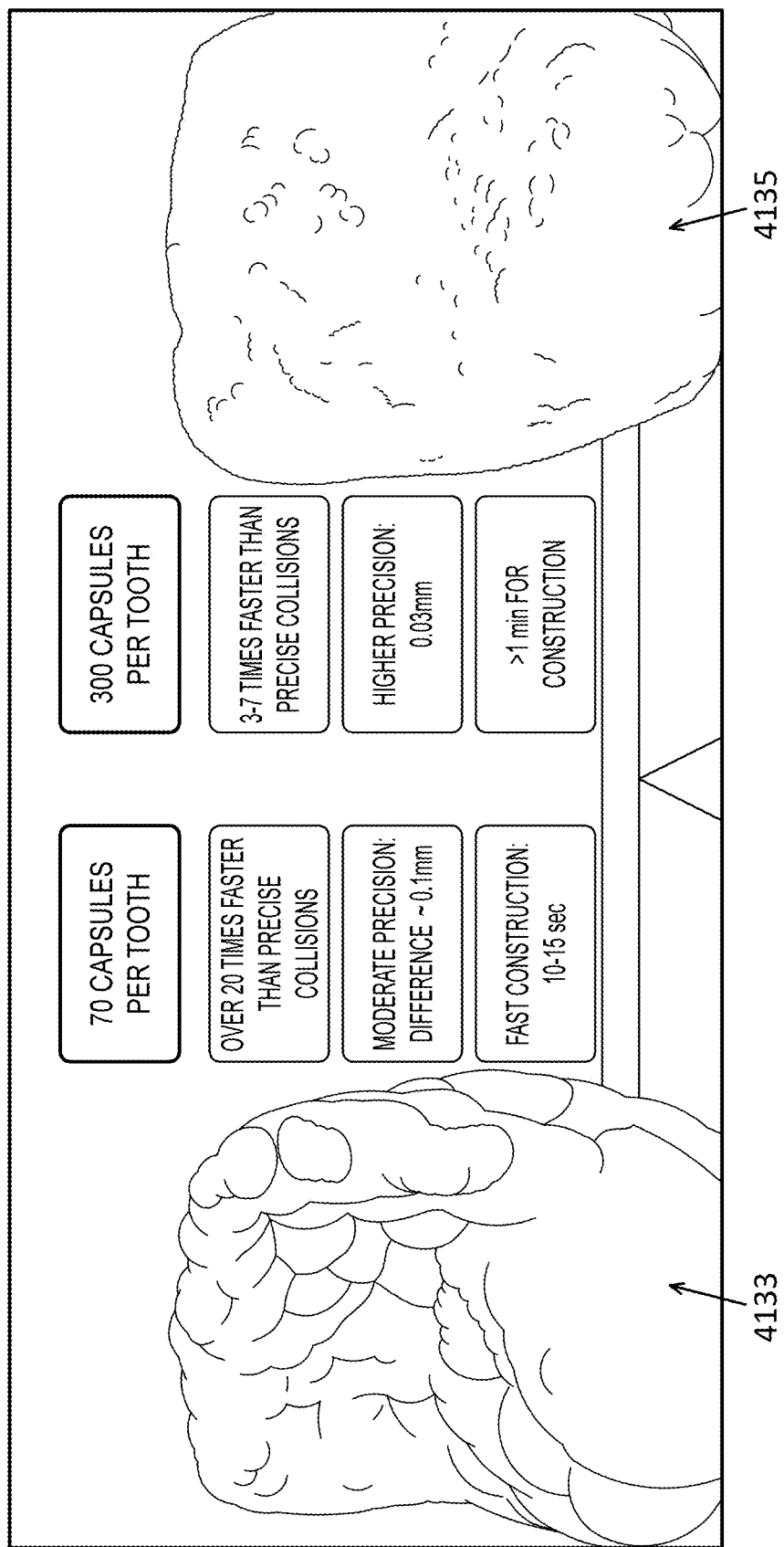
FIG. 41C is a comparison between moderate precision (left) and high precision (right) estimation of tooth volume for collision estimation using different 'capsule filling' techniques described herein.

The methods described above may be used to dramatically increase the speed and/or efficiencies of these techniques. For example, FIG. 41C illustrates an example of a comparison between collision detection using capsule approximations at different levels of precision. In FIG. 41C, the right side 4133 is an approximation of a tooth in which 70 capsules are used to approximate the tooth surface (e.g., 70 capsules per tooth), while the right side 4135 is an approximation using 300 capsules per tooth. The approximation using 70 capsules per tooth was over 20× faster (e.g., taking 10-15 seconds for the reconstruction) than a precise collision detection method (e.g., using a triangular mesh), while the 300 capsules per tooth was between 3×-7× faster (e.g., taking >1 minute for the reconstruction). The 70 capsules/tooth 4133 example may be considered a "moderate precision" technique, having a difference compared to a precise model of approximately 0.1 mm, while the 300 capsules/tooth 4135 example is a higher precision model, having a difference compared to a precise model of approximately 0.03 mm.

EXAMPLE

An example of a method for generating an optimal partial treatment plan may include, for example, determining (in a computer processor) an initial position of each of the patient's teeth (position and orientation, in six variables) from a digital model of the patient's teeth. The digital model can be the upper jaw, lower jaw or both upper and lower jaws. The software typically divides the models into individual teeth and positions them into patients bite relationship. The steps of determining the position of the patient's teeth may be done in the same processor (or as part of the same device) that does the rest of the method (e.g., solves for the solution vector) or it may be a different, separate processor. Any of these methods may then determining a comprehensive (e.g., "optimal") final position of the patient's teeth.

A processor performing the method may then receive product definition (e.g., number of stages to be used) specific to the patient treatment. Other product information may include: maximum allowed number of stages, whether attachments are allowed, maximum allowed root movements, crown movements and rotations, etc.

Thereafter the processor may receive preferences (e.g., interproximal reduction, attachments, tooth/teeth that don't move, etc.) specific to the patient treatment. Preferences may include: indicating which tooth/teeth are not to move, individual teeth where attachments should not be placed, arch to treat (both jaws, only lower or only upper), class correction amount and method, IPR, arch expansion, spaces, levelling preferences, etc.

The processor may then express a plurality of treatment targets of the treatment plan as numerical functions ("target functions") based on the product definition and preferences, weight each numerical function, and sum them to form a single numerical function. This single numerical function may include a weighted sum of at least, for example: tooth position compared to the comprehensive final position of the patient's teeth, misalignment (x- and z-misalignment, alignment to arch), diastema (spaces between neighboring teeth), collisions (inter arch collisions), and length of treatment (number of stages). Thus, the single numerical function (e.g., the merit function) is a nonlinear combination of treatment targets (target functions) weighted by pre-defined coefficients. Typically, key components of the merit function are objective (independent of the comprehensive position) measurements of aesthetic concerns: misalignment between teeth, spacing between teeth, amount of overjet and amount of overbite. Components that are relative to comprehensive final position mostly describe orthodontic goals (arch form, occlusion, levelling, alignment, etc.).

The pre-defined coefficients may be set or determined empirically, e.g., by expert opinion, or may be solved. For example, starting from initial guess where weights are roughly same, setups may be prepared for cases from an existing database and reviewed. In addition, some adjustments can be made for technical reasons (i.e. to improve converging to a solution, which may be delayed if weights are inconsistent).

Constraints on tooth movements may then be expressed as numeric limits based on the product definition, preferences and comprehensive final position, including at least: the maximum velocity of tooth movement, maximum amount of collision, tooth movement limitations, staging constrains, and maximum amount of occlusion. As discussed above, other constraints may include: the maximum velocity of tooth movement, maximum amount of collision and space, tooth movement limitations, staging constrains, maximum amount of occlusion, amount of overbite, overjet, and midline position.

The single numerical function subject to the constraints on the tooth movements may then be solved (e.g., minimized) using a constrained optimization algorithm to get a solution vector and map the vector to a treatment plan. One example of a constrained optimization algorithm is the Interior Point method, including Interior Point method variations SQP and Active Set. Other methods may alternatively or also be used.

The solution vector is produced as a result of solving the constrained optimization algorithm. The optimization problem is defined as finding the values of variables $x_1 \ldots x_N$ that minimize merit function $f_0(x_1 \ldots x_N)$ and do not violate inequality constraints $f_i(x_1 \ldots x_N)$. Solution vector is the values of $x_1 \ldots x_N$ that optimization algorithm produced as an output. Variables are mapped positions teeth, for every key-frame on every tooth there are seven variables: x, y, z coordinates, angulation, inclination and rotation angles, and stage number of the key-frame. For example, $x_1$, $x_2$, $x_3$, $x_4$, $x_5$, $x_6$ may be the initial position of molar, $x_7$ would be constant stage 0 (initial), then $x_8 \ldots x_{14}$ would be position, angles and stage number of intermediate key-frame added to molar for staging, then $x_{15} \ldots x_2 i$ are final position of the molar and final stage number (length of treatment). Then $x_{22} \ldots x_{43}$ are initial, intermediate and final positions and stage numbers of pre-molar, and it continues for every tooth. There may be different number of intermediate, staging key-frames on each tooth, so 14 variables per tooth at minimum, to 42 and more variables for teeth with many staging key-frames). If multiple intermediate key-frames are present on a single tooth and their order is not fixed, each coordinate (such as angulation) of tooth at every key-frame may be calculated instead as a sum of piecewise functions parametrized by the stage number and coordinate variables. The piecewise functions may be defined so that if $x_i \ldots x_{i+6}$ variables corresponding to six coordinates at a key-frame are equal to zero, tooth movement through this key-frame is linear, which is equivalent to absence of key-frame.

Figure 26A:
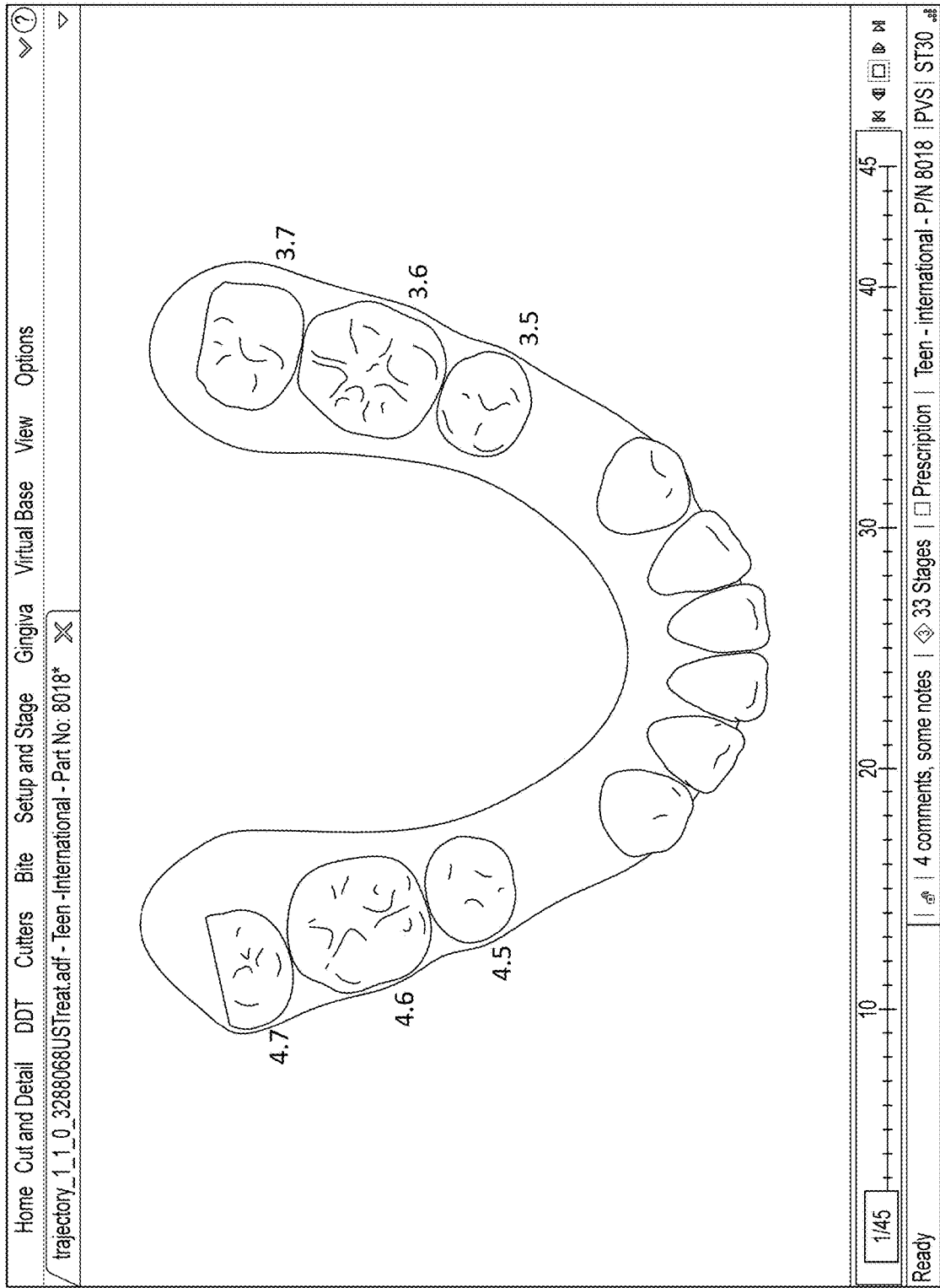
FIGS. 26A-26B illustrate annotation of tooth movement showing a trajectory with four key frames.
Figure 26B:

FIGS. 26A-26B illustrate one example of a set of key frames. Key frames are described in greater detail in U.S. Pat. Nos. 8,038,444 and 6,729,876, herein incorporated by reference in their entirety. The number of key frames used may be predetermined, or may be determined by the apparatus or method. Each tooth may have a different number of key frames.

Key frames may be used to simplify the treatment plans. For example, treatment plants may be stored as positions of key frames of every tooth. A key frame is essentially an animation of teeth movement from position at initial stage, through all key-frame positions to the position at a final stage. Thus, the treatment plan does not need to store positions for every stage. Defined positions may be at initial, final, and one or more intermediate stages that are referred to as key frames. The position of tooth on a stage that is not a key frame is interpolated between the two adjacent key frames. Thus, as mentioned above, staging, i.e., intermediate positions, of each tooth may be a linear combination of several functional component. Each component describes deviation from linear movement at a certain stage and is parameterized by six coordinate deviations and a stage number.

User-Specific Treatment Preferences

The methods and apparatuses described herein typically use treatment preferences to, in part, define the target functions (and therefore merit function) and constraints that are then used to automatically pre-calculate one or more treatment plans. Each user (e.g., dental professional) may use the same general treatment preferences when treating different patients. It would be very helpful to customize treatment plan generation (and display) to the users, particularly as the same users may worth with many patients.

For example, it would be beneficial to personalize treatment planning automation for all users (e.g., dental professionals). This may be done using domain-specific language that can be integrated into the methods and apparatuses described herein. For example, the start of any treatment (including patient consultation) may include a questionnaire or template that the user completes. The treatment planning optimization engine may use a treatment template described with a domain specific language in order to control case processing flow to create treatment according to personal needs of the user.

There may be two sources of dental professional's preferences on how to prepare treatment plans. One source of treatment preferences which may be essentially a structured input where for a set of questions, the user provides answers, where each answer is a selection from a set of predefined answers. The second source of information may be represented as a text-based comments which defines the user's personal rules to follow when preparing a treatment plan for a doctor. Domain specific language may be used to store user's non-structure input (e.g., text comments describing his treatment preferences) which may enable full automation of treatment planning as well as aggregation of rules from multiple sources (for example, structured preferences and non-structured treatment preferences).

Structured treatment preferences may cover only a small portion of users' personal treatment protocols. Instead, much of the treatment protocol details may be provided by the user in non-structured, text form. While setting up a treatment plan, a technicians uses both structured treatment preferences and non-structured treatment preferences. If this information were used manually, when a technician applies text-based user preferences, misinterpretation and inconsistency in treatment plan quality may result, and the resulting treatment plan may depend on the technician. As described herein, text-based comments expressing doctors treatment planning style may be converted into a domain-specific language (manually or automatically) and the methods or apparatus (e.g., software) may interpret this domain-specific language to automatically apply doctors preferences for treatment planning preparation.

From the users perspective, the user fills two sections of his preferences describing his treatment style, e.g., on a web site. One section may be represented as questions with predefined set of answers each, and another second may be text-form comments. The user may then saves her preferences, and both types of preferences may then be applied to cases associated with (e.g., submitted by) this user.

The user's text-based preferences may be transformed into a domain-specific language which defines clinical rules to apply for treatment planning in a formal way which also may be interpreted by Treat treatment planning software. This may initially be performed manually or semi-automatically, and may initially include manual review and checking (including checking with the user). However, once the domain-specific language is constructed for that user, it may be used without requiring manual intervention, unless modified at the user's request (e.g., when displaying the resulting treatment plans, as described herein). Each user may be associated with a rules file that may be unique to the user and may be updated independently from other users.

When case is submitted by a user (e.g., requesting a treatment plan), the user's preferences, expressed in a form of a domain-specific language, may be accessed from the stored database and aggregated with other user preferences (e.g. patient-specific target preferences or additional structured input provided by the user) and may be used to execute the fully automated treatment planning described above.

Figure 27:
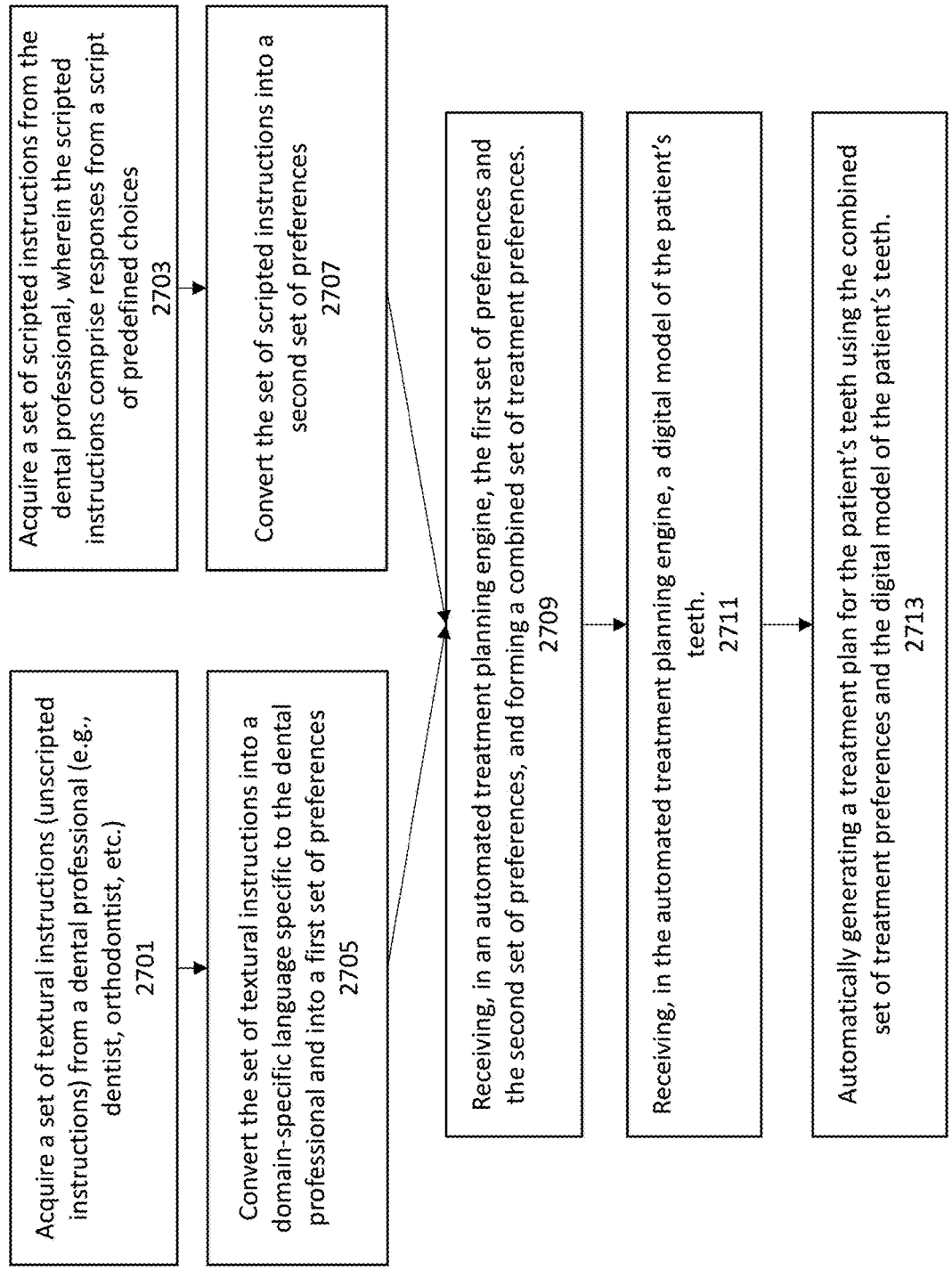
FIG. 27 illustrates one method of generating treatment preferences (e.g., user-specific/dental professional specific treatment preferences) that may be used to automatically generate a treatment plan or set of treatment plans.

FIG. 27 illustrates one method of defining user-specific treatment preferences based on both structured and unstructured input. For example, in FIG. 27, the method (or any apparatus configured to perform this method, which may be a treatment plan optimizing engine or treatment plan optimizing generator) may first acquire a set of textural instructions (e.g., unscripted instructions) from a user (e.g. a dental professional such as a dentist, orthodontist, etc.) 2701. These may be typed or handwritten (and converted to a machine readable form) and then converted into a domain-specific language specific to the user; this represents a first set of rules (treatment preferences). As mentioned above, this step may be initially performed semi-automatically or manually to build the domain-specific language. Once built, it may be fully automatic 2705.

Concurrently or sequentially, the method may acquire a set of scripted instructions from the user. The scripted instructions may comprise responses from a script of pre-defined choices (e.g., a survey, questionnaire, etc.) 2703. The responses to the set of scripted instructions may be automatically converted into a second set of rules (treatment preferences) 2707. Thereafter, the method may include accessing, by the automated treatment planning engine, the first set of treatment preferences and the second set of treatment preferences, and forming a combined set of treatment preferences from them 2709. The automated treatment planning engine may then access (e.g., receive, look-up, etc.), a digital model of the patient's teeth 2711, and any of the other inputs necessary to automatically generate a treatment plan for the patient's teeth using the combined set of treatment preferences the digital model of the patient's teeth, a comprehensive model of the patient's teeth and/or treatment details (e.g., product details), as already described above 2713.

Figure 28:
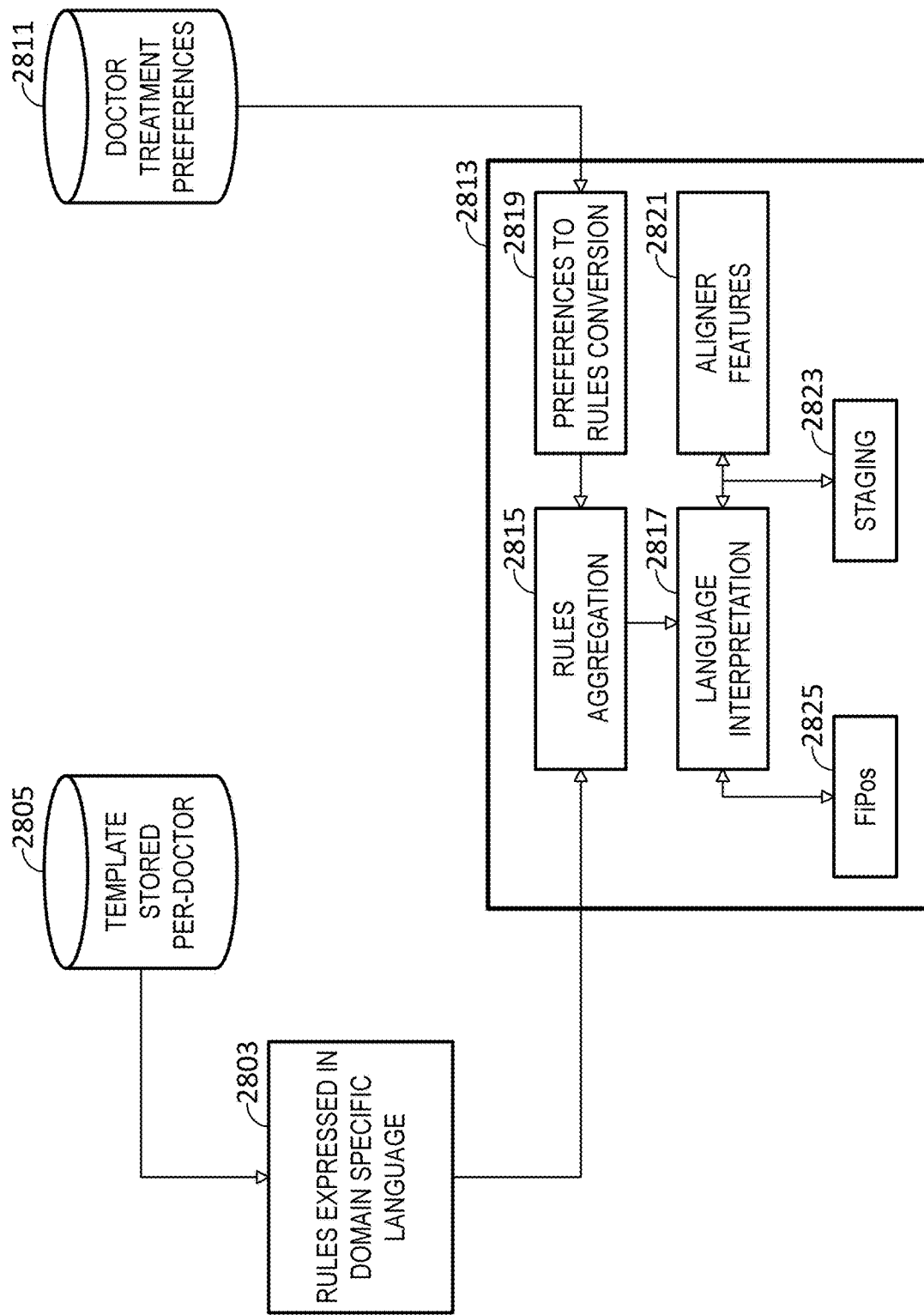
FIG. 28 shows another example of a method of generating a treatment plan in which the treatment plan generator (engine) accesses a set of user-specific treatment preferences.

FIG. 28 illustrates another example of this. In this example, the treatment plan optimizing engine or treatment plan optimizing generator 2813 includes a rules aggregator 2815 that combines the treatment preferences from user-specific treatment preferences that are stored in a database indexed by user 2805 that are converted via a domain-specific language 2803 into a first set of treatment rules, along with the user's patient-specific treatment preferences (specific to the instant case) 2811 that may also be converted by the domain-specific language 2819 into rules, and these rules may be combined 2815, then converted into treatment preferences using a language interpretation module 2817. The interpretation of these rules into treatment preferences may depend in part on the product (e.g., aligner features 2821), and may be provided to for determining staging 2823 and the optimal (e.g., comprehensive) final position 2825.

Thus, a set of rules may be expressed in a domain specific languages and associated with each user in a clinical database. A module may converts structured input (e.g., answers given by a doctor on a set of questions) into additional set of rules. These rules may be combined via a rules aggregation module which combines rules from multiple sources into a single rules list. The language interpretation module may takes any of these rules files as an input and interpret it to control the flow of FiPos, Staging and Aligner Features modules in order to create a treatment plan fully automatically, as described above.

Automatic Selection Treatment Plans

The methods and apparatuses described herein may provide multiple treatment plans and may allow the user (e.g., the dentist, orthodontist, dental professions) and/or in some variations the patient, to view all or a subset of these treatment plans, and to select one or more of these plans from which a series of dental appliances to be manufactured treatment. As described above, a very large number (e.g., 12, 18, 24, 30, 36, 40, 48, 50, 55, 60, 65, 70, 75, 100, 125, etc.) of treatment plans may be generated concurrently. Ordering or organizing the treatment plans, and in particular, determining the order of which treatment plans to display and/or how the user may toggle or select between these different treatment plans may therefore be helpful.

In any of these variations, the treatment plans may be sorted or organized by assigning a weight to each treatment plan based one or more criterion. For example, if 24 different treatment plans are generated, it would be helpful to automatically order the treatment plans using one or more criterion and to display them in that order. For example, the treatment plans may be ordered (assigned weights) and displayed based how comprehensive they are. The degree of comprehensiveness may be based on, for example, how closely the predicted final position of the tooth resembles the ideal final position of the patient's teeth (or an arbitrary final position) that is calculated as part of the procedure for generating the multiple treatment plans described above.

In some variations, different categories of treatment plans may be displayed concurrently, e.g., the most comprehensive treatment plans among treatment plans having a first characteristic (such as a those treatment plans limited to a first number of stages, e.g., 16 stages) may be displayed alongside the most comprehensive treatment plans having a second characteristic (such as those treatment plans limited to a second number of stages, e.g., 24 stages, or unlimited stages). The methods and systems described herein may determine how comprehensive each treatment plan is by comparing to the ideal final position and/or by applying ranking logic in which the each of one or more characteristics (also referred to herein as criterion) are used to determine the weighting. For example, treatment plans with interproximal reduction (IPR) may be weighted more than plans without IPR; treatments plans with extraction may be weighted higher; treatment plans with all attachments (e.g., anterior and posterior) may be weighted higher than plans without attachments, plans with only anterior attachments may be ranked higher than those with only posterior attachments, treatment plans including both upper and lower arch may be ranked higher thank those with only one of the dental arches; upper arch only treatment plans may be ranked higher than lower arch only, etc. Each of these characteristics may provide a number of points (weights) and the final ranking may be determined by the sum of these points for each treatment plan.

In addition to, or instead of, ordering the plurality of treatment plans based on the comprehensiveness of each treatment plan, the methods and apparatuses described herein may order the treatment plans based on one or more alternative or additional criterion, such as: the duration of the treatment plan, the number of stages, the amount of tooth movement achieved, etc. The criterion may be user selected or automatically selected. In some variations, the criterion may include, for example, a prediction of a user preference; the user's preference may be determined by machine learning, and may be specific to the user (e.g., based on prior/past preferences or selections for that user) or it may be generic.

For example, in any of these variations, the system may select two of the sorted treatment plans for side-by-side (concurrent) display; in some variations along with the original tooth position and/or the ideal tooth position calculated. As mentioned, the system may select the highest-ranked treatment plans within two (or more) categories for concurrent display. The ranked treatment plans may be displayed in an initial user interface screen, from which the user may then toggle between other treatment plans using one or more controls on the user interface, as described herein. In some variations, the system selects two of the most comprehensive treatment plans and show them to the user in an initial display for user review (e.g., using a treatment review system or sub-system). The system may weight each treatment plan based on the one or more criterion. For example, the system may weights of each treatment plan based on attributes such as IPR, use of attachments (and type of attachments, and/or number of attachments, and/or where attachments are used), presence or single arch or dual arch treatment for treatment plan, etc. As mentioned above, these criterion may also be used to select categories for concurrent display. The apparatus may sort and return the most comprehensive for the case.

Figure 42:
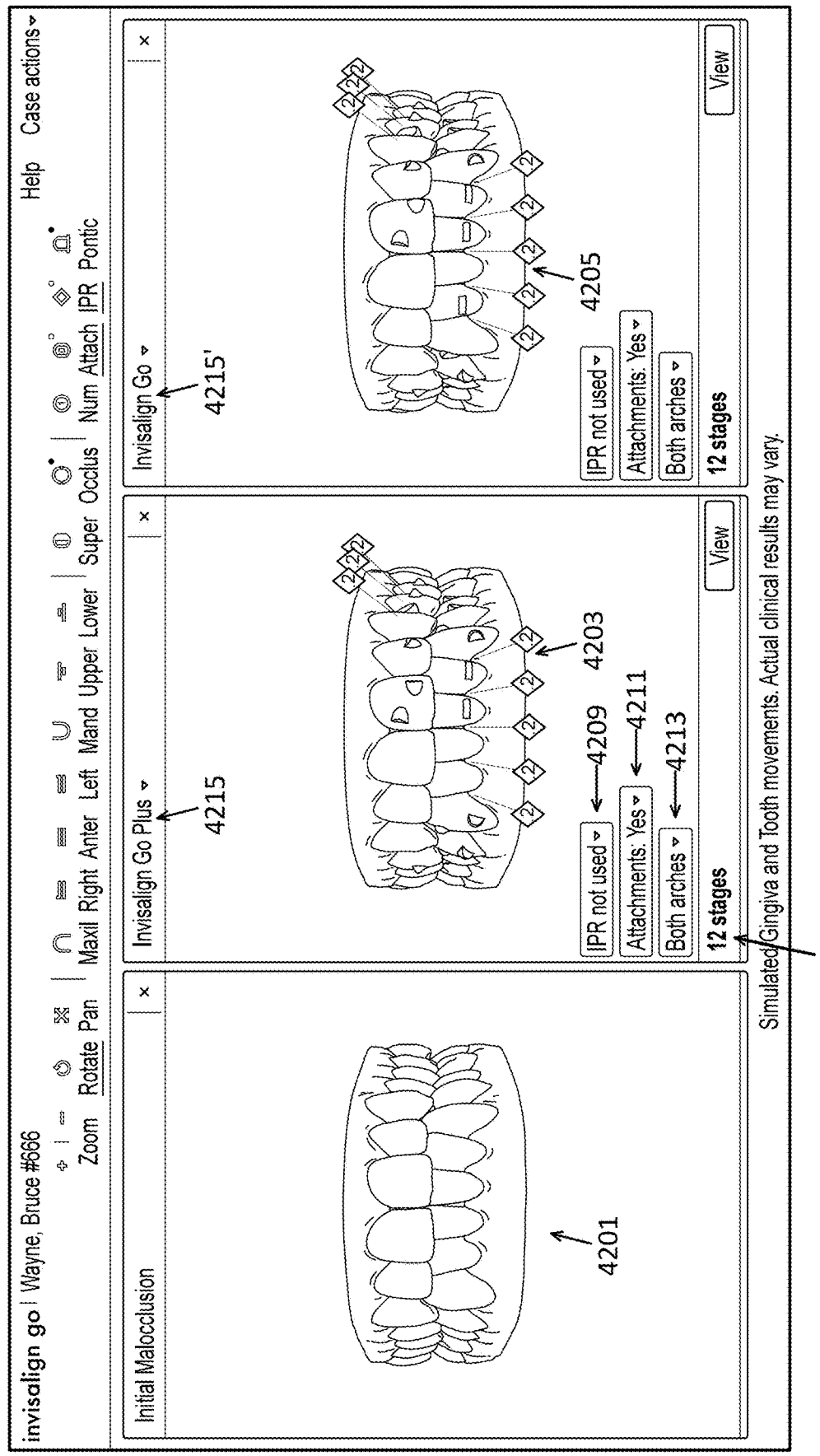
FIG. 42 illustrates one example of a mock-up of a user interface display, configured as a concurrent (side-by-side) display of treatment plan "cards", also referred to herein as a multiple card view.

FIG. 42 illustrates one example of a display showing side-by-side (concurrent) display of the sorted treatment plans (sorted for comprehensiveness based, e.g., clinical efficiency using ranked criterion). In this example, the first display screen shows the final tooth positon for plans with highest ranking in each of two categories: a first product, "Invisalign GO Plus" and a second category "Invisalign Go" product). A user can start review them without spending time to browse plans and finding best ones. Thus, the system and method may default to showing the highest-ranked treatment plans first, where treatment plans are ranked as described herein. In FIG. 42, the left side image 4201 shows the initial position of the patient's teeth. The right-side images may be images of the final tooth position for the highest-ranked treatment programs in two categories. For example, the middle image 4203 may the highest-ranked treatment program among those qualifying as the first product ("Invisalign GO Plus", e.g. limited to 12 or fewer stages). The right-side image 4205 may be the highest-ranked treatment program among those qualifying as the second product (e.g., "Invisalign GO" product, limited to 20 or fewer stages). This display view may be referred to as a multiple cards view. The display may also indicate features used as part of the calculations done on each treatment plan, such as the use/type of attachments 4211, the use/non-use of IPR 4201, the movement of both arches 4213, the product used 4215, etc. The display may also indicate the number of stages in the treatment plan 4217. As will be described below, in some variations these indicators may be selectable controls, e.g., drop-down menus, buttons, etc., that may allow the user to toggle between treatment plans.

In practice, when generating the one or more treatment plans, the system may set up how to rank the treatment plans for initial display, e.g., in the multiple cards display. For example, the system may look at all or a subset of the parameters used when calculating the multiple different treatment plans, including but not limited to: information about IPR (e.g., IPR used/IPR not used); information about attachments set (e.g., attachments: Yes/attachments: Posteriors only/attachments: No); arches to treat (single arch treatment/dual arch treatment); treatment type ("Invisalign Go"/"Invisalign Go Plus"), etc.

In some variations, if only one Product Type is available for the Doctor, then only one Treatment Plan shall be shown in the Multiple Cards View by default. Alternatively, in some variations, the multiple cards display may be used to display single arch/both arch views or other parameters. For single arch treatments submitted by the user, the most comprehensive single arch treatment plan may be selected and shown in the Multiple Cards View for each available product type.

As mentioned above, the each of the generated treatment plans may be ranked (e.g., scored). For example, table 1 (FIG. 43A) illustrates one example of a ranking of priorities that may be used to pick the most comprehensive single arch treatment plan within one treatment type to be shown to the user. In this example, lower numbers are higher ranked (e.g., 1 is the highest priority, 11 is the lowest priority). The simplified table of FIG. 43A shows the relationship between two categories (IPR and attachments) that may have two or more different states; other categories may be included, adding multiple dimensions. FIG. 43B is a table illustrating another example of a set of rankings for dual arch treatment; the same categories apply. Thus, when determining a ranking score for each treatment plan, the system may use a look-up table (or tables) similar to the tables shown in FIGS. 43A-43B, or it may apply a scoring system in which a particular number of "points" may be assigned for each parameter state (though note that this may result in 'ties' that may be permitted or reconciled using second set of preferences).

In the example of scoring using FIGS. 43A and 43B, when determining the initial display, the treatment plan with the lowest value score may be displayed. In variations in which one or more option are not available to the user (e.g., only one Product Type is available for the doctor, the user is not able/willing to provide IPR, etc.) then treatment plans, if generated, may be scored lower or removed. In some instances, even if not selected by the user (if, for example, the user indicates "no IPR"), treatment plans including these options may still be generated, so that the user can compare the use/non-use of these options directly.

From the initial view, the user may select one or more of the treatment plans for side-by-side comparison with other selected treatment plans and may begin to look though other (lower ranked) treatment plans by controlling the options/criterion. For example, the screen may include a "compare" or "save" control (e.g., button) that may allow the user to store this case for analysis. In some variations, a control may be used to move a selected treatment plan to one side of the display (e.g., in some variations replacing the initial view of the patient's teeth) so that it can be directly compared to other treatment plans.

In addition to directly toggling between options on the user interface, a control may also be provided to allow the user to see the next-ranked treatment plan (e.g., a button, or other control on the user interface, etc.). For example, selecting a "compare" button in the Multiple Cards view may be used for showing, in a dual arch treatment case, the next treatment plan according to the priorities scaling/ranking described above, such as in Table 2 of FIG. 43B. Clicking the same control (e.g., a "compare" button in the Multiple Cards view) for the single arch treatment case, will pick the next treatment plan according priorities described in both Tables 1 and 2 (e.g., FIGS. 43A and 43B). In one example, both treatment types are available for the user (e.g., Invisalign Go and Invisalign Go Plus), then clicking on "Compare" button in the Multiple Cards view, the system may pick the most comprehensive treatment plan with the Product Type which is absent in that view using FIG. 43A for the single arch treatments and using, e.g., Table 2 for the Dual Arch treatments. In some variations, the "Invisalign Go Plus" program may generate a treatment plan that can be shown in the Multiple Cards view (e.g., on the left) by default if both treatment types are shown. In some variations the Invisalign Go Treatment Plan may be shown at the right in the Multiple Cards view by default (e.g., if both treatment types are present).

Treatment Plan Filters

As discussed above, any of the methods and apparatuses described herein may be configured to display one or more treatment plans, typically by showing one or more of the model of the patient's dental arch(es) at one or more stages in the treatment plan, and allowing the user to toggle or switch between treatment plans by changing which parameters or constraints specified when generating the treatment plans. Thus, a user may select, in real-time, an appropriate treatment plan by using filters, toggles, or switches against the clinical parameters, such as one or more of: interproximal reduction (No IPR/No, IPR), Attachments (all attachments, No Attachments, anterior only attachments, posterior only attachments, etc.), etc. These controls may be referred to as clinical filters and the user may select the most appropriate treatment plan for the particular patient using these clinical filters to rapidly compare treatment plans. Using clinical filters may also allow the user to fine-tune a selected treatment plan. For example, in some variations the user may select another value for IPR or attachments using the filters and may then immediately submit the modified treatment plan to generate a new family of modified treatment plans that may be viewed immediately or shortly thereafter.

Thus, by toggling between treatment plans, the user may automatically and quickly browse between multiple treatment plans by choosing key features that can affects final position, such as the use and placement of attachments, IPRs, treatment of one or both arches, etc. Each filter can display one or more notification or tip if the feature is not available for a particular case.

Figure 44:
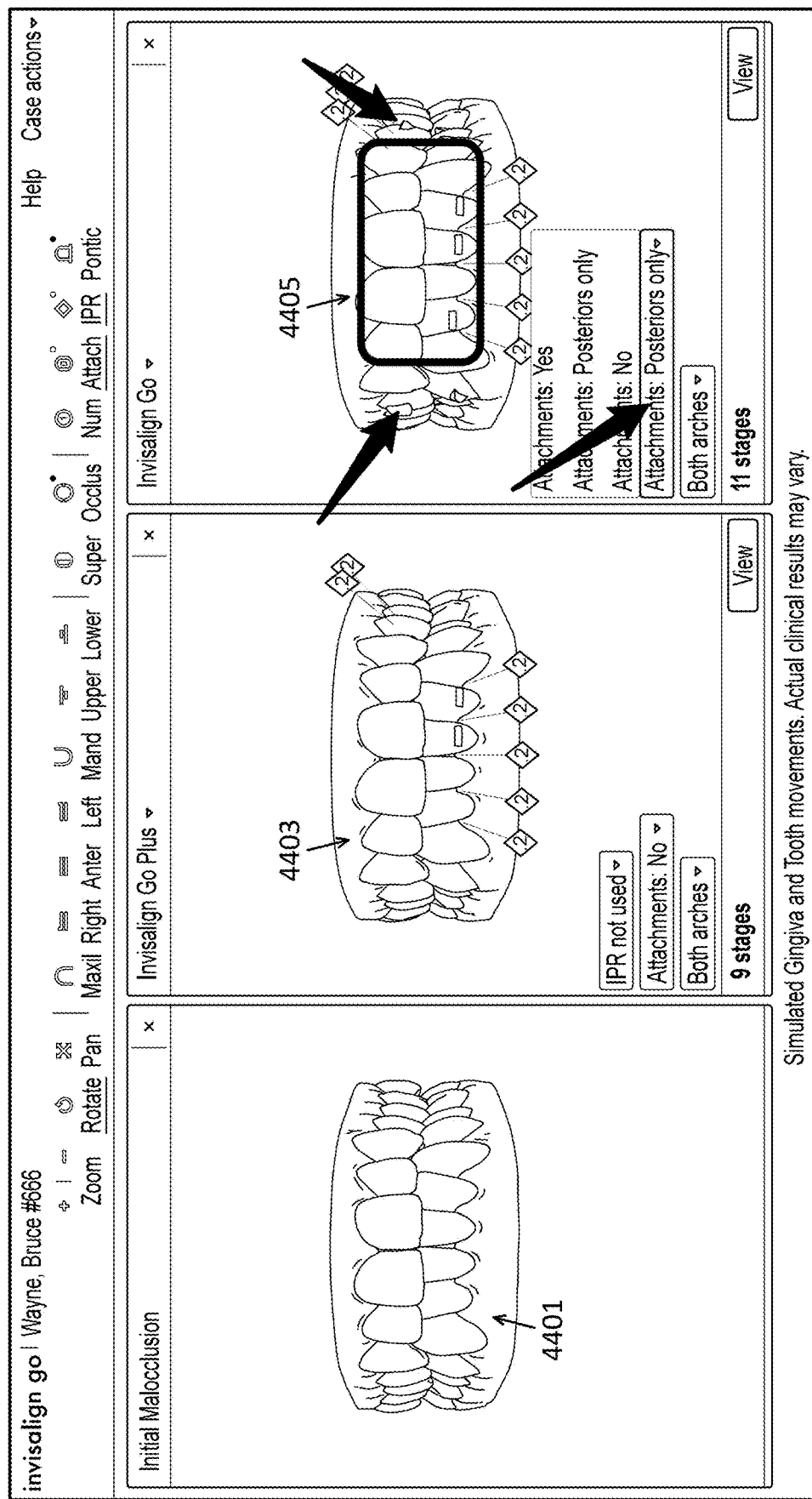
FIG. 44 is another example of a user interface display, illustrating the use of treatment plan filters allowing the user to switch or toggle between different treatment plans for display.

For example, FIG. 44 is a mock-up of a multi-card view that shows three panels. The first panel shows an image (3D model from a scan) of the patient's current teeth 4401. The middle panel shows an image of the patient's teeth from a first treatment plan 4403 (e.g., a treatment plan having 9 stages, using the constraints of the "Invisalign Go Plus" product, which has a limited number of stages permitted, in which IPR was not used, no attachments were used, and aligners are used on both arches). Similarly, the third panel shows an image of the patient's teeth from a second treatment plan 4405 (e.g., a treatment plan having 11 stages, using the constrains of the "Invisalign Go Plus" product, in which IPR was not used, but posterior only attachments is being selected by a user using the control or filter, shown here as a button on the user interface that pulls out a drop-down menu allowing the user to specify which type of attachments are use (e.g., no attachments, yes attachments or posterior only attachments); in FIG. 44, the user is preparing to select "attachments posterior only" to switch the third card to display this variation In general in the displays showing the initial malocclusion 4401 and the different treatment plans 4403 and 4405 may show a flat or static view of the teeth based on the simulated movement per the treatment plan; alternatively an animation may be used, showing tooth movement across multiple stages of treatment. In some variations, the stage shown may be the final stage (showing all movement); other stages may also be shown. In some variations the 3D model showing the tooth position may be rotated (or may rotate automatically) to show different perspectives.

Figure 45:
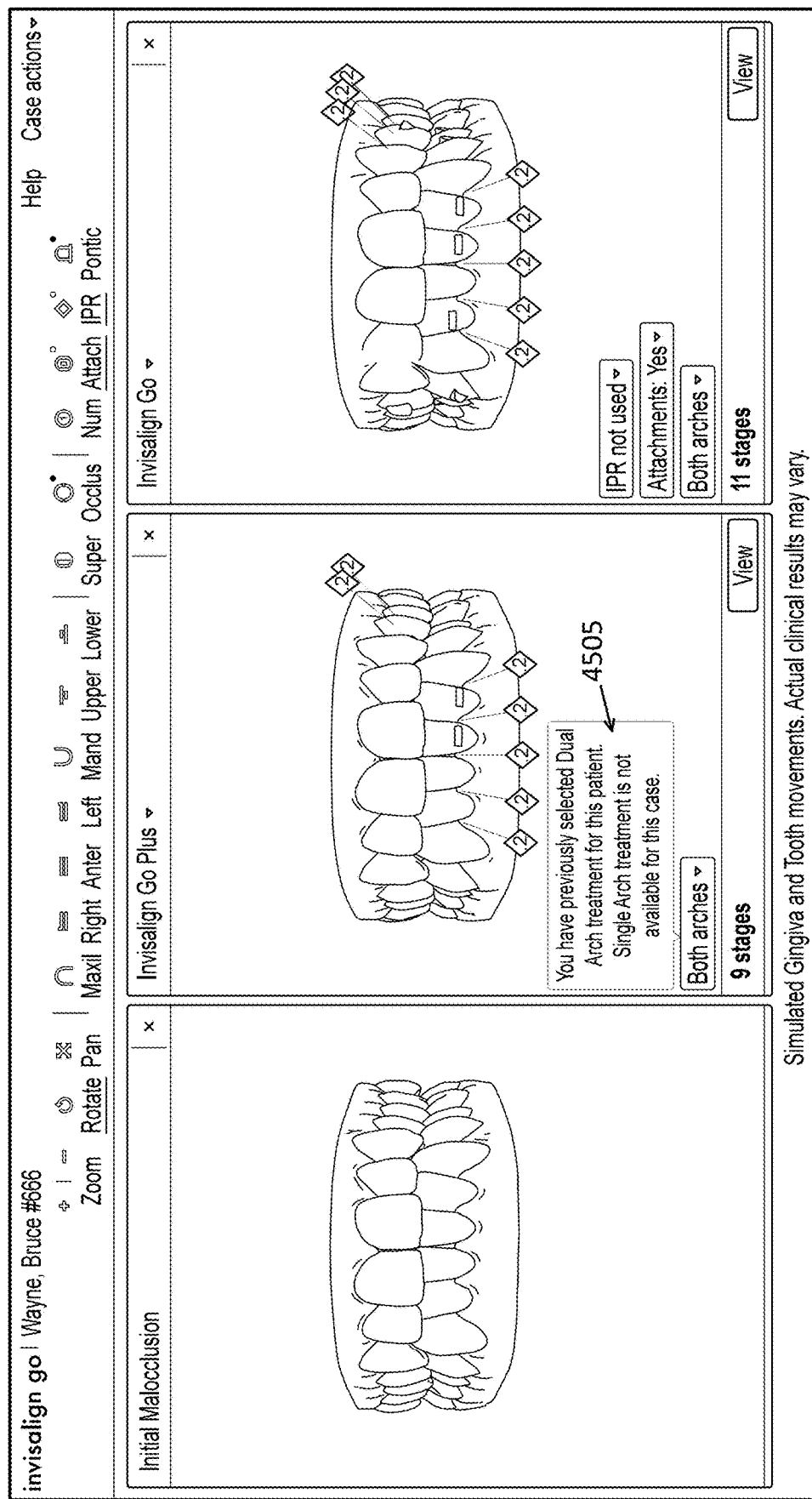
FIG. 45 is another example of a user interface display, illustrating the use of treatment plan filters allowing the user to switch or toggle between different treatment plans for display.

As mentioned above, a filter may indicate one or more notification or tip if the feature is not available for a particular case. For example, FIG. 45 illustrates a display similar to that shown in FIG. 44, showing side-by-side comparisons of the original tooth positions, and two treatment plans. In this example, although the display includes an indicator/control the number of arches (e.g., both arches, single arch) only treatment plans with a single arch were generated, and therefore if the user attempts to switch to view 'single arch' treatment plans, as shown in the middle image, a notification 4505 indicating that only dual treatment is available may be provided. In some variations the indicator may be grayed out, preventing it from being selected.

In general, any of these displays may also include an indication of the cost or price associated with the treatment plan. For example, one of the filters may allow the doctor to compare two different product types having different price. Higher price products may have, for example, more stages in the treatment and have a wider range for clinical conditions. Thus, in any of these examples, the doctor may use filters to provide an overview of what treatments (e.g., what treatment outcomes) may be best for the patient and which may be automatically suggested by the system, as described above, for a particular patient. In some variations, the doctor can use these filters to review a particular clinical feature usage (e.g., comparing one plan with IPR to another plan without IPR, etc.) and compare results. The use of filters may also allow a user to see clinical details for the selected plan.

Figure 46:
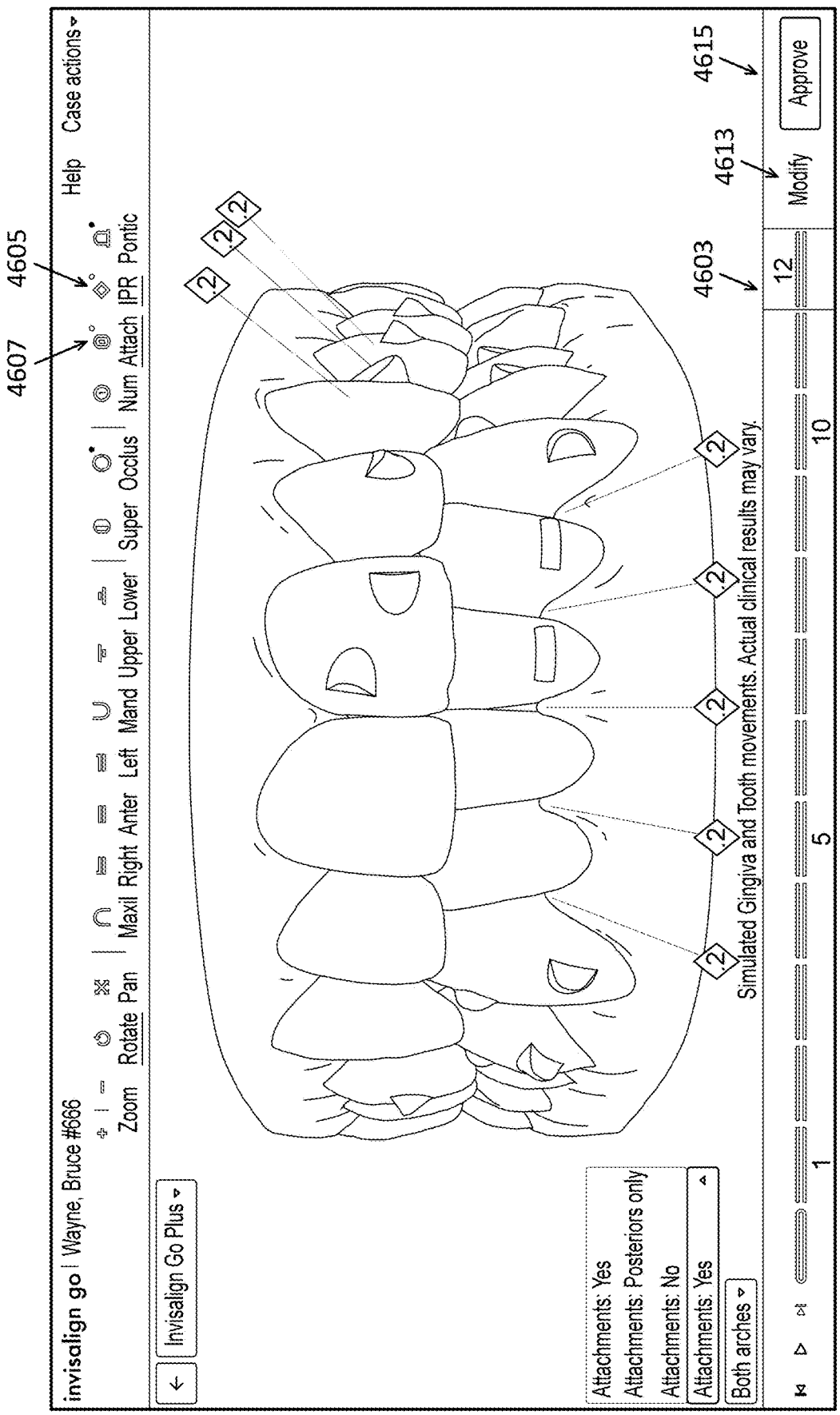
FIG. 46 illustrates an example of a detailed view of a single treatment plan, showing the tooth (and any modifications to the teeth, including attachments, IPR, etc.) for a selected stage of the treatment plan.

Filters may also be applied when reviewing a single plan in greater detail, as illustrated in FIG. 46. This view may be referred to as a "single treatment plan" view (STP view). In contrast, the views shown in FIGS. 44 and 45 may be referred to as "multiple treatment plan views" (MTP views). In the example shown in FIG. 46, the same controls (e.g., configured as filters) may be included; in addition, the user may select which stage 4603 to review or to animate between them. In addition, the user interface may include one or more controls for modifying the treatment plan 4613. For example, the user may select 'modify" and may use a tool to add/remove attachments 4607 and/or pontics, move the attachment, indicate IPR 4605, etc. Finally, if the treatment plan looks good, the user may indicate approval 4615.

Figure 47:
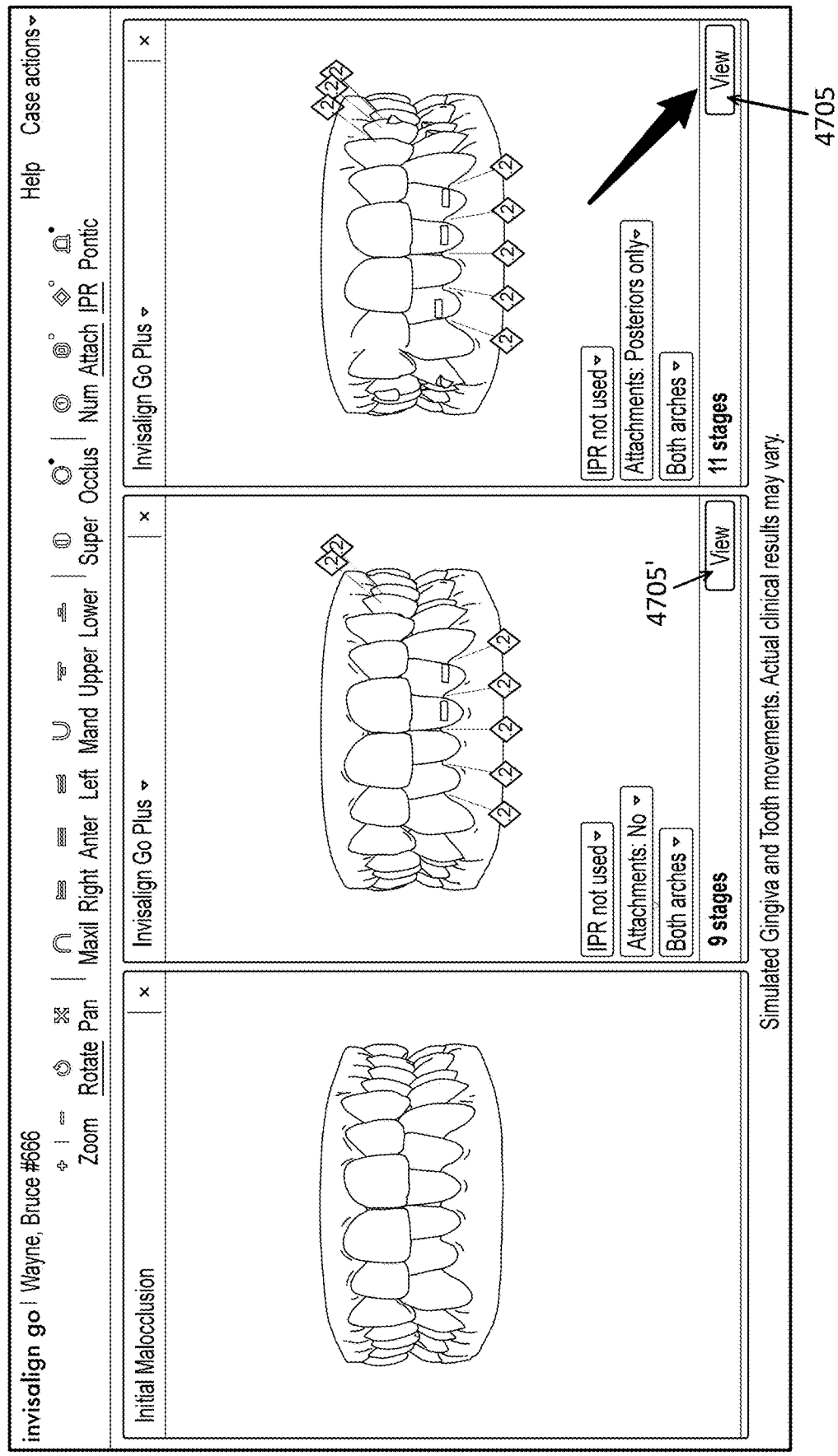
FIG. 47 is another example of a multiple treatment plan (MTP) user interface similar to that shown in FIGS. 42, 44 and 45, above.
Figure 48:
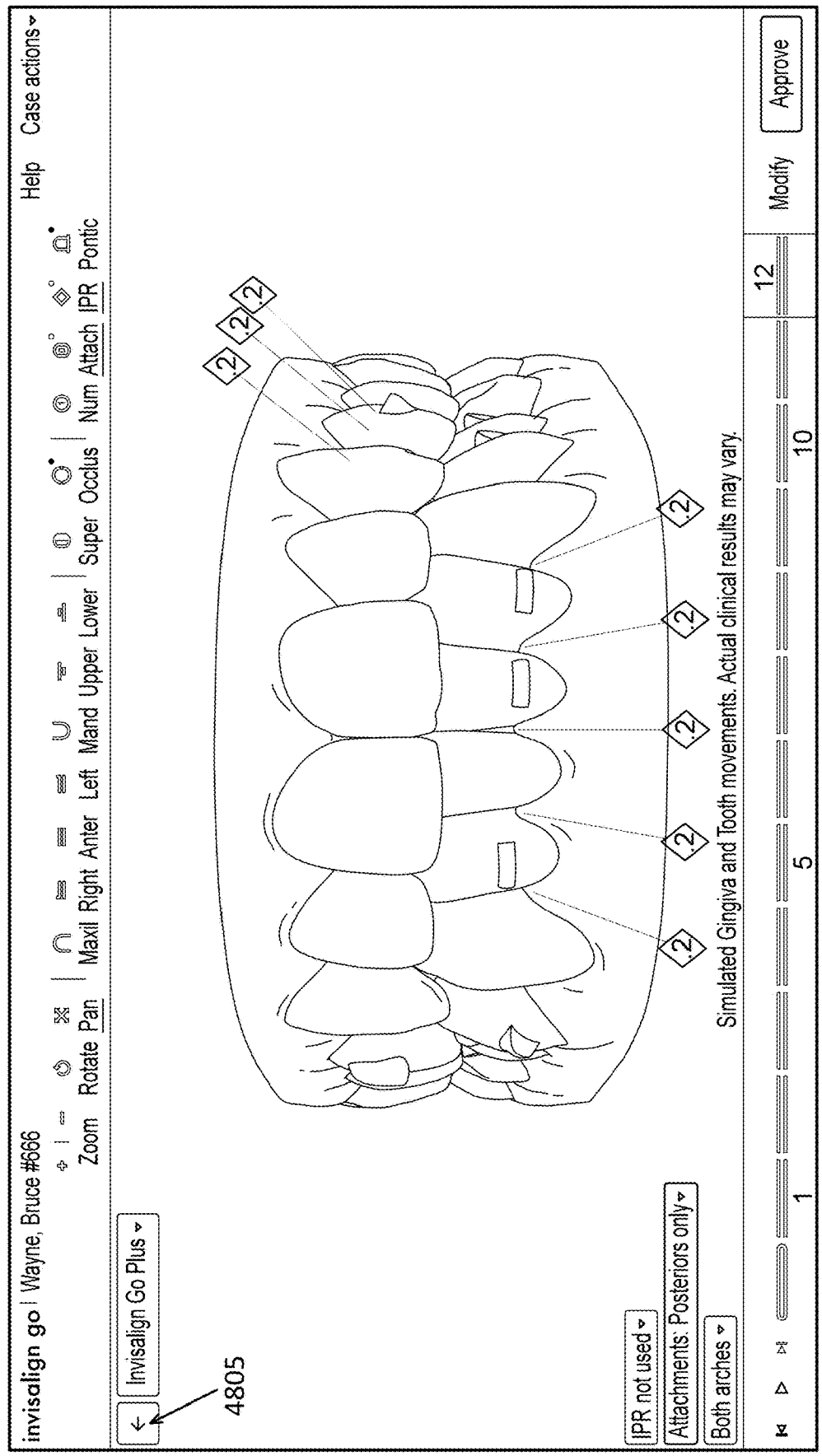
FIG. 48 is an example of a single treatment plan (STP) user interface, similar to that shown in FIG. 46, allowing detailed review of a treatment plan and toggling between other treatment plans.

In general, the user may also switch between multiple treatment plan views and single treatment plan views. For example, FIG. 47 shows another example of a multiple treatment plan view similar to that described above, showing a side-by-side comparison between two (or more) treatment plans, as well as the patient's original tooth configuration ("initial malocclusion"). The MTP view may show essential high-level information about the projected outcomes of the multiple alternative treatments and initial malocclusion. In contrast, the STP view may show how to achieve the selected treatment plan. Switching between these different views may help the user review the selected plan(s) and maximized to whole screen. In FIG. 47, the user may select one of the treatment plans displayed by actuating the control (shown as a button 4705, 4705' labeled "view" on the user interface). To open a Single Treatment Plan view (also referred to herein as a Single Card View) from a Multiple Cards (multiple treatment plan view), the user may select this control as shown in FIG. 47. This may open up the single treatment plan view of that treatment plan, as shown in FIG. 48. The STP may include features not in the MPT display, such as, for example: play staging, free form commenting, editing/modification of the treatment plan, etc. The user may also switch back to the multiple view by, for example, selecting a control 4805 for MTP, or "back".

Figure 49:
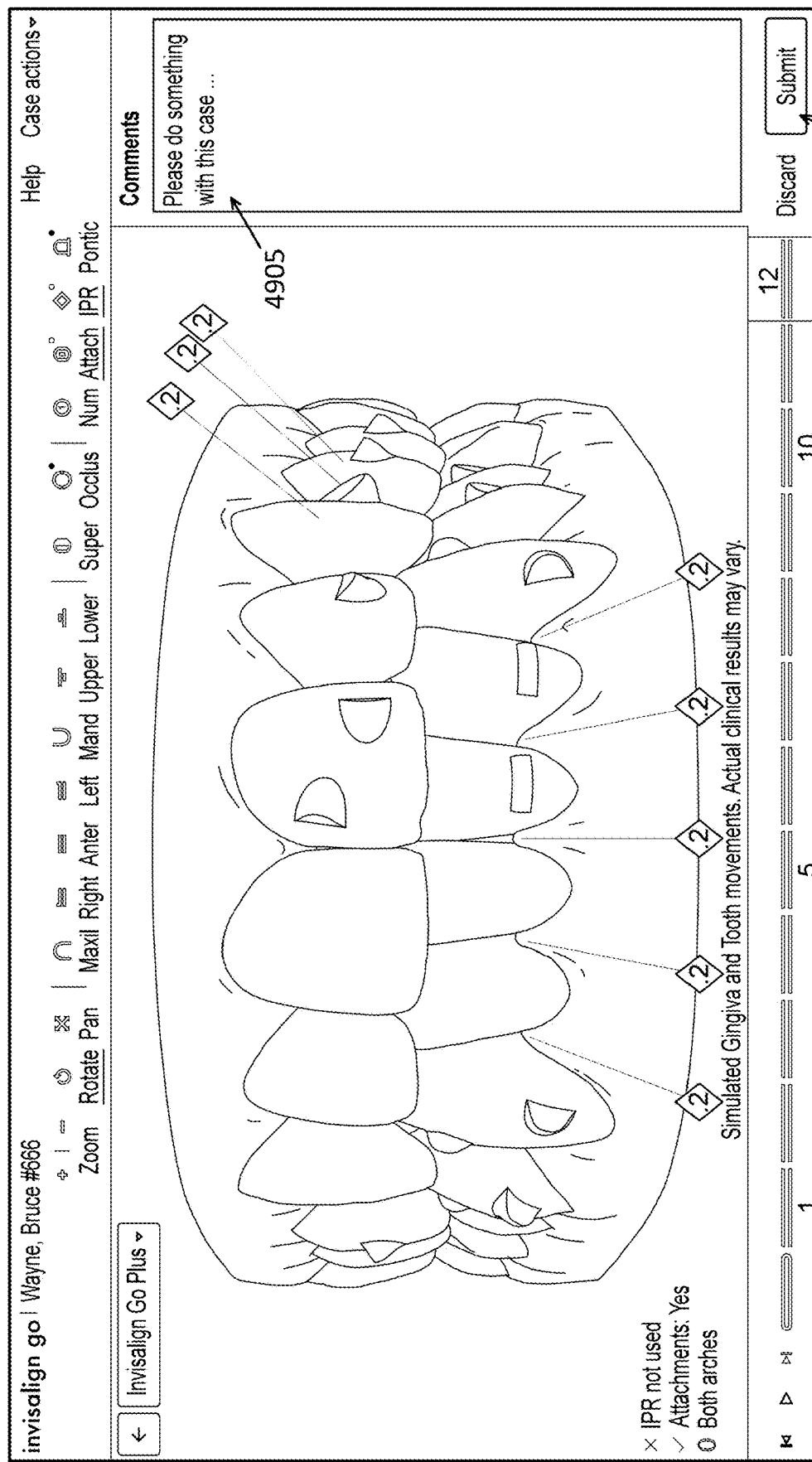
FIG. 49 is another example of an STP user interface.

The single treatment plan display (e.g., user interface) may allow the user to review staging, features available on each stage of the treatment, and teeth position on each stage. As shown in FIG. 49, in some variations the STP view may allow a user to approve the selected plan and send it to manufacturing or to add free form comments 4905, asking the manufacturing technician to modify (e.g., improve or change) anything in this treatment plan and send the treatment plan(s) back to the technician for a treatment plan update 4907, which may be manually, automatically or semi-automatically performed. In some variations, the user may view details for any plan in a MTP view by clicking on a "view" control (e.g., button). In some variations, the STP view may allow the doctor to see detailed staging info at the bottom of the screen, such as: treatment length for upper and lower arches, what type of aligners will be manufactured for each stage (active or passive), overcorrection stages if they are present for the treatment, animated controls to play/pause treatment animation, etc.

In any of these views, tools (e.g., on the toolbar) may be used to allow the user to review and/or modify features on any stage (attachments, IPRs, pontics, etc.), as discussed above in reference to FIG. 46. For example, the user may click on an "approve" control (e.g., button) to send the selected treatment plan directly to manufacturing. Alternatively, clicking on a "modify" control (e.g., button) may add/edit free form comments and send the case to a technician for an update after actuating a "submit" control 4907.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of creating a treatment plan to align a patient's teeth using a plurality of removable aligners to be worn in sequential stages, the method comprising:
   receiving, in a processor, a digital model of the patient's teeth;
   accessing, by the processor, a set of treatment preferences, a comprehensive final position of the patient's teeth, and a set of treatment details;
   selecting a plurality of numerically expressed treatment targets from a memory accessible to the processor, based on the set of treatment details, the set of treatment preferences and the comprehensive final position of the patient's teeth;
   combining the plurality of numerically expressed treatment targets to form a single numerical function;
   selecting a plurality of numeric limits on the single numerical function based on the set of treatment preferences;
   minimizing the single numerical function subject to the plurality of numeric limits to get a solution vector including all stages forming the treatment plan;
   mapping the solution vector to the treatment plan, wherein the treatment plan includes a final tooth position that is different from the comprehensive final position of the patient's teeth; and
   generating one or more aligners based on the treatment plan.

2. The method of claim 1, further comprising receiving, in the processor: the digital model of the patient's teeth, the set of treatment preferences or a reference to the set of treatment preferences, the comprehensive final position of the patient's teeth, and the set of treatment details or an identifier identifying the set of treatment details.

3. The method of claim 2, wherein the identifier identifying the set of treatment details identifies a product having a defined set of treatment details accessible to the processor.

4. The method of claim 1, wherein the set of treatment preferences comprise one or more of: an indicator of which teeth are not permitted to move, an indication of which of the patient's teeth should not have an attachment, an indicator of which of the patient's teeth to treat, an indicator of tooth class correction amount, an indicator that interproximal reduction is to be used, an indicator that arch expansion is to be used, and indicator of spacing between the patient's teeth, an indicator or tooth levelling.

5. The method of claim 1, wherein the set of treatment details comprises one or more of: a maximum allowed number of stages, whether attachments to the patient's teeth are allowed, a maximum allowed tooth root movement, a maximum allowed tooth crown movement, and a maximum allowed tooth rotation.

6. The method of claim 1, wherein combining the numerically expressed treatment targets further comprises weighting each of the numerically expressed treatment targets in the single numerical function.

7. The method of claim 1, wherein the single numerical function includes, for a set of teeth of the patient's teeth, a sum of at least: a difference from an initial position of the patient's teeth compared to the comprehensive final position of the patient's teeth, a measure of misalignment in an x direction for the patient's teeth, a measure of misalignment in a z direction for the patient's teeth, a measure of misalignment of a dental arch of the patient's teeth, a measure of diastema between neighboring teeth of the patient's teeth, a measure of overjet of the patient's teeth, a measure of overbite of the patient's teeth, a measure of collisions between the patient's teeth, a measure of the difference between an arch of the patient's teeth and the comprehensive final position of the patient's teeth, a measure of the difference in leveling between the patient's teeth and the comprehensive final position of the patient's teeth, a measure of an amount of occlusion between the patient's teeth of the patient's upper and lower jaws, a measure of a difference in the amount of occlusion between the patient's teeth and the comprehensive final position of the patient's teeth, a measure of an amount of mesial to distal round trips of the patient's teeth, a measure of the amount of buccal to lingual round trips of the patient's teeth, and a measure of a number of aligner stages compared to a target number of aligner stages from the set of treatment details.

8. The method of claim 1, wherein the single numerical function includes, for a set of teeth of the patient's teeth, a sum of at least: a difference from an initial position of the patient's teeth compared to the comprehensive final position of the patient's teeth, a measure of misalignment for the patient's teeth, and a measure of a number of aligner stages compared to a target number of aligner stages from the set of treatment details.

9. The method of claim 1, further comprising adjusting the plurality of numerically expressed treatment targets into a plurality of adjusted numerically expressed treatment targets based on: the set of treatment details, the set of treatment preferences and the comprehensive final position of the patient's teeth, further wherein combining the plurality of numerically expressed treatment targets comprises combining the plurality of adjusted numerically expressed treatment targets.

10. The method of claim 1, wherein the plurality of numeric limits comprises one or more of: a maximum velocity of tooth movement, a maximum amount of collision between teeth, a tooth movement limitation, a maximum number of aligner stages, a maximum amount of occlusion, a maximum amount of overbite, a maximum amount of overjet, and a maximum midline position.

11. The method of claim 1, wherein minimizing the single numerical function subject to the plurality of numeric limits comprises using a constrained optimization method to get the solution vector.

12. The method of claim 11, wherein the constrained optimization method comprises an interior point method.

13. The method of claim 1, wherein mapping the solution vector to the treatment plan comprises converting the solution vector into a set of key frames for each tooth of the patient's teeth, corresponding to a stage number, and positional information for each tooth of the patient's teeth, including an x coordinate, a y coordinate, a z coordinate, and an angulation, an inclination and a rotation angle.

14. The method of claim 1, further comprising displaying the final tooth position of the treatment plan.

15. A method of creating a treatment plan to align a patient's teeth using a plurality of removable aligners to be worn in sequential stages, the method comprising:
    receiving, in a processor, a digital model of the patient's teeth;
    accessing, by the processor, a set of treatment preferences, a comprehensive final position of the patient's teeth, and a set of treatment details;
    selecting a plurality of numerically expressed treatment targets from a memory accessible to the processor based on: the set of treatment details, the set of treatment preferences and the comprehensive final position of the patient's teeth;
    adjusting the plurality of numerically expressed treatment targets into a plurality of adjusted numerically expressed treatment targets based on: the set of treatment details, the set of treatment preferences and the comprehensive final position of the patient's teeth;
    combining the plurality of adjusted numerically expressed treatment targets to form a single numerical function;
    setting a plurality of numeric limits on the single numerical function based on the set of treatment preferences;
    iteratively minimizing the single numerical function subject to the plurality of numeric limits to get a solution vector including all stages forming the treatment plan;
    mapping the solution vector to the treatment plan, wherein the treatment plan includes a final tooth position that is different from the comprehensive final position of the patient's teeth; and
    generating one or more aligners based on the treatment plan.

16. A system comprising:
    a memory that stores computer-program instructions; and
    one or more processors configured to execute the computer-program instructions, that when executed by the one or more processors, perform a computer-implemented method comprising:
        receiving, in the one or more processors, a digital model of a patient's teeth;
        accessing a set of treatment preferences, a comprehensive final position of the patient's teeth, and a set of treatment details;
        selecting a plurality of numerically expressed treatment targets from the memory accessible to the one or more processors, based on the set of treatment details, the set of treatment preferences and the comprehensive final position of the patient's teeth;
        combining the plurality of numerically expressed treatment targets to form a single numerical function;
        selecting a plurality of numeric limits on the single numerical function based on the set of treatment preferences;
        minimizing the single numerical function subject to the plurality of numeric limits to get a solution vector including all stages forming a treatment plan;
        mapping the solution vector to the treatment plan, wherein the treatment plan includes a final tooth position that is different from the comprehensive final position of the patient's teeth; and
        generating, using a manufacturing device, one or more aligners based on the treatment plan.

17. The of claim 16, wherein the set of treatment preferences comprise one or more of: an indicator of which teeth are not permitted to move, an indication of which of the patient's teeth should not have an attachment, an indicator of which of the patient's teeth to treat, an indicator of tooth class correction amount, an indicator that interproximal reduction is to be used, an indicator that arch expansion is to be used, and indicator of spacing between the patient's teeth, an indicator or tooth levelling.

18. The system of claim 16, wherein the set of treatment details comprises one or more of: a maximum allowed number of stages, whether attachments to the patient's teeth are allowed, a maximum allowed tooth root movement, a maximum allowed tooth crown movement, and a maximum allowed tooth rotation.

19. The system of claim 16, wherein combining the numerically expressed treatment targets further comprises weighting each of the numerically expressed treatment targets in the single numerical function.

20. The system of claim 16, wherein the single numerical function includes, for a set of teeth of the patient's teeth, a sum of at least: a difference from an initial position of the patient's teeth compared to the comprehensive final position of the patient's teeth, a measure of misalignment in an x direction for the patient's teeth, a measure of misalignment in a z direction for the patient's teeth, a measure of misalignment of a dental arch of the patient's teeth, a measure of diastema between neighboring teeth of the patient's teeth, a measure of overjet of the patient's teeth, a measure of overbite of the patient's teeth, a measure of collisions between the patient's teeth, a measure of the difference between an arch of the patient's teeth and the comprehensive final position of the patient's teeth, a measure of the difference in leveling between the patient's teeth and the comprehensive final position of the patient's teeth, a measure of an amount of occlusion between the patient's teeth of the patient's upper and lower jaws, a measure of a difference in the amount of occlusion between the patient's teeth and the comprehensive final position of the patient's teeth, a measure of an amount of mesial to distal round trips of the patient's teeth, a measure of the amount of buccal to lingual round trips of the patient's teeth, and a measure of a number of aligner stages compared to a target number of aligner stages from the set of treatment details.

21. The system of claim 16, wherein the single numerical function includes, for a set of the patient's teeth, a sum of at least: a difference from an initial position of the patient's teeth compared to the comprehensive final position of the patient's teeth, a measure of misalignment for the patient's teeth, and a measure of a number of aligner stages compared to a target number of aligner stages from the set of treatment details.

22. The system of claim 16, wherein the computer-implemented method further comprises adjusting the plurality of numerically expressed treatment targets into a plurality of adjusted numerically expressed treatment targets based on: the set of treatment details, the set of treatment preferences and the comprehensive final position of the patient's teeth; further comprising combining the plurality of numerically expressed treatment targets by combining the plurality of adjusted numerically expressed treatment targets.

23. The system of claim 16, wherein the plurality of numeric limits comprises one or more of: a maximum velocity of tooth movement, a maximum amount of collision between teeth, a tooth movement limitation, a maximum number of aligner stages, a maximum amount of occlusion, a maximum amount of overbite, a maximum amount of overjet, and a maximum midline position.

24. The system of claim 16, wherein the computer-implemented method further comprises minimizing the single numerical function subject to the plurality of numeric limits using a constrained optimization method to get the solution vector.

25. The system of claim 24, wherein the constrained optimization method comprises an interior point method.

26. The system of claim 16, wherein mapping the solution vector to the treatment plan includes converting the solution vector into a set of key frames for each tooth, corresponding to a stage number, and positional information for each tooth of the patient's teeth, including an x coordinate, a y coordinate, a z coordinate, and an angulation, an inclination and a rotation angle.

27. The system of claim 16, wherein the computer-implemented method further comprises providing the final tooth position of the treatment plan for display.

* * * * *